US006130316A

United States Patent [19]
Freeman et al.

[11] Patent Number: 6,130,316
[45] Date of Patent: *Oct. 10, 2000

[54] FUSION PROTEINS OF NOVEL CTLA4/CD28 LIGANDS AND USES THEREFORE

[75] Inventors: Gordon J. Freeman, Brookline; Lee M. Nadler, Newton; Gary S. Gray, Brookline; Edward Greenfield, Randolph, all of Mass.

[73] Assignees: Dana Farber Cancer Institute, Boston; Replingen Corporation, Cambridge, both of Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/280,757

[22] Filed: Jul. 26, 1994

Related U.S. Application Data

[63] Continuation-in-part of application No. 08/109,393, Aug. 19, 1993, abandoned, which is a continuation-in-part of application No. 08/101,624, Jul. 26, 1993, abandoned, which is a continuation-in-part of application No. 08/147,773, Nov. 3, 1993, abandoned.

[51] Int. Cl.[7] ........................ C07K 19/00; C07K 14/705; C07H 21/00
[52] U.S. Cl. ..................... 530/350; 530/387.3; 536/23.4; 536/23.5; 435/69.1; 435/69.7
[58] Field of Search .................. 536/23.5, 23.4; 530/350, 386, 387.3, 402, 403; 435/69.7, 172.1, 172.3, 240.2, 252.3, 320.1, 69.1; 424/192.1, 193.1; 935/10

[56] References Cited

U.S. PATENT DOCUMENTS

| 5,116,964 | 5/1992 | Capon et al. | 536/27 |
|---|---|---|---|
| 5,434,131 | 7/1995 | Linsley et al. | 514/2 |

FOREIGN PATENT DOCUMENTS

WO 93/00431  1/1993  WIPO.

OTHER PUBLICATIONS

Inobe, M. et al. (1994) "Identification of an Alternatively Spliced Form of the Murine Homologue of B7", *Biochemical and Biophysical Research Communication* 200(1):443–449.

Boussiotis, V.A. et al. (1993) "Activated Human B Lymphocytes Express Three CTLA–4 Counterrecepctors that Costimulate T–Cell Activation" *Proc Natl. Acad. Sci. USA* 90: 11059–11063.

Freedman, A. S. et al. (1987) "B7, A B Cell–Restricted Antigen That Identifies Preactivated B Cells" *Journal of Immunology* 139(10): 3260–3267.

Freeman, G. J. et al. (1989) "B7, A New Member of the Ig Superfamily with Unique Expression on Activated and Neoplastic B Cells" *Journal of Immunology* 143(8): 2714–2722.

Freeman, G.J. et al. (1993) "Cloning of B7–2: A CTLA–4 Counter–Receptor That Costimulates Human T Cell Proliferation" *Science* 262: 909–911.

Freeman,G. J. et al. (1991) "Structure, Expression, and T Cell Costimulatory Activity of the Murine Homologue of the Human B Lymphocyte Activation Antigen B7"*Journal of Experimental Medicine* 174: 625–631.

Gimmi, C. D. et al. (1991) "B–Cell Surface Antigen B7 Provides a Constimulatory Signal That Induces T Cells to Proliferate and Secrete Interleukin 2" *PNAS* 88: 6575–6579.

Hollenbaugh and A. Aruffo (1992) "Construction of Immunoglobulin Fusion Proteins" *Immunology Suppl.* 4, Unit 10.19: 1–11.

Lenschow, D.J. et al. (1993) "Expression and Functional Significance of an Additional Ligand for CTLA–4" *Proc. Natl. Acad. Sci USA* 90: 11054–11058.

Linsley, P. S. et al. (1991) "Binding of the B Cell Activation Antigen B7 to DC28 Costimulates T Cell Proliferation and Interleukin 2 mRNA Accumulation" *Journal of Experimental Medicine* 173: 721–730.

Reiser, H. et al. (1992) "Murine B7 Antigen Provides an Efficient Consitmulatory Signal for Activation of Murine T Lymphocytes Via T Cell Receptor/CD3 Complex" *PNAS* 89: 271–275.

Schwartz, R. H. (1990), "A Cell Culture Model for T Lymphocyte Clonal Anergy" *Science* 248: 1349–1356.

Southern, S.O. et al. (1989) "Induction of the H–2 D Antigen During B Cell Activation" *J. Immunology* 142(1): 0336–0342.

Thompson, C. B. et al. (1989) "CD28 Activation Pathway Regulates the Production of Multiple T–Cell Derived Lymphokines/Cytokines" *PNAS* 86:1333–1337.

*Primary Examiner*—Lorraine Spector
*Attorney, Agent, or Firm*—Lahive & Cockfield LLP; Amy E. Mandragouras; Megan E. Williams

[57] ABSTRACT

Nucleic acids encoding novel CTLA4/CD28 ligands which costimulate T cell activation are disclosed. In one embodiment, the nucleic acid has a sequence which encodes a B lymphocyte antigen, B7-2. Preferably, the nucleic acid is a DNA molecule comprising at least a portion of a nucleotide sequence shown in FIG. 8, SEQ ID NO:1 or FIG. 14, SEQ ID NO:23. The nucleic acid sequences of the invention can be integrated into various expression vectors, which in turn direct the synthesis of the corresponding proteins or peptides in a variety of hosts, particularly eukaryotic cells, such as mammalian and insect cell culture. Also disclosed are host cells transformed to produce proteins or peptides encoded by the nucleic acid sequences of the invention and isolated proteins and peptides which comprise at least a portion of a novel B lymphocyte antigen. Proteins and peptides described herein can be administered to subjects to enhance or suppress T cell-mediated immune responses.

69 Claims, 26 Drawing Sheets

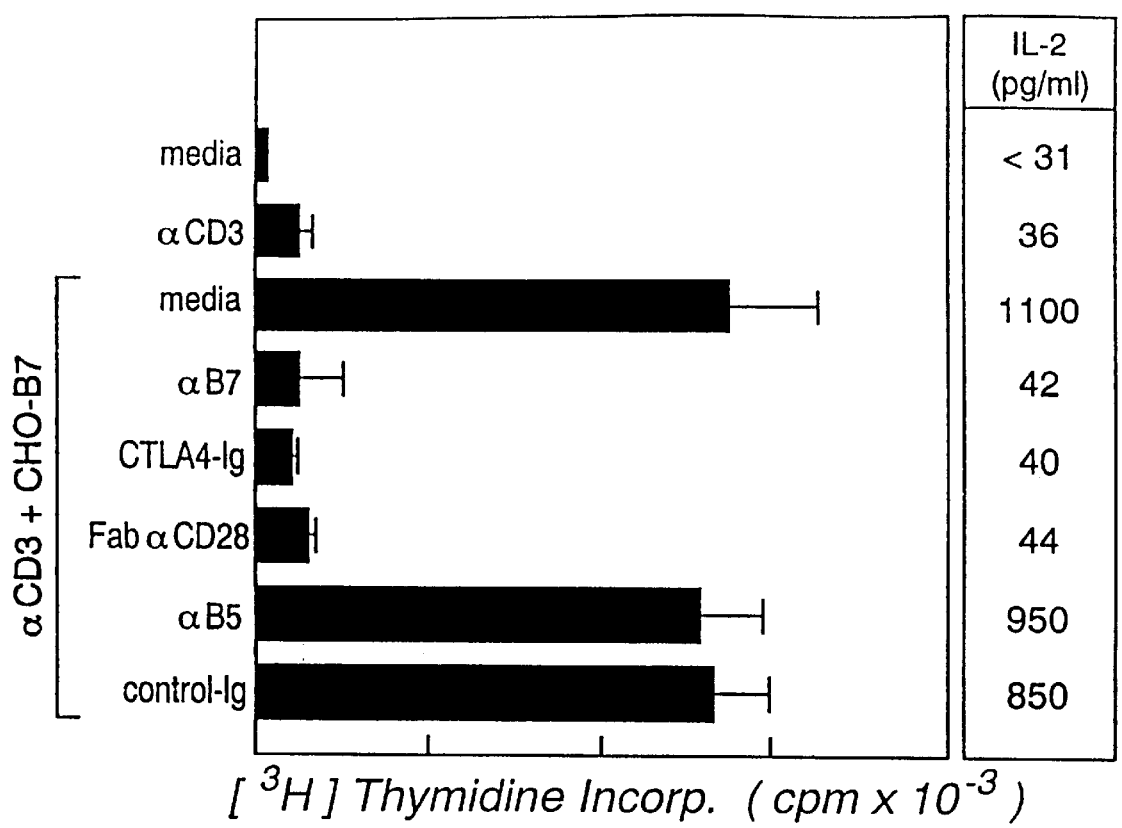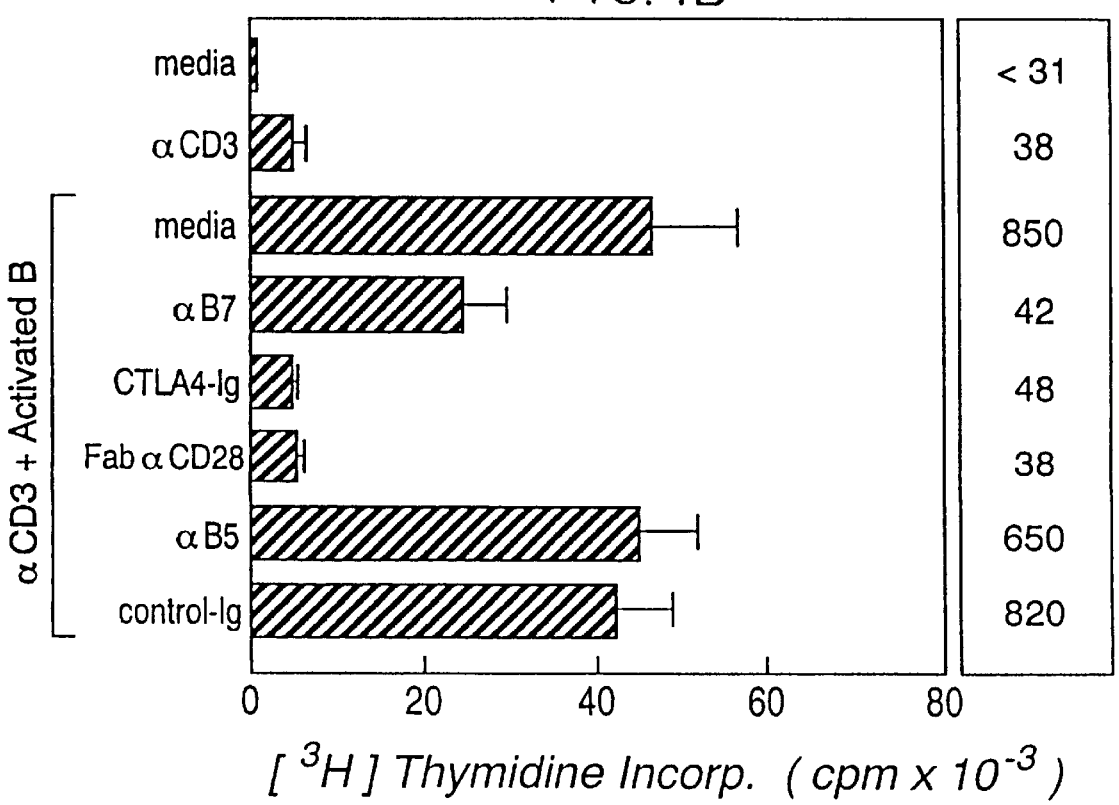

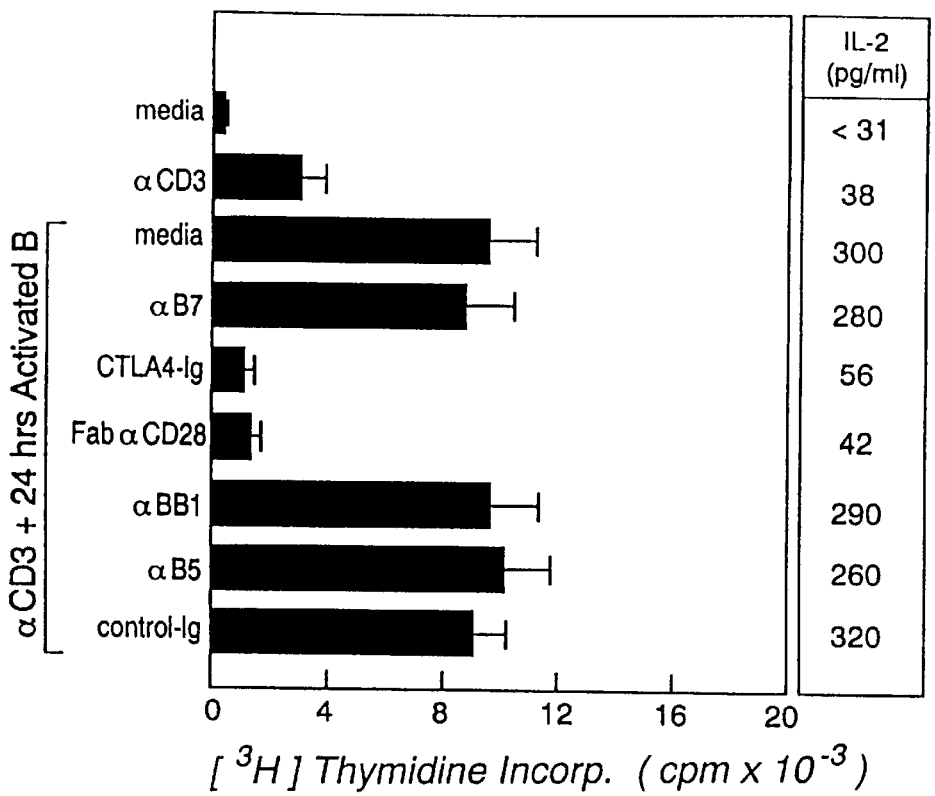
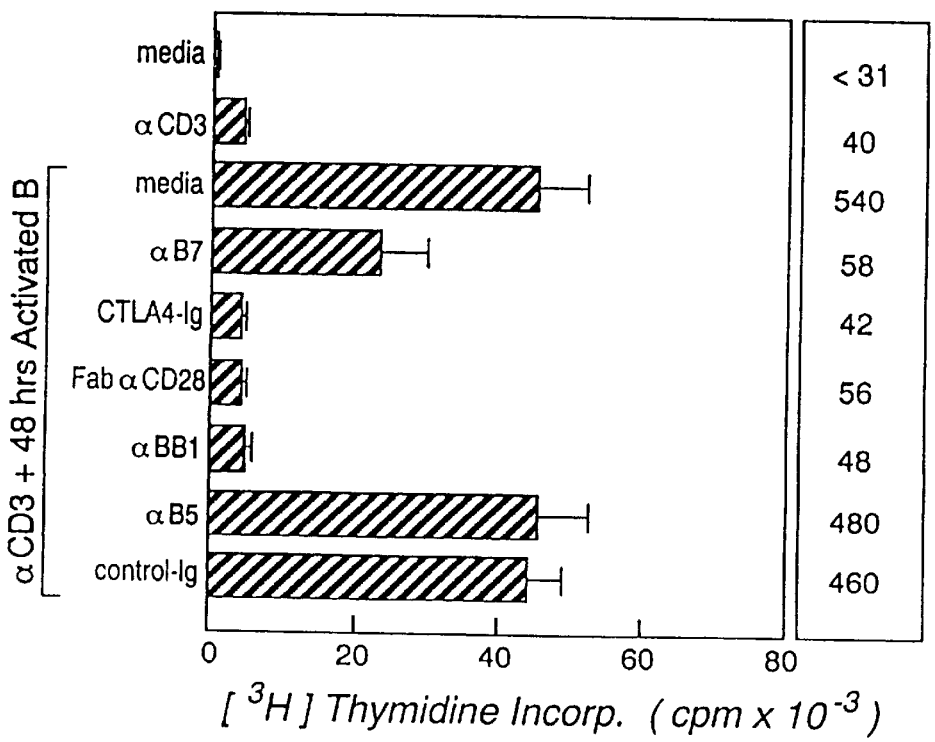

FIG. 8A

```
1    CACAGGGTGAAAGCTTTGCTTCTCTGCTGTAACAGGACTAGCACAGACACGGATGAGTGGGTC         70
71   ATTCCAGATATTAGGTCACAGCAGAGACAGCAGCCAAAATGGATCCCCAGTGCACTATGGGACTGAGTAACA  140
                                    M  D  P  Q  C  T  M  G  L  S  N          11
141  TTCTCTTGTGATGGCCCTTCCTCCTCTGGTGCTCCTCTGAAGATTCAAGCTTATTTCAATGAGAC        210
12   I  L  F  V  M  A  F  L  L  S  G  A  A  P  L  K  I  Q  A  Y  F  N  E  T   35
                                       ^                             #
211  TGCAGACCTGCCATGCCAATTGCAAACTCTCAAAACCAAGCCTGAGTGAGCTAGTAGTATTTTGGCAG     280
36   A  D  L  P  C  Q  F  A  N  S  Q  N  Q  S  L  S  E  L  V  V  F  W  Q      58
              *                    #
281  GACCAGGAAAACTGGTTCTGAATGAGGTATACTTAGGCAAAGAGAAATTTGACAGTGTTCATTCCAAGT   350
59   D  Q  E  N  L  V  L  N  E  V  Y  L  G  K  E  K  F  D  S  V  H  S  K      81
351  ATATGGGCCGCACAAGTTTTGATTCGGACAGTGGACCCTGAGACTTCACAATCTTCAGATCAAGGACAA   420
82   Y  M  G  R  T  S  F  D  S  D  S  W  T  L  R  L  H  N  L  Q  I  K  D  K  105
```

FIG. 8B

```
421  GGGCTTGTATCAATGTATCATCCATCACAAAAGCCCACAGGAATGATTCGCATCCACCAGATGAATTCT  490
106   G  L  Y  Q  C  I  I  H  H  K  K  P  T  G  M  I  R  I  H  Q  M  N  S   128
                    *

491  GAACTGTCAGTGCTTGCTAACTTCAGTCAACCTGAAATAGTACCAATTCTAATATAACAGAAAATGTGT  560
129   E  L  S  V  L  A  N  F  S  Q  P  E  I  V  P  I  S  N  I  T  E  N  V   151
                        #

561  ACATAAATTTGACCTGCTCATCTATACACGGTTACCCAGAACCTAAGAAGATGAGTGTTTGCTAAGAAC  630
152   Y  I  N  L  T  C  S  S  I  H  G  Y  P  E  P  K  K  M  S  V  L  L  R  T  175
            #         *

631  CAAGAATTCAACTATCGAGTATGATGGTATTATGCAGAAATCTCAAGATAATGTCACAGAACTGTACGAC  700
176   K  N  S  T  I  E  Y  D  G  I  M  Q  K  S  Q  D  N  V  T  E  L  Y  D   198
      #                                            #

701  GTTTCCATCAGCTTGTCTGTTCATTCCCTGATGTTACGAGCAATATGACCATCTTCTGTATTCTGGAAA  770
199   V  S  I  S  L  S  V  S  F  P  D  V  T  S  N  M  T  I  F  C  I  L  E   221
                                         #                    *

771  CTGACAAGACGGGCTTTATCTTCACCTTTCTCTATAGAGCTTGAGGACCCTCAGCCTCCCCCAGACCA  840
222   T  D  K  T  R  L  L  S  S  P  F  S  I  E  L  E  D  P  Q  P  P  P  D  H  245
```

FIG. 8C

```
841  CATTCCTTGGATTACAGCTGTACTTCCAACAGTTATTATATGTGTGATGGTTTTCTGTCTAATTCTATGG  910
246   I  P  W  I  T  A  V  L  P  T  V  I  I  C  V  M  V  F  C  L  I  L  K    268

911  AAATGGAAGAAGAAGCGGCCTGCAACTCTTATAAATGTGGAACCAACACAATGGAGAGGGAAGAGA       980
269   K  W  K  K  K  R  P  R  N  S  Y  K  C  G  T  N  M  E  R  E  E          291

981  GTGAACAGACCAAGAAAAAGAGAAAAAATCCATATACCTGAAAGATCTGATGAAGCCCAGCGTGTTTTAA  1050
292   S  E  Q  T  K  K  R  E  K  I  H  I  P  E  R  S  D  E  A  Q  R  V  F  K  315

1051 AAGTTCGAAGACATCTTCATGCGACAAAAGTGATACATGTTTTTAATTAAAGAGTAAAGCCCAAAAAAAA  1120
316   S  S  K  T  S  S  C  D  K  S  D  T  C  F  *                            329
```

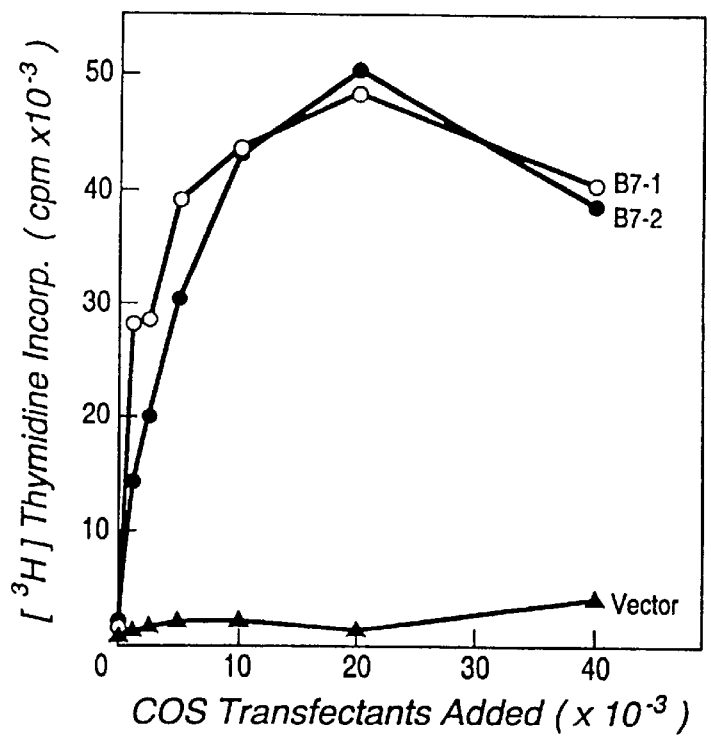
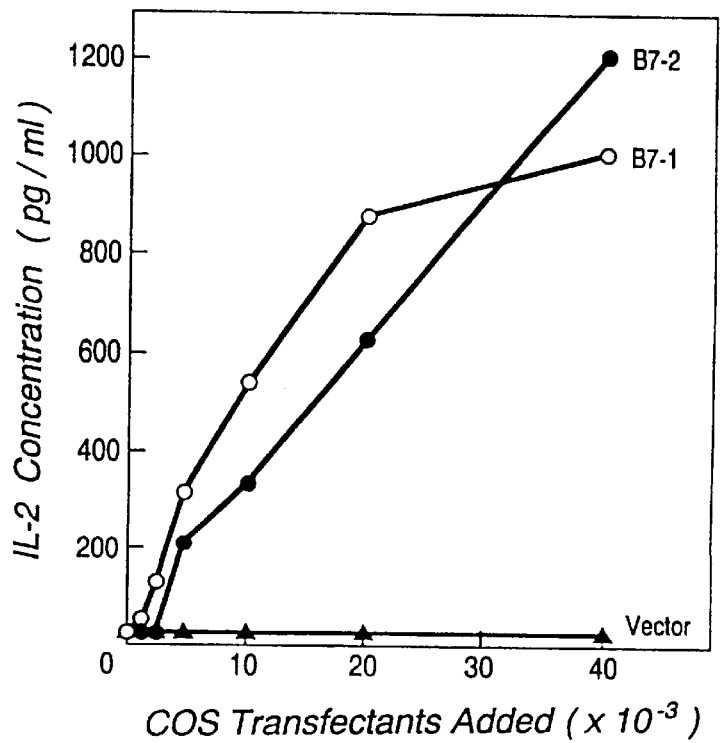

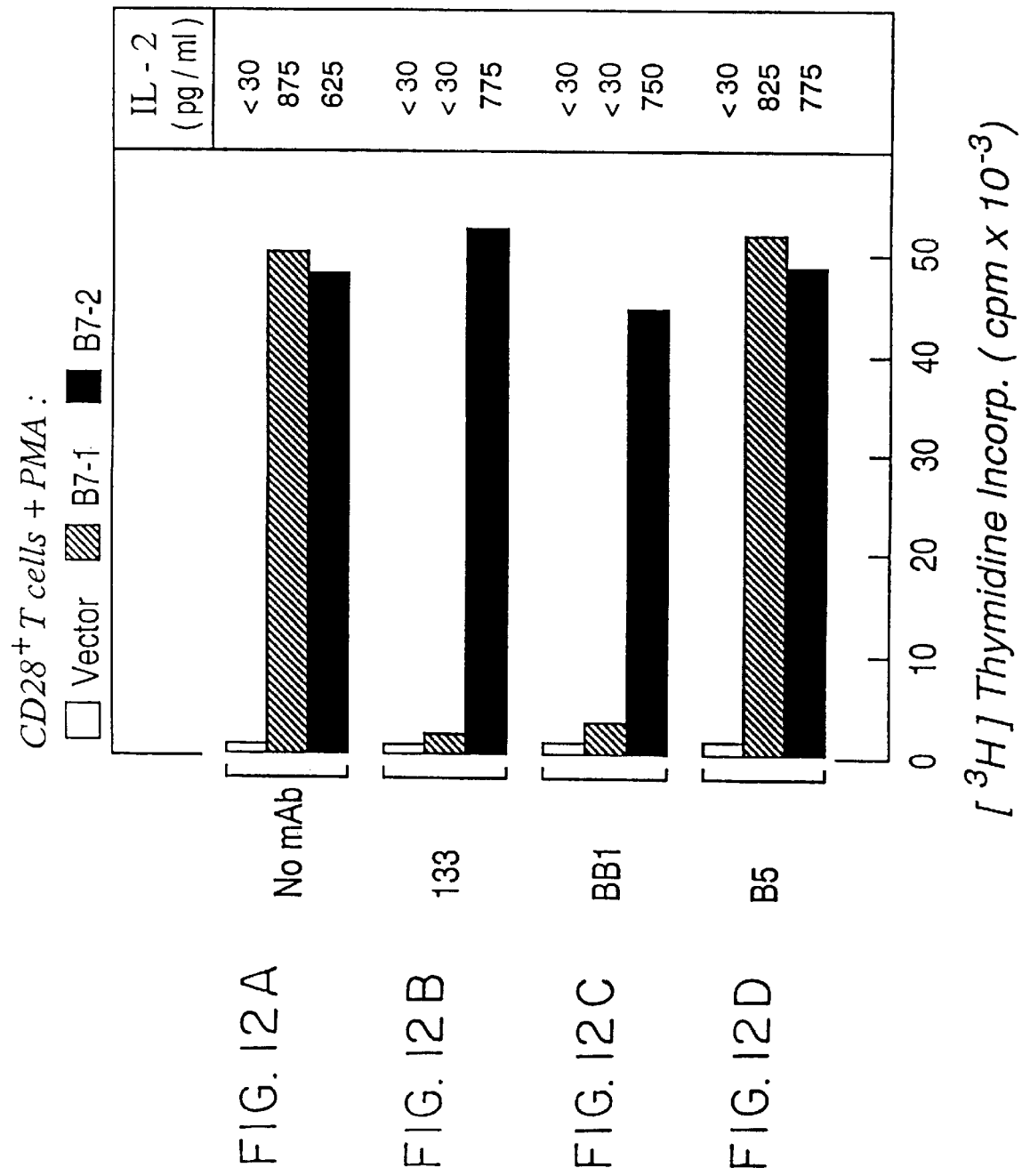

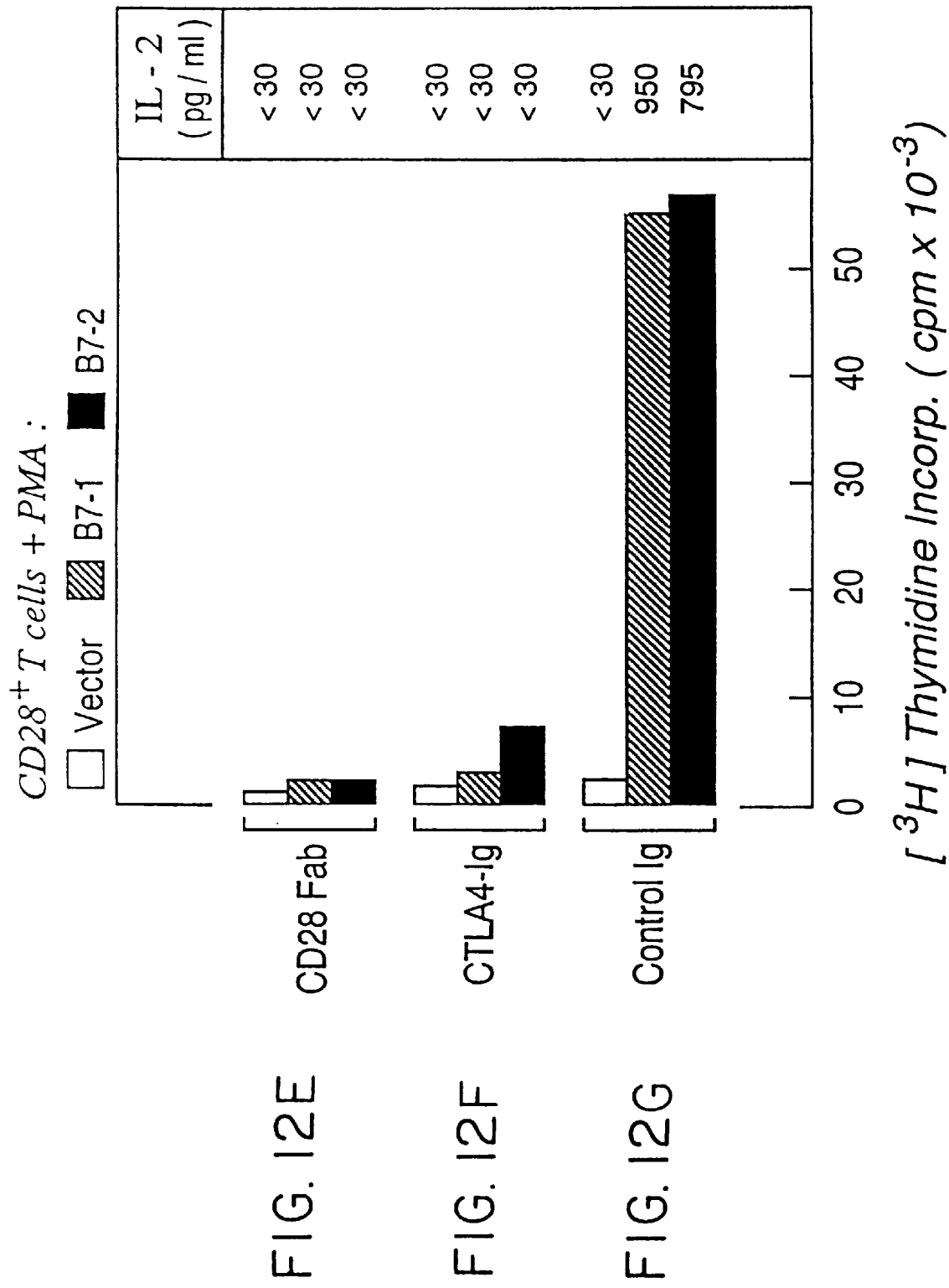

FIG. 13A

```
hB7-1    1 M..GHTRRQGTSPSKCPYLNFFQLLV.LAGLSHFCSGV.IHVTKEVKEVA       46
           |  |||                      |||  |
hB7-2    1 M......DPQCTMGLSN......ILFVMAFLLSGA...APLKIQAYFNETA      36
                                        ||  ||   |||
mB7      1 MACNCQLMQDTPLLKFPCPRLILFVLLIRLSQVSSDVDEQLSKSVKDKV       50 hB7-1   47 TLSCGHNVSVEE.LAQTRIYWQKEKKMVLT.MMSGDMNI...WPEYKNRT       91
           ||       ||   | |||||||   ||    |||        |||||||
hB7-2   37 DLPCQFANSQNQSLSELVVFWQDQENLVLNEVYLGKEKFDSVHSKYMGRT       86
                   |||                 ||  |             |||
mB7     51 LLPCRY.NSPHEDESEDRIYWQKHDKVVLS.VIAGKLKV...WPEYKNRT       95 hB7-1   92 IFDITNNLSIVILALRPSDEGTYECVVLKYEKDAFKREHLAEVTLSVKAD      141
           ||                    |
hB7-2   87 SFD.SDSWTLRLHNLQIKDKGLYQCIIHHKKPTGMIRIHQMNSELSVLAN      135
                                  |     |
mB7     96 LYDNTT.YSLIILGLVLSDRGTYSCVVQKKERGTYEVKHLALVKLSIKAD      144 hB7-1  142 FPTPSISDFEIPTSNI.RRIICSTSGGFPEPH.....LSWLENGEELNAIN     186
            | |                 ||||||||||
hB7-2  136 FSQPEIVPISNITENVYINLTCSSIHGYPEPKKMSVLLRTKNSTIEYDGI      185
            | |                  | | ||||
mB7    145 FSTPNITESGNPSADT.KRITCFASGGFPKPR....FSWLENGRELPGIN      189
```

FIG. 13B

```
hB7-1  187 TTVSQDPETELYAVSSKLDFN...MTTNHSFMCLIKYGHLRVNQTFNWNT 233
               ||| ||  ||| ||   |||||||||   ||   ||| |  |
hB7-2  186 MQKSQDNVTELYDVSISLSVSFPDVTSNMTIFCILETDKTRLLSSPFSIE 235
               ||| ||  ||| ||   |||||||||   ||   ||| |  |
mB7    190 TTISQDPESELYTISSQLDFN...TTRNHTIKCLIKYGDAHVSEDFTWEK 236
                     .         .         .         .         .

hB7-1  234 TKQEHF.PDNLLPSWAITLISVNGIFIVCCLTYCFAPRCRERRRNERLRR 282
                   |  |   |     |  |   ||| | | |
hB7-2  236 .LEDPQPPPDHIPWITAVLP....TVIICVMVFCLILWKKKRPRNSY   280
                   |  |   |     |  |   ||| | | |
mB7    237 PPEDPPPDSKNTLVLFGAGFGAVITVVVIVIIKCFCKHRSCFRRNEA.SR 285
                     .         .         .         .         .

hB7-1  283 ESVRPV*                                            288
                     .         .         .         .         .
hB7-2  281 KCG...TNTMEREESEQTKKREKIHIPERSDEAQRVFKSSKTSSCDKSDT 327
                     .         .         .         .         .
mB7    286 ETNNSLTFGPEEALAEQTVFL*                             306
                     .         .         .         .         .
hB7-2  328 CG*                                                329
```

FIG. 14A

```
     CCCACGCGTCCGGGAGCAAGCAGACGCGTAAGAGTGGCTCCTGTAGGCAGCACGGACTTG
1    ------+---------+---------+---------+---------+---------+  60
     GGGTGCGCAGGCCCCTCGTTCGTCTGCGCATTCTCACCGAGGACATCCGTCGTGCCTGAAC

AACAACCAGACTCCTGTAGACGTGTTCCAGAACTTACGGAAGCACCCACGATGGACCCCA
61   ------+---------+---------+---------+---------+---------+  120
     TTGTTGGTCTGAGGACATCTGCACAAGGTCTTGAATGCCTTCGTGGGTGCTACCTGGGGT
                                                        M  D  P  -

GATGCACCATGGGGCTTGGCAATCCTTATCTTTGTGACAGTTCTTCTGATCTCAGATGCTG
121  ------+---------+---------+---------+---------+---------+  180
     CTACGTGGTACCCGAACCGTTAGGAATAGAAACACTGTCAAGAAGACTAGAGTCTACGAC
      C  T  M  G  L  A  I  L  I  F  V  T  V  L  L  I  S  D  A  V -

TTTCCGTGGAGACGCAAGCTTATTCAATGGGACTGCATATCTGCCGTGCCCATTTACAA
181  ------+---------+---------+---------+---------+---------+  240
     AAAGGCACCTCTGCGTTCGAATAAGTTACCCTGACGTATAGACGGCACGGGTAAATGTT
      S  V  E  T  Q  A  Y  F  N  G  T  A  Y  L  P  C  P  F  T  K -

AGGCTCAAAACATAAGCCTGAGTGAGCTGGTAGTATTTTGGCAGGACCAGCAAAAGTTGG
241  ------+---------+---------+---------+---------+---------+  300
     TCCGAGTTTTGTATTCGGACTCACTCGACCATCATAAAACCGTCCTGGTCGTTTTCAACC
      A  Q  N  I  S  L  S  E  L  V  V  F  W  Q  D  Q  Q  K  L  V -
```

FIG. 14B

```
     TTCTGTACGAGCACTATTGGGCACAGAGAAACTGATAGTGTGAATGCCAAGTACCTGG
301  ------+---------+---------+---------+---------+---------+  360
     AAGACATGCTCGTGATAAACCCGTGTCTCTTTGAACTATCACACTTACGGTTCATGGACC

L   Y   E   H   Y   L   G   T   E   K   L   D   S   V   N   A   K   Y   L   G  -

GCCGCACGAGCTTTGACAGGAACAACTGGACTTCTACGACTTCACAATGTTCAGATCAAGG
361  ------+---------+---------+---------+---------+---------+  420
     CGGCGTGCTCGAAACTGTCCTTGTTGACCTGAAGATGCTGAAGTGTTACAAGTCTAGTTCC

R   T   S   F   D   R   N   N   W   T   L   R   L   H   N   V   Q   I   K   D  -

ACATGGGCTCGTATGATTGTTTTATACAAAAAGCCACCCACAGGATCAATTATCCTCC
421  ------+---------+---------+---------+---------+---------+  480
     TGTACCCGAGCATACTAACAAAATATGTTTTTTCGGTGGGTGTCCTAGTTAATAGGAGG

M   G   S   Y   D   C   F   I   Q   K   K   P   P   T   G   S   I   I   L   Q  -

AACAGAGACATTAACAGAACTGTCAGTGATCGCCAACTTCAGTGAACCTGAAATAAAACTGG
481  ------+---------+---------+---------+---------+---------+  540
     TTGTCTCTGTAATTGTCTTGACAGTCACTAGCGGTTGAAGTCACTTGGACTTTATTTTGACC

Q   T   L   T   E   L   S   V   I   A   N   F   S   E   P   E   I   K   L   A  -

CTCAGAATGTAACAGGAAATTCTGGCATAAATTTGACCTGCACGTCTAAGCAAGGTCACC
541  ------+---------+---------+---------+---------+---------+  600
     GAGTCTTACATTGTCCTTTAAGACCGTATTTAAACTGGACGTGCAGATTCGTTCCAGTGG

```
     CGAAACCTAAGAAGATGTATTTCTGATAATTCAACTAATGAGTATGGTGATAACA
601  ------+---------+---------+---------+---------+---------+  660
     GCTTTGGATTCTTCTACATAAAGACTATTAAGTTGATTACTCATACCACTATTGT

K  P  K  K  M  Y  F  L  I  T  N  S  T  N  E  Y  G  D  N  M  -

TGCAGATATCACAGATAATGTCACAGAACTGTTCAGTATCTCCAACAGCCTCTCTTT
661  ------+---------+---------+---------+---------+---------+  720
     ACGTCTATAGTGTCTATTACAGTGTCTTGACAAGTCATAGAGGTTGTCGGAGAGAAA

Q  I  S  Q  D  N  V  T  E  L  F  S  I  S  N  S  L  S  L  S  -

CATTCCCGGATGGTGTGGCATATGACCGTTGTGTGTTCTGGAAACGGAGTCAATGA
721  ------+---------+---------+---------+---------+---------+  780
     GTAAGGGCCTACCACACCGTATACTGGCAACACACAAGACCTTTGCCTCAGTTACT

F  P  D  G  V  W  H  M  T  V  V  C  V  L  E  T  E  S  M  K  -

AGATTTCCTCCAAACCCTCTCAATTCACTCAAGAGTTTCCATCTCCTCAAACGTATTGGA
781  ------+---------+---------+---------+---------+---------+  840
     TCTAAAGGAGGTTTGGGAGAGTTAAGTGAGTTCTCAAAGGTAGAGGAGTTTGCATAACCT

I  S  S  K  P  L  N  F  T  Q  E  F  P  S  P  Q  T  Y  W  K  -

AGGAGATTACAGCTTCAGTTACTGTGGCCCTCCTCCTTGTGATGCTGCTCATCATTGTAT
841  ------+---------+---------+---------+---------+---------+  900
     TCCTCTAATGTCGAAGTCAATGACACCGGGAGGAGGAACACTACGACGAGTAGTAACATA

```
901  GTCACAGAAGCCGAATCAGCTAGGCCCAGCAACACAGCCTCTAAGTTAGAGCGGG
     ------+---------+---------+---------+---------+---------+  960
     CAGTGTTCTTCGGCTTAGTCGATCGTCCGGGTCGTTGTGTCGGAGATTCAATCTCGCCC

H  K  K  P  N  Q  P  S  R  P  S  N  T  A  S  K  L  E  R  D  -

961  ATAGTAACGCTGACAGAGAGACTATCAACCTGAAGGAACTTGAACCCCAAATTGCTTCAG
     ------+---------+---------+---------+---------+---------+  1020
     TATCATTGCGACTGTCTCTCTGATAGTTGGACTTCCTTGAACTTGGGGTTTAACGAAGTC

S  N  A  D  R  E  T  I  N  L  K  E  L  E  P  Q  I  A  S  A  -

1021 CAAAACCAAATGCAGAGTGAAGGCAGTGAGAGCCTGAGGAAAGAGTTAAAAATTGCTTTG
     ------+---------+---------+---------+---------+---------+  1080
     GTTTTGGTTTACGTCTCACTTCCGTCACTCTCGGACTCCTTTCTCAATTTTTAACGAAAC

K  P  N  A  E  *

1081 CCTGAAATAAGAAGTGCAGAGTTTCTCAGAATTCAAAAATGTTCTCAGCTGATTGGAATT
     ------+---------+---------+---------+---------+---------+  1140
     GGACTTTATTCTTCACGTCTCAAAGAGTCTTAAGTTTTTACAAGAGTCGACTAACCTTAA

1141 CTACAGTTGAATAATTAAAGAAC
     ------+---------+--- 1163
     GATGTCAACTTATTAATTTCTTG
```

FUSION PROTEINS OF NOVEL CTLA4/CD28 LIGANDS AND USES THEREFORE

RELATED APPLICATIONS

This application is a continuation-in-part of U.S. Ser. No. 08/109,393, entitled "Novel CTLA4/CD28 Ligands and Uses Therefor" filed Aug. 19, 1993 (abandoned), which is a continuation-in-part of U.S. Ser. No. 08/101,624, also entitled "Novel CTLA4/CD28 Ligands and Uses Therefor", filed Jul. 26, 1993 (abandoned). This application is also a continuation-in-part of U.S. Ser. No. 08/147,773, entitled "Tumor Cells Modified To Express B7-2 And B7-3 With Increased Immunogenicity And Uses Therefor" filed Nov. 3, 1993 (abandoned). The contents of each of these applications is incorporated herein by reference.

GOVERNMENT FUNDING

Work described herein was supported under CA-40216-08 awarded by the National Institutes of Health. The U.S. government therefore may have certain rights in this invention.

BACKGROUND OF THE INVENTION

To induce antigen-specific T cell activation and clonal expansion, two signals provided by antigen-presenting cells (APCs) must be delivered to the surface of resting T lymphocytes (Jenkins, M. and Schwartz, R. (1987) *J. Exp. Med.* 165, 302–319; Mueller, D. L., et al. (1990) *J. Immunol.* 144, 3701–3709; Williams, I. R. and Unanue, E. R. (1990) *J. Immunol.* 145, 85–93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) *Science* 248, 1349–1356). Costimulation is neither antigen-specific, nor MHC restricted and is thought to be provided by one or more distinct cell surface molecules expressed by APCs (Jenkins, M. K., et al. (1988) *J. Immunol.* 140, 3324–3330; Linsley, P. S., et al. (1991) *J. Exp. Med* 173, 721–730; Gimmi, C. D., et al., (1991) *Proc. Natl. Acad. Sci. USA.* 88, 6575–6579; Young, J. W., et al. (1992) *J. Clin. Invest.* 90, 229–237; Koulova, L., et al. (1991) *J. Exp. Med* 173, 759–762; Reiser, H., et al. (1992) *Proc. Natl. Acad. Sci. USA.* 89, 271–275; van-Seventer, G. A., et al. (1990) *J. Immunol.* 144, 4579–4586; LaSalle, J. M., et al., (1991) *J. Immunol.* 147, 774–80; Dustin, M. I., et al., (1989) *J. Exp. Med.* 169, 503; Armitage, R. J., et al. (1992) *Nature* 357, 80–82; Liu, Y., et al. (1992) *J. Exp. Med.* 175, 437–445).

Considerable evidence suggests that the B7 protein, expressed on APCs, is one such critical costimulatory molecule (Linsley, P. S., et al., (1991) *J. Exp. Med.* 173, 721–730; Gimmi, C. D., et al., (1991) *Proc. Natl. Acad. Sci. USA.* 88, 6575–6579; Koulova, L., et al., (1991) *J. Exp. Med.* 173, 759–762; Reiser, H., et al. (1992) *Proc. Natl. Acad. Sci. USA.* 89, 271–275; Linsley, P. S. et al. (1990) *Proc. Natl. Acad. Sci. USA.* 87, 5031–5035; Freeman, G. J. et al. (1991) *J. Exp. Med.* 174, 625–631.). B7 is the counter-receptor for two ligands expressed on T lymphocytes. The first ligand, termed CD28, is constitutively expressed on resting T cells and increases after activation. After signaling through the T cell receptor, ligation of CD28 induces T cells to proliferate and secrete IL-2 (Linsley, P. S., et al. (1991) *J. Exp. Med.* 173, 721–730; Gimmi, C. D., et al. (1991) *Proc. Natl. Acad. Sci. USA.* 88, 6575–6579; Thompson, C. B., et al. (1989) *Proc. Natl. Acad. Sci. USA.* 86, 1333–1337; June, C. H., et al. (1990) *Immunol. Today.* 11, 211–6; Harding, F. A., et al. (1992) *Nature.* 356, 607–609.). The second ligand, termed CTLA4 is homologous to CD28 but is not expressed on resting T cells and appears following T cell activation (Brunet, J. F., et al., (1987) *Nature* 328, 267–270). DNA sequences encoding the human and murine CTLA4 protein are described in Dariavich, et al. (1988) *Eur. J. Immunol.* 18(12), 1901–1905; Brunet, J. F., et al. (1987) supra; Brunet, J. F. et al. (1988) *Immunol. Rev.* 103:21–36; and Freeman, G. J., et al. (1992) *J. ImmunoL* 149, 3795–3801. Although B7 has a higher affinity for CTLA4 than for CD28 (Linsley, P. S., et al., (1991) *J. Exp. Med.* 174, 561–569), the function of CTLA4 is still unknown.

The importance of the B7:CD28/CTLA4 costimulatory pathway has been demonstrated in vitro and in several in vivo model systems. Blockade of this costimulatory pathway results in the development of antigen specific tolerance in murine and humans systems (Harding, F. A., et al. (1992) *Nature.* 356, 607–609; Lenschow, D. J., et al. (1992) *Science.* 257, 789–792; Turka, L. A., et al. (1992) *Proc. Natl. Acad. Sci. USA.* 89, 11102–11105; Gimmi, C. D., et al. (1993) *Proc. Natl. Acad. Sci USA* 90, 6586–6590; Boussiotis, V., et al. (1993) *J. Exp. Med.* 178, 1753–1763). Conversely, expression of B7 by B7 negative murine tumor cells induces T-cell mediated specific immunity accompanied by tumor rejection and long lasting protection to tumor challenge (Chen, L., et al. (1992) *Cell* 71, 1093–1102; Townsend, S. E. and Allison, J. P. (1993) *Science* 259, 368–370; Baskar, S., et al. (1993) *Proc. Natl. Acad Sci.* 90, 5687–5690.). Therefore, manipulation of the B7:CD28/CTLA4 pathway offers great potential to stimulate or suppress immune responses in humans.

SUMMARY OF THE INVENTION

This invention pertains to isolated nucleic acids encoding novel molecules which costimulate T cell activation. Preferred costimulatory molecules include antigens on the surface of B lymphocytes, professional antigen presenting cells (e.g., monocytes, dendritic cells, Langerhan cells) and other cells (e.g., keratinocytes, endothelial cells, astrocytes, fibroblasts, oligodendrocytes) which present antigen to immune cells, and which bind either CTLA4, CD28, both CTLA4 and CD28 or other known or as yet undefined receptors on immune cells. Such costimulatory molecules are referred to herein as CTLA4/CD28 binding counter-receptors or B lymphocyte antigens, and are capable of providing costimulation to activated T cells to thereby induce T cell proliferation and/or cytokine secretion. Preferred B lymphocyte antigens include B7-2 and B7-3 and soluble fragments or derivatives thereof which bind CTLA4 and/or CD28 and have the ability to inhibit or induce costimulation of immune cells. In one embodiment, an isolated nucleic acid which encodes a peptide having the activity of the human B7-2 B lymphocyte antigen is provided. Preferably, the nucleic acid is a cDNA molecule having a nucleotide sequence encoding human B7-2, as shown in FIG. 8 (SEQ ID NO:1). In another embodiment, the nucleic acid is a cDNA molecule having a nucleotide sequence encoding murine B7-2, as shown in FIG. 14 (SEQ ID NO:22).

The invention also features nucleic acids which encode a peptide having B7-2 activity and at least about 50%, more preferably at least about 60% and most preferably at least about 70% homologous with an amino acid sequence shown in FIG. 8 (SEQ ID NO:2) or an amino acid sequence shown in FIG. 14 (SEQ ID NO:23). Nucleic acids which encode peptides having B7-2 activity and at least about 80%, more preferably at least about 90%, more preferably at least about 95% and most preferably at least about 98% or at least about 99% homologous with an amino acid sequence shown in FIG. 8 (SEQ ID NO:2) or an amino acid sequence shown in FIG. 14 (SEQ ID NO:23) are also within the scope of the invention. In another embodiment, the peptide having B7-2 activity is encoded by a nucleic acid which hybridizes under high or low stringency conditions to a nucleic acid which encodes a peptide having an amino acid sequence of FIG. 8 (SEQ ID NO:2) or a peptide having an amino acid sequence shown in FIG. 14 (SEQ ID NO:23).

The invention further pertains to an isolated nucleic acid comprising a nucleotide sequence encoding a peptide having B7-2 activity and having a length of at least 20 amino acid residues. Peptides having B7-2 activity and consisting of at least 40 amino acid residues in length, at least 60 amino acid residues in length, at least 80 amino acid residues in length, at least 100 amino acid residues in length or at least 200 or more amino acid residues in length are also within the scope of this invention. Particularly preferred nucleic acids encode a peptide having B7-2 activity, a length of at least 20 amino acid residues or more and at least 50% or greater homology (preferably at least 70%) with a sequence shown in FIG. 8 (SEQ ID NO:2).

In one preferred embodiment, the invention features an isolated DNA encoding a peptide having B7-2 activity and an amino acid sequence represented by a formula:

$$X_n\text{-}Y\text{—}Z_m$$

In the formula, Y consists essentially of amino acid residues 24–245 of the sequence shown in FIG. 8 (SEQ ID NO:2). $X_n$ and $Z_m$ are additional amino acid residue(s) linked to Y by an amide bond. $X_n$ and $Z_m$ are amino acid residues selected from amino acid residues contiguous to Y in the amino acid sequence shown in FIG. 8 (SEQ ID NO:2). $X_n$ is amino acid residue(s) selected from amino acids contiguous to the amino terminus of Y in the sequence shown in FIG. 8 (SEQ ID NO:2), i.e., selected from amino acid residue 23 to 1. $Z_m$ is amino acid residue(s) selected from amino acids contiguous to the carboxy terminus of Y in the sequence shown in FIG. 8 (SEQ ID NO:2), i.e., selected from amino acid residue 246 to 329. According to the formula, n is a number from 0 to 23 (n=0–23) and m is a number from 0 to 84 (m=0–84). A particularly preferred DNA encodes a peptide having an amino acid sequence represented by the formula $X_n\text{-}Y\text{—}Z_m$, where Y is amino acid residues 24–245 of the sequence shown in FIG. 8 (SEQ ID NO:2) and n=0 and m=0.

The invention also features an isolated DNA encoding a B7-2 fusion protein which includes a nucleotide sequence encoding a first peptide having B7-2 activity and a nucleotide sequence encoding a second peptide corresponding to a moiety that alters the solubility, binding affinity, stability or valency of the first peptide. Preferably, the first peptide having B7-2 activity includes an extracellular domain portion of the B7-2 protein (e.g., about amino acid residues 24–245 of the sequence shown in FIG. 8 (SEQ ID NO:2)) and the second peptide is an immunoglobulin constant region, for example, a human Cγ1 or Cγ4 domain, including the hinge, CH2 and CH3 region, to produce a B7-2 immunoglobulin fusion protein (B7-2Ig) (see Capon et al. (1989) Nature 337, 525–531 and Capon U.S. Pat. No. 5,116,964).

The nucleic acids obtained in accordance with the present invention can be inserted into various expression vectors, which in turn direct the synthesis of the corresponding protein or peptides in a variety of hosts, particularly eucaryotic cells, such as mammalian and insect cell culture, and procaryotic cells such as E. coli. Expression vectors within the scope of the invention comprise a nucleic acid encoding at least one peptide having the activity of a novel B lymphocyte antigen as described herein, and a promoter operably linked to the nucleic acid sequence. In one embodiment, the expression vector contains a DNA encoding a peptide having the activity of the B7-2 antigen and a DNA encoding a peptide having the activity of another B lymphocyte antigen, such as the previously characterized B7 activation antigen, referred to herein as B7-1. Such expression vectors can be used to transfect host cells to thereby produce proteins and peptides, including fusion proteins, encoded by nucleic acids as described herein.

Nucleic acid probes useful for assaying a biological sample for the presence of B cells expressing the B lymphocyte antigens B7-2 and B7-3 are also within the scope of the invention.

The invention further pertains to isolated peptides having the activity of a novel B lymphocyte antigen, including the B7-2 and B7-3 protein antigens. A preferred peptide having B7-2 activity is produced by recombinant expression and comprises an amino acid sequence shown in FIG. 8 (SEQ ID NO:2). Another preferred peptide having B7-2 activity comprises an amino acid sequence shown in FIG. 14 (SEQ ID NO:23). A particularly preferred peptide having the activity of the B7-2 antigen includes at least a portion of the mature form of the protein, such as an extracellular domain portion (e.g., about amino acid residues 24–245 of SEQ ID NO:2) which can be used to enhance or suppress T-cell mediated immune responses in a subject. Other preferred peptides having B7-2 activity include peptides having an amino acid sequence represented by a formula:

$$X_n\text{-}Y\text{-}Z_m$$

In the formula, Y is amino acid residues selected from the group consisting of: amino acid residues 55–68 of the sequence shown in FIG. 8 (SEQ ID NO:2); amino acid residues 81–89 of the sequence shown in FIG. 8 (SEQ ID NO:2); amino acid residues 128–142 of the sequence shown in FIG. 8 (SEQ ID NO:2); amino acid residues 160–169 of the sequence shown in FIG. 8 (SEQ ID NO:2); amino acid residues 188–200 of the sequence shown in FIG. 8 (SEQ ID NO:2); and amino acid residues 269–282 of the sequence shown in FIG. 8 (SEQ ID NO:2). In the formula $X_n$ and $Z_m$ are additional amino acid residue(s) linked to Y by an amide bond and are selected from amino acid residues contiguous to Y in the amino acid sequence shown in FIG. 8 (SEQ ID NO:2). $X_n$ is amino acid residue(s) selected from amino acids contiguous to the amino terminus of Y in the sequence shown in FIG. 8 (SEQ ID NO:2). $Z_m$ is amino acid residue(s) selected from amino acids contiguous to the carboxy terminus of Y in the sequence shown in FIG. 8 (SEQ ID NO:2). According to the formula, n is a number from 0 to 30 (n=0–30) and m is a number from 0 to 30 (m=0–30).

Fusion proteins or hybrid fusion proteins including a peptide having the activity of a novel B lymphocyte antigen (e.g., B7-2, B7-3) are also featured. For example, a fusion protein comprising a first peptide which includes an extracellular domain portion of a novel B lymphocyte antigen fused to second peptide, such as an immunoglobulin constant region, that alters the solubility, binding affinity, stability and/or valency of the first peptide are provided. In one embodiment, a fusion protein is produced comprising a first peptide which includes amino acid residues of an extracellular domain portion of the B7-2 protein joined to a second peptide which includes amino acid residues of a sequence corresponding to the hinge, CH2 and CH3 regions of Cγ1 or Cγ4 to form a B7-2Ig fusion protein. In another embodiment, a hybrid fusion protein is produced comprising a first peptide which includes an extracellular domain portion of the B7-1 antigen and an extracellular domain portion of the B7-2 antigen and a second peptide which includes amino acid residues corresponding to the hinge, CH2 and CH3 of Cγ1 (see e.g., Linsley et al. (1991) *J. Exp. Med.* 1783:721–730; Capon et al. (1989) *Nature* 337, 525–531; and Capon U.S. Pat. No. 5,116,964).

Isolated peptides and fusion proteins of the invention can be administered to a subject to either upregulate or inhibit the expression of one or more B lymphocyte antigens or block the ligation of one or more B lymphocyte antigens to their natural ligand on immune cells, such as T cells, to thereby provide enhancement or suppression of cell-mediated immune responses in vivo.

Another embodiment of the invention provides antibodies, preferably monoclonal antibodies, specifically reactive with a peptide of a novel B lymphocyte antigen or fusion protein as described herein. Preferred antibodies are anti-human B7-2 monoclonal antibodies produced by hybridoma cells HF2.3D1, HA5.2B7 and HA3.1F9. These hybridoma cells have been deposited with the American Type Culture Collection at ATCC Accession No. HB 11686 (HF2.3D1), ATCC Accession No. HB 11687 (HA5.2B7), and ATCC Accession No. HB 11688.

A still further aspect of the invention involves the use of the nucleic acids of the invention, especially the cDNAs, to enhance the immunogenicity of a mammalian cell. In preferred embodiments, the mammalian cell is a tumor cell, such as a sarcoma, a lymphoma, a melanoma, a neuroblastoma, a leukemia or a carcinoma, or an antigen presenting cell, such as a macrophage, which is transfected to allow expression of a peptide having the activity of a novel B lymphocyte antigen of the invention on the surface of the cell. Macrophages that express a peptide having the activity of a B lymphocyte antigen, such as the B7-2 antigen, can be used as antigen presenting cells, which, when pulsed with an appropriate pathogen-related antigen or tumor antigen, enhance T cell activation and immune stimulation.

Mammalian cells can be transfected with a suitable expression vector containing a nucleic acid encoding a peptide having the activity of a novel B lymphocyte antigen, such as the B7-2 antigen, ex vivo and then introduced into the host mammal, or alternatively, cells can be transfected with the gene in vivo via gene therapy techniques. For example, the nucleic acid encoding a peptide having B7-2 activity can be transfected alone, or in combination with nucleic acids encoding other costimulatory molecules. In enhancing the immunogenicity of tumors which do not express Class I or Class II MHC molecules, it may be beneficial to additionally transfect appropriate class I or II genes into the mammalian cells to be transfected with a nucleic acid encoding a peptide having the activity of a B lymphocyte antigen, as described herein.

The invention also provides methods for inducing both general immunosuppression and antigen-specific tolerance in a subject by, for example, blocking the functional interaction of the novel B lymphocyte antigens of the invention, e.g., B7-2 and B7-3, to their natural ligand(s) on T cells or other immune system cells, to thereby block co-stimulation through the receptor-ligand pair. In one embodiment, inhibitory molecules that can be used to block the interaction of the natural human B7-2 antigen to its natural ligands (e.g., CTLA4 and CD28) include a soluble peptide having B7-2 binding activity but lacking the ability to costimulate immune cells, antibodies that block the binding of B7-2 to its ligands and fail to deliver a co-stimulatory signal (so called "blocking antibodies", such as blocking anti-B7-2 antibodies), B7-2-Ig fusion proteins, which can be produced in accordance with the teachings of the present invention, as well as soluble forms of B7-2 receptors, such as CTLA4Ig or CD28Ig. Such blocking agents can be used alone or in combination with agents which block interaction of other costimulatory molecules with their natural ligands (e.g., anti-B7 antibody). Inhibition of T cell responses and induction of T cell tolerance according to the methods described herein may be useful prophylactically, in preventing transplantation rejection (solid organ, skin and bone marrow) and graft versus host disease, especially in allogeneic bone marrow transplantation. The methods of the invention may also be useful therapeutically, in the treatment of autoimmune diseases, allergy and allergic reactions, transplantation rejection, and established graft versus host disease in a subject.

Another aspect of the invention features methods for upregulating immune responses by delivery of a costimulatory signal to T cells through use of a stimulatory form of B7-2 antigen, which include soluble, multivalent forms of B7-2 protein, such as a peptide having B7-2 activity and B7-2 fusion proteins. Delivery of a stimulatory form of B7-2 in conjunction with antigen may be useful prophylactically to enhance the efficacy of vaccination against a variety of pathogens and may also be useful therapeutically to upregulate an immune response against a particular pathogen during an infection or against a tumor in a tumor-bearing host.

The invention also features methods of identifying molecules which can inhibit either the interaction of B lymphocyte antigens, e.g., B7-2, B7-3, with their receptors or interfere with intracellular signalling through their receptors. Methods for identifying molecules which can modulate the expression of B lymphocyte antigens on cells are also provided. In addition, methods for identifying cytokines produced in response to costimulation of T cells by novel B lymphocyte antigens are within the scope of the invention.

BRIEF DESCRIPTION OF THE DRAWINGS

FIGS. 1A–B are graphic representations of the responses of $CD28^+$ T cells, as assessed by $^3$H-thymidine incorporation or IL-2 secretion, to costimulation provided by either B7 (B7-1) transfected CHO cells (panel a) or syngeneic activated B lymphocytes (panel b) cultured in media, anti-CD3 alone, or anti-CD3 in the presence of the following monoclonal antibodies or recombinant proteins: αB7 (133, anti-B7-1); CTLA4Ig; Fab αCD28; control Ig fusion protein (isotype control for CTLA4Ig); or αCB5 (anti-B5, the isotype control for anti-B7-1).

FIGS. 7A–B are graphic representations of the response of CD28$^+$ T cells, as assessed by $^3$H-thymidine incorporation and IL-2 secretion, to costimulation provided by syngeneic B lymphocytes activated by sIg crosslinking for 24 hours (panel a) or 48 hours (panel b) and cultured in media, anti-CD3 alone, or anti-CD3 in the presence of the following monoclonal antibodies or recombinant protein: αB7(133, anti-B7-1); αBB1 (anti-B7-1, anti-B7-3) CTLA4Ig; Fab αCD28; and αB5(anti-B5).

FIG. 8 is the nucleotide and deduced amino acid sequence of the human B lymphocyte antigen B7-2 (hB7-2-clone29).

FIG. 11 is a graphic representation of the proliferation of CD28+ T cells, as assessed by $^3$H-thymidine incorporation or IL-2 secretion, to submitogenic stimulation with phorbol myristic acid (PMA) and COS cells transfected with vector alone or vectors directing the expression of either B7-1 or B7-2.

FIG. 12 is a graphic representation of the inhibition by mAbs and recombinant proteins of the proliferation of CD28+ T cells, as assessed by $^3$H-thymidine incorporation and IL-2 secretion, to stimulation by PMA and COS cells transfected with vector alone (vector), or with a vector expressing B7-1 (B7-1) or B7-2 (B7-2). Inhibition studies were performed with the addition of either no antibody (no mAb), anti-B7 mab 133 (133), anti-B7 mAb BB-1 (BB1), anti-B5 mAb (B5), Fab fragment of anti-CD28 (CD28 Fab), CTLA4Ig (CTLA4Ig), or Ig control protein (control Ig) to the PMA stimulated COS cell admixed CD28$^+$ T cells.

FIG. 13 shows the sequence homology between the human B7-2 protein (h B7-2) deduced amino acid sequence (SEQ ID NO:2) and the amino acid sequence of both the human B7-1 protein (h B7-1) (SEQ ID NO:28 and 29) and the murine B7-1 protein (m B7) (SEQ ID NO:30 and 31).

FIG. 14 is the nucleotide and deduced amino acid sequence of the murine B7-2 antigen (mB7-2) (SEQ ID NO:22 and 23).

DETAILED DESCRIPTION OF THE INVENTION

Figure 2A:
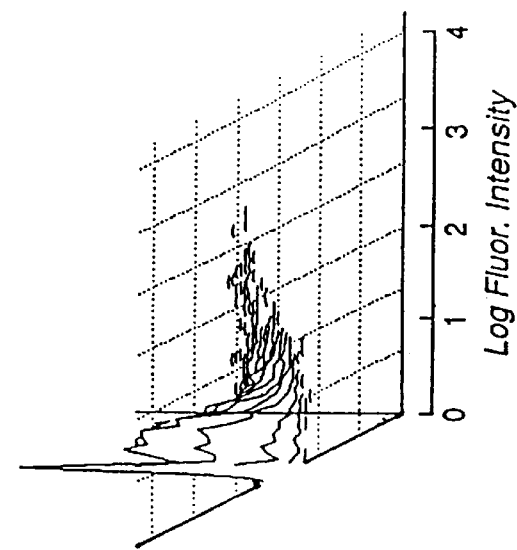
FIGS. 2A–C are graphs of log fluorescence intensity of cell surface expression of B7-1 on splenic B cells activated with surface immunoglobulin (sIg) crosslinking. The total (panel a), B7-1 positive ($B7-1^+$, panel b) and $B7-1^-$ negative (B7-1-, panel c) activated B cells were stained with anti-B7-1 monoclonal antibody (133) and fluoroscein isothiocyanate (FITC) labeled goat anti-mouse immunoglobulin and analyzed by flow cytometry.

In addition to the previously characterized B lymphocyte activation antigen B7 (referred to herein as B7-1), human B lymphocytes express other novel molecules which costimulate T cell activation. These costimulatory molecules include antigens on the surface of B lymphocytes, professional antigen presenting cells (e.g., monocytes, dendritic cells, Langerhan cells) and other cells (e.g., keratinocytes, endothelial cells, astrocytes, fibroblasts, oligodendrocytes) which present antigen to immune cells, and which bind either CTLA4, CD28, both CTLA4 and CD28 or other known or as yet undefined receptors on immune cells. Costimulatory molecules within the scope of the invention are referred to herein as CTLA4/CD28 ligands (counter-receptors) or B lymphocyte antigens. Novel B lymphocyte antigens which provide costimulation to activated T cells to thereby induce T cell proliferation and/or cytokine secretion include the B7-2 (human and murine) and the B7-3 antigens described and characterized herein.

The B lymphocyte antigen B7-2 is expressed by human B cells at about 24 hours following stimulation with either anti-immunoglobulin or anti-MHC class II monoclonal antibody. The B7-2 antigen induces detectable IL-2 secretion and T cell proliferation. At about 48 to 72 hours post activation, human B cells express both B7-1 and a third CTLA4 counter-receptor, B7-3, identified by a monoclonal antibody BB-1, which also binds B7-1 (Yokochi, T., et al. (1982) *J. Immunol.* 128, 823–827). The B7-3 antigen is also expressed on B7-1 negative activated B cells and can costimulate T cell proliferation without detectable IL-2 production, indicating that the B7-1 and B7-3 molecules are distinct. B7-3 is expressed on a wide variety of cells including activated B cells, activated monocytes, dendritic cells, Langerhan cells and keratinocytes. At 72 hours post B cell activation, the expression of B7-1 and B7-3 begins to decline. The presence of these costimulatory molecules on the surface of activated B lymphocytes indicates that T cell costimulation is regulated, in part, by the temporal expression of these molecules following B cell activation.

Accordingly, one aspect of this invention pertains to isolated nucleic acids comprising a nucleotide sequence encoding a novel costimulatory molecule, such as the B lymphocyte antigen, B7-2, fragments of such nucleic acids, or equivalents thereof. The term "nucleic acid" as used herein is intended to include such fragments or equivalents. The term "equivalent" is intended to include nucleotide sequences encoding functionally equivalent B lymphocyte antigens or functionally equivalent peptides having an activity of a novel B lymphocyte antigen, i.e., the ability to bind to the natural ligand(s) of the B lymphocyte antigen on immune cells, such as CTLA4 and/or CD28 on T cells, and inhibit (e.g., block) or stimulate (e.g., enhance) immune cell costimulation. Such nucleic acids are considered equivalents of the human B7-2 nucleotide sequence provided in FIG. 8 (SEQ ID NO:1) and the murine B7-2 nucleotide sequence provided in FIG. 14 (SEQ ID NO:22) and are within the scope of this invention.

In one embodiment, the nucleic acid is a cDNA encoding a peptide having an activity of the B7-2 B lymphocyte antigen. Preferably, the nucleic acid is a cDNA molecule consisting of at least a portion of a nucleotide sequence encoding human B7-2, as shown in FIG. 8 (SEQ ID NO:1) or at least a portion of a nucleotide sequence encoding murine B7-2, as shown in FIG. 14 (SEQ ID NO:22). A preferred portion of the cDNA molecule of FIG. 8 (SEQ ID NO:1) or FIG. 14 (SEQ ID NO:22) includes the coding region of the molecule.

In another embodiment, the nucleic acid of the invention encodes a peptide having an activity of B7-2 and comprising an amino acid sequence shown in FIG. 8 (SEQ ID NO:2) or FIG. 14 (SEQ ID NO:23). Preferred nucleic acids encode a peptide having B7-2 activity and at least about 50% homology, more preferably at least about 60% homology and most preferably at least about 70% homology with an amino acid sequence shown in FIG. 8 (SEQ ID NO:2). Nucleic acids which encode peptides having B7-2 activity and at least about 90%, more preferably at least about 95%, and most preferably at least about 98–99% homologous with a sequence set forth in FIG. 8 (SEQ ID NO:2) are also within the scope of the invention. Homology refers to sequence similarity between two peptides having the activity of a novel B lymphocyte antigen, such as B7-2, or between two nucleic acid molecules. Homology can be determined by comparing a position in each sequence which may be aligned for purposes of comparison. When a position in the compared sequences is occupied by the same nucleotide base or amino acid, then the molecules are homologous at that position. A degree (or percentage) of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in FIG. 8 (SEQ ID NO:2) or a peptide having all or a portion of an amino acid sequence shown in FIG. 14 (SEQ ID NO:23). Appropriate stringency conditions which promote DNA hybridization, for example, 6.0× sodium chloride/sodium citrate (SSC) at about 45° C., followed by a wash of 2.0× SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C.. In addition, the temperature in the wash step can be increased from low stringency conditions at room temperature, about 22° C. to high stringency conditions, at about 65° C..

Isolated nucleic acids encoding a peptide having an activity of a novel B lymphocyte antigen, as described herein, and having a sequence which differs from nucleotide sequence shown in FIG. 8 (SEQ ID NO:1) or FIG. 14 (SEQ ID NO:22) due to degeneracy in the genetic code are also within the scope of the invention. Such nucleic acids encode functionally equivalent peptides (e.g., a peptide having B7-2 activity) but differ in sequence from the sequence of FIG. 8 or FIG. 14 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of a B7-2 (especially those within the third base of a codon) may result in "silent" mutations in the DNA which do not affect the amino acid encoded. However, it is expected that DNA sequence polymorphisms that do lead to changes in the amino acid sequences of the B7-2 antigen will exist within a population. It will be appreciated by one skilled in the art that these variations in one or more nucleotides (up to about 3–4% of the nucleotides) of the nucleic acids encoding peptides having the activity of a novel B lymphocyte antigen may exist among individuals within a population due to natural allelic variation. Any and all such nucleotide variations and resulting amino acid polymorphisms are within the scope of the invention. Furthermore, there may be one or more isoforms or related, cross-reacting family members of the novel B lymphocyte antigens described herein. Such isoforms or family members are defined as proteins related in function and amino acid sequence to a B lymphocyte antigen (e.g., the B7-2 antigen), but encoded by genes at different loci.

A "fragment" of a nucleic acid encoding a novel B lymphocyte antigen is defined as a nucleotide sequence having fewer nucleotides than the nucleotide sequence encoding the entire amino acid sequence of the B lymphocyte antigen and which encodes a peptide having an activity of the B lymphocyte antigen (i.e., the ability to bind to the natural ligand(s) of the B lymphocyte antigen on immune cells, such as CTLA4 and/or CD28 on T cells and either stimulate or inhibit immune cell costimulation). Thus, a peptide having B7-2 activity binds CTLA4 and/or CD28 and stimulates or inhibits a T cell mediated immune response, as evidenced by, for example, cytokine production and/or T cell proliferation by T cells that have received a primary activation signal. In one embodiment, the nucleic acid fragment encodes a peptide of the B7-2 antigen which retains the ability of the antigen to bind CTLA4 and/or CD28 and deliver a costimulatory signal to T lymphocytes. In another embodiment, the nucleic acid fragment encodes a peptide including an extracellular portion of the human B7-2 antigen (e.g., approximately amino acid residues 24–245 of the sequence provided in FIG. 8 (SEQ ID NO:2)) which can be used to bind CTLA4 and/or CD28 and, in monovalent form, inhibit costimulation, or in multivalent form, induce or enhance costimulation.

Preferred nucleic acid fragments encode peptides of at least 20 amino acid residues in length, preferably at least 40 amino acid residues and length, and more preferably at least 60 amino acid residues in length. Nucleic acid fragments which encode peptides of at least 80 amino acid residues in length, at least 100 amino acid residues in length, and at least 200 or more amino acids in length are also within the scope of the invention. Particularly preferred nucleic acid fragments encode a peptide having the activity of human B7-2 and an amino acid sequence represented by a formula:

$$X_n-Y-Z_m$$

In the formula, Y comprises amino acid residues 24–245 of the sequence shown in FIG. 8 (SEQ ID NO:2). $X_n$ and $Z_m$ are additional amino acid residue(s) linked to Y by an amide bond. $X_n$ and $Z_m$ are selected from amino acid residues contiguous to Y in the amino acid sequence shown in FIG. 8 (SEQ ID NO:2). In the formula, $X_n$ is amino acid residue (s) selected from amino acids contiguous to the amino terminus of Y in the sequence shown in FIG. 8 (SEQ ID NO:2), i.e., from amino acid residue 23 to 1. $Z_m$ is amino acid residue(s) selected from amino acids contiguous to the carboxy terminus of Y in the sequence shown in FIG. 8 (SEQ ID NO:2), i.e., from amino acid residue 246 to 329. In addition, in the formula, n is a number from 0 to 23 (n=0–23) and m is a number from 0 to 84 (m=0–84). A particularly preferred peptide has an amino acid sequence represented by the formula $X_n-Y-Z_m$ as above, where n=0 and m=0.

Nucleic acid fragments within the scope of the invention include those capable of hybridizing with nucleic acid from other animal species for use in screening protocols to detect novel proteins that are cross-reactive with the B lymphocyte antigens described herein. These and other fragments are described in detail herein. Generally, the nucleic acid encoding a fragment of a B lymphocyte antigen will be selected from the bases coding for the mature protein, however, in some instances it may be desirable to select all or part of a fragment or fragments from the leader sequence or non-coding portion of a nucleotide sequence. Nucleic acids within the scope of the invention may also contain linker sequences, modified restriction endonuclease sites and other sequences useful for molecular cloning, expression or purification of recombinant protein or fragments thereof. These and other modifications of nucleic acid sequences are described in further detail herein.

A nucleic acid encoding a peptide having an activity of a novel B lymphocyte antigen, such as the B7-2 antigen, may be obtained from mRNA present in activated B lymphocytes. It should also be possible to obtain nucleic acid sequences encoding B lymphocyte antigens from B cell genomic DNA. For example, the gene encoding the B7-2 antigen can be cloned from either a cDNA or a genomic library in accordance with protocols herein described. A cDNA encoding the B7-2 antigen can be obtained by isolating total mRNA from an appropriate cell line. Double stranded cDNAs can then prepared from the total mRNA. Subsequently, the cDNAs can be inserted into a suitable plasmid or viral (e.g., bacteriophage) vector using any one of a number of known techniques. Genes encoding novel B lymphocyte antigens can also be cloned using established polymerase chain reaction techniques in accordance with the nucleotide sequence information provided by the invention. The nucleic acids of the invention can be DNA or RNA. A preferred nucleic acid is a cDNA encoding the human B7-2 antigen having the sequence depicted in FIG. 8 (SEQ ID NO:1). Another preferred nucleic acid is a cDNA encoding the murine B7-2 antigen having the sequence shown on FIG. 14 (SEQ ID NO:22).

This invention further pertains to expression vectors containing a nucleic acid encoding at least one peptide having the activity of a novel B lymphocyte antigen, as described herein, operably linked to at least one regulatory sequence. "Operably linked" is intended to mean that the nucleotide acid sequence is linked to a regulatory sequence in a manner which allows expression of the nucleotide sequence (e.g., in cis or trans). Regulatory sequences are art-recognized and are selected to direct expression of the desired protein in an appropriate host cell. Accordingly, the term regulatory sequence includes promoters, enhancers and other expression control elements. Such regulatory sequences are known to those skilled in the art or one described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type of protein desired to be expressed. In one embodiment, the expression vector includes a nucleic acid encoding at least a portion of the B7-2 protein, such as an extracellular domain portion. In another embodiment, the expression vector includes a DNA encoding a peptide having an activity of the B7-2 antigen and a DNA encoding a peptide having an activity of another B lymphocyte antigen, such as B7-1. cDNAs encoding the human B7-1 and mouse B7-1 antigens are shown in SEQ ID NO:28 and SEQ ID NO:30, respectively. The deduced amino acid sequences of these antigens are also shown in SEQ ID NO:29 and SEQ ID NO:3 1, respectively. Such expression vectors can be used to transfect cells to thereby produce proteins or peptides, including fusion proteins or peptides encoded by nucleic acid sequences as described herein. These and other embodiments are described in further detail herein.

The invention also features methods of producing peptides having an activity of a novel B lymphocyte antigen. For example, a host cell transfected with a nucleic acid vector directing expression of a nucleotide sequence encoding a peptide having an activity of the B7-2 protein can be cultured in a medium under appropriate conditions to allow expression of the peptide to occur. In addition, one or more expression vectors containing DNA encoding a peptide having an activity of B7-2 and DNA encoding another peptide, such as a peptide having an activity of a second B lymphocyte antigen (e.g., B7-1, B7-3) can be used to transfect a host cell to coexpress these peptides or produce fusion proteins or peptides. In one embodiment, a recombinant expression vector containing DNA encoding a B7-2 fusion protein is produced. A B7-2 fusion protein can be produced by recombinant expression of a nucleotide sequence encoding a first peptide having B7-2 activity and a nucleotide sequence encoding second peptide corresponding to a moiety that alters the solubility, affinity, stability or valency of the first peptide, for example, an immunoglobulin constant region. Preferably, the first peptide consists of a portion of the extracellular domain of the human B7-2 antigen (e.g., approximately amino acid residues 24–245 of the sequence shown in FIG. 8 (SEQ ID NO:2)). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. No. 5,116,964, incorporated herein by reference). A resulting B7-2Ig fusion protein may have altered B7-2 solubility, binding affinity, stability and/or valency (i.e., the number of binding sites available per molecule) and may increase the efficiency of protein purification. Fusion proteins and peptides produced by recombinant technique may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable mediums for cell culture are well known in the art. Protein and peptides can be isolated from cell culture medium, host cells, or both using techniques known in the art for purifying proteins and peptides. Techniques for transfecting host cells and purifying proteins and peptides are described in further detail herein.

Particularly preferred human B7-2Ig fusion proteins include the extracellular domain portion or variable region-like domain of human B7-2 coupled to an immunoglobulin constant region. The immunoglobulin constant region may contain genetic modifications which reduce or eliminate effector activity inherent in the immunoglobulin structure. For example, DNA encoding the extracellular portion of human B7-2 (hB7-2), as well as DNA encoding the variable region-like domain of human B7-2 (hB7.2V) or the constant region-like domain of human B7-2 (hB7.2C) can be joined to DNA encoding the hinge, CH2 and CH3 regions of human IgCγ1 and/or IgCγ4 modified by site directed mutagenesis. The preparation and characterization of these fusion proteins is described in detail in Example 7.

Transfected cells which express peptides having an activity of one or more B lymphocyte antigens (e.g., B7-2, B7-3) on the surface of the cell are also within the scope of this invention. In one embodiment, a host cell such as a COS cell is transfected with an expression vector directing the expression of a peptide having B7-2 activity on the surface of the cell. Such a transfected host cell can be used in methods of identifying molecules which inhibit binding of B7-2 to its counter-receptor on T cells or which interfere with intracellular signaling of costimulation to T cells in response to B7-2 interaction. In another embodiment, a tumor cell such as a sarcoma, a melanoma, a leukemia, a lymphoma, a carcinoma or a neuroblastoma is transfected with an expression vector directing the expression of at least one peptide having the activity of a novel B lymphocyte antigen on the surface of the tumor cell. In some instances, it may be beneficial to transfect a tumor cell to coexpress major histocompatibility complex (MHC) proteins, for example MHC class II α and β chain proteins or an MHC class I α chain protein, and, if necessary, a β2 microglobulin protein. Such transfected tumor cells can be used to induce tumor immunity in a subject. These and other embodiments are described in further detail herein.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Another aspect of the invention pertains to isolated peptides having an activity of a novel B lymphocyte antigen (e.g., B7-2, B7-3). A peptide having an activity of a B lymphocyte antigen may differ in amino acid sequence from the B lymphocyte antigen, such as the human B7-2 sequence depicted in FIG. 8 (SEQ ID NO:2), or murine B7-2 sequence depicted in FIG. 14 (SEQ ID NO:22), but such differences result in a peptide which functions in the same or similar manner as the B lymphocyte antigen or which has the same or similar characteristics of the B lymphocyte antigen. For example, a peptide having an activity of the B7-2 protein is defined herein as a peptide having the ability to bind to the natural ligand(s) of the B7-2 protein on immune cells, such as CTLA4 and/or CD28 on T cells and either stimulate or inhibit immune cell costimulation. Thus, a peptide having B7-2 activity binds CTLA4 and/or CD28 and stimulates or inhibits a T cell mediated immune response (as evidenced by, for example, cytokine production and/or proliferation by T cells that have received a primary activation signal). One embodiment provides a peptide having B7-2 binding activity, but lacking the ability to deliver a costimulatory signal to T cells. Such a peptide can be used to inhibit or block T cell proliferation and/or cytokine secretion in a subject. Alternatively, a peptide having both B7-2 binding activity and the ability to deliver a costimulatory signal to T cells is used to stimulate or enhance T cell proliferation and/or cytokine secretion in a subject. Various modifications of the B7-2 protein to produce these and other functionally equivalent peptides are described in detail herein. The term "peptide" as used herein, refers to peptides, proteins and polypeptides.

A peptide can be produced by modification of the amino acid sequence of the human B7-2 protein shown in FIG. 8 (SEQ ID NO:2) or the murine B7-2 protein shown in FIG. 14 (SEQ ID NO:23), such as a substitution, addition or deletion of an amino acid residue which is not directly involved in the function of B7-2 (i.e., the ability of B7-2 to bind CTLA4 and/or CD28 and/or stimulate or inhibit T cell costimulation). Peptides of the invention are typically at least 20 amino acid residues in length, preferably at least 40 amino acid residues in length, and most preferably 60 amino acid residues in length. Peptides having B7-2 activity and including at least 80 amino acid residues in length, at least 100 amino acid residues in length, or at least 200 or more amino acid residues in length are also within the scope of the invention. A preferred peptide includes an extracellular domain portion of the human B7-2 antigen (e.g., about amino acid residues 24–245 of the sequence shown in FIG. 8 (SEQ ID NO:2). Other preferred peptides have an amino acid sequence represented by a formula:

$$X_n-Y-Z_m$$

where Y is amino acid residues selected from the group consisting of: amino acid residues 55–68 of the sequence shown in FIG. 8 (SEQ ID NO:2); amino acid residues 81–89 of the sequence shown in FIG. 8 (SEQ ID NO:2); amino acid residues 128–142 of the sequence shown in FIG. 8 (SEQ ID NO:2); amino acid residues 160–169 of the sequence shown in FIG. 8 (SEQ ID NO:2); amino acid residues 188–200 of the sequence shown in FIG. 8 (SEQ ID NO:2); and amino acid residues 269–282 of the sequence shown in FIG. 8 (SEQ ID NO:2). In the formula, $X_n$ and $Z_m$ are additional amino acid residues linked to Y by an amide bond. $X_n$ and $Z_m$ are amino acid residues selected from amino acids contiguous to Y in the amino acid sequence shown in FIG. 8 (SEQ ID NO:2). $X_n$ is amino acid residues selected from amino acids contiguous to the amino terminus of Y in the sequence shown in FIG. 8 (SEQ ID NO:2). $Z_m$ is amino acid residues selected from amino acids contiguous to the carboxy terminus of Y in the sequence shown in FIG. 8 (SEQ ID NO:2). According to the formula, n is a number from 0 to 30 (n=0–30) and m is a number from 0 to 30 (m=0–30). A particularly preferred peptide has an amino acid sequence represented by the formula $X_n-Y-Z_m$, where n=0 and m=0.

Another embodiment of the invention provides a substantially pure preparation of a peptide having an activity of a novel B lymphocyte antigen such as B7-2 or B7-3. Such a preparation is substantially free of proteins and peptides with which the peptide naturally occurs in a cell or with which it naturally occurs when secreted by a cell.

The term "isolated" as used throughout this application refers to a nucleic acid, protein or peptide having an activity of a novel B lymphocyte antigen, such as B7-2, substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived.

These and other aspects of this invention are described in detail in the following subsections.

I. Isolation of Nucleic Acid From Cell Lines

Suitable cells for use in isolating nucleic acids encoding peptides having an activity of a novel B lymphocyte antigen include cells capable of producing mRNA coding for B lymphocyte antigens (e.g., B7-1, B7-2, B7-3) and appropriately translating the mRNA into the corresponding protein. One source of mRNA is normal human splenic B cells, either resting or activated by treatment with an anti-immunoglobulin antibody or an anti-MHC class II antibody, or from subsets of neoplastic B cells. Expression of the human B7-2 antigen is detectable in resting B cells and in activated B cells, with mRNA levels increasing 4-fold from resting levels following stimulation. Total cellular RNA can be obtained using standard techniques from resting or activated B cells during these intervals and utilized in the construction of a cDNA library.

In addition, various subsets of neoplastic B cells may express B7-2 and B7-3 and can alternatively serve as a source of the mRNA for construction of a cDNA library. For example, tumor cells isolated from patients with non-Hodgkins lymphoma express B7-1 mRNA. B cells from nodular, poorly differentiated lymphoma (NPDL), diffuse large cell lymphoma (LCL) and Burkitt's lymphoma cell lines are also suitable sources of human B7-1 mRNA and, potentially B7-2 and B7-3 mRNA. Myelomas generally express B7-2, but not B7-1 mRNA, and, thus can provide a source of B7-2 mRNA. The Burkitt's lymphoma cell line Raji is one source of B lymphocyte antigen mRNA. Preferably, B7-2 mRNA is obtained from a population of both resting and activated normal human B cells. Activated B cells can be obtained by stimulation over a broad spectrum of time (e.g., from minutes to days) with, for example, an anti-immunoglobulin antibody or an anti-MCH class II antibody.

II. Isolation of mRNA and Construction of cDNA Library

Total cellular mRNA can be isolated by a variety of techniques, e.g., by using the guanidinium-thiocyanate extraction procedure of Chirgwin et al., *Biochemistry* 18, 5294–5299 (1979). According to this method, Poly (A+) mRNA is prepared and purified for use in a cDNA library construction using oligo (dT) cellulose selection. cDNA is then synthesized from the poly(A+) RNA using oligo(dT) priming and reverse transcriptase. Moloney MLV reverse transcriptase (available from Gibco/BRL, Bethesda, Md.) or AMV reverse transcriptase (available from Seikagaku America, Inc., St. Petersburg, Fla.) are preferably employed.

Following reverse transcription, the mRNA/DNA hybrid molecule is converted to double stranded DNA using conventional techniques and incorporated into a suitable vector. The experiments herein employed *E. coli* DNA polymerase I and ribonuclease H in the conversion to double stranded cDNA.

Cloning of the cDNAs can be accomplished using any of the conventional techniques for joining double stranded DNA with an appropriate vector. The use of synthetic adaptors is particularly preferred, since it alleviates the possibility of cleavage of the cDNA with restriction enzyme prior to cloning. Using this method, non-self complementary, kinased adaptors are added to the DNA prior to ligation with the vector. Virtually any adaptor can be employed. As set forth in more detail in the examples below, non-self complementary BstXI adaptors are preferably added to the cDNA for cloning, for ligation into a pCDM8 vector prepared for cloning by digestion with BstXI.

Eucaryotic cDNA can be expressed when placed in the sense orientation in a vector that supplies an appropriate eucaryotic promoter and origin of replication and other elements including enhancers, splice acceptors and/or donor sequences and polyadenylation signals. The cDNAs of the present invention are placed in suitable vectors containing a eucaryotic promoter, an origin of replication functional in *E. coli*, an SV40 origin of replication which allows growth in COS cells, and a cDNA insertion site. Suitable vectors include πH3 (Seed and Aruffo, *Proc. Natl. Acad. Sci.,* 84:3365–3369 (1987)), πH3m (Aruffo and Seed, *Proc. Natl. Acad. Sci.,* 84:8573–8577 (1987)), pCDM7 and pCDM8 (Seed, *Nature,* 329:840–841 (1987), with the pCDM8 vector being particularly preferred (available commercially from Invitrogen, San Diego, Calif.).

III. Transfection of Host Cells and Screening for Novel B Lymphocyte Activation Antigens The thus prepared cDNA library is then used to clone the gene of interest by expression cloning techniques. A basic expression cloning technique has been described by Seed and Aruffo, *Proc. Natl. Acad. Sci. USA,* 84:3365–3369 (1987) and Aruffo and Seed, *Proc. Natl. Acad. Sci. USA,* 84:8573–8577 (1987), although modifications to this technique may be necessary.

According to one embodiment, plasmid DNA is introduced into a simian COS cell line (Gluzman, *Cell* 23:175 (1981)) by known methods of transfection (e.g., DEAE-Dextran) and allowed to replicate and express the cDNA inserts. The transfectants expressing B7-1 antigen are depleted with an anti-B7-1 monoclonal antibody (e.g., 133 and B1.1) and anti-murine IgG and IgM coated immuno-magnetic beads. Transfectants expressing human B7-2 antigen can be positively selected by reacting the transfectants with the fusion proteins CTLA4Ig and CD28Ig, followed by panning with anti-human Ig antibody coated plates. Although human CTLA4Ig and CD28Ig fusion proteins were used in the examples described herein, given the cross-species reactivity between B7-1 and, for example murine B7-1, it can be expected that other fusion proteins reactive with another cross-reactive species could be used. After panning, episomal DNA is recovered from the panned cells and transformed into a competent bacterial host, preferably *E. coli*. Plasmid DNA is subsequently reintroduced into COS cells and the cycle of expression and panning repeated at least two times. After the final cycle, plasmid DNA is prepared from individual colonies, transfected into COS cells and analyzed for expression of novel B lymphocyte antigens by indirect immunofluorescence with, for example, CTLA4Ig and CD28Ig.

IV. Sequencing of Novel B Lymphocyte Antigens

Plasmids are prepared from those clones which are strongly reactive with the CTLA4Ig and/or CD28Ig. These plasmids are then sequenced. Any of the conventional sequencing techniques suitable for sequencing tracts of DNA about 1.0 kb or larger can be employed.

As described in Example 4, a human B7-2 clone (clone29) was obtained containing an insert of 1,120 base pairs with a single long open reading frame of 987 nucleotides and approximately 27 nucleotides of 3' noncoding sequences (FIG. 8, SEQ ID NO:1). The predicted amino acid sequence encoded by the open reading frame of the protein is shown below the nucleotide sequence in FIG. 8. The encoded human B7-2 protein, is predicted to be 329 amino acid residues in length (SEQ ID NO:2). This protein sequence exhibits many features common to other type I Ig superfamily membrane proteins. Protein translation is predicted to begin at the methionine codon (ATG, nucleotides 107 to 109) based on the DNA homology in this region with the consensus eucaryotic translation initiation site (see Kozak, M. (1987) Nucl. Acids Res. 15:8125–8148). The amino terminus of the B7-2 protein (amino acids 1 to 23) has the characteristics of a secretory signal peptide with a predicted cleavage between the alanines at positions 23 and 24 (von Heijne (1987) Nucl. Acids Res. 14:4683). Processing at this site would result in a B7-2 membrane bound protein of 306 amino acids having an unmodified molecular weight of approximately 34 kDa. This protein would consist of an approximate extracellular Ig superfamily V and C like domains of from about amino acid residue 24 to 245, a hydrophobic transmembrane domain of from about amino acid residue 246 to 268, and a long cytoplasmic domain of from about amino acid residue 269 to 329. The homologies to the Ig superfamily are due to the two contiguous Ig-like domains in the extracellular region bound by the cysteines at positions 40 to 110 and 157 to 218. The extracellular domain also contains eight potential N-linked glycosylation sites and, like B7-1, is probably glycosylated. Glycosylation of the human B7-2 protein may increase the molecular weight to about 50–70 kDa. The cytoplasmic domain of human B7-2, while somewhat longer than B7-1, contains a common region of multiple cysteines followed by positively charged amino acids which presumably function as signaling or regulatory domains within an antigen-presenting cell (APC). Comparison of both the nucleotide and amino acid sequences of the human B7-2 with the GenBank and EMBL databases yielded significant homology (about 26% amino acid sequence identity) with human B7-1. Since human B7-1, human B7-2 and murine B7-1 all bind to human CTLA4 and CD28, the homologous amino acids probably represent those necessary to comprise a CTLA4 or CD28 binding sequence. E. coli transfected with a vector containing a cDNA insert encoding human B7-2 (clone 29) was deposited with the American Type Culture Collection (ATCC) on July 26, 1993 as Accession No. 69357.

V. Cloning Novel B Lymphocyte Antigens from Other Mammalian Species

The present invention is not limited to human nucleic acid molecules and contemplates that novel B lymphocyte antigen homologues from other mammalian species that express B lymphocyte antigens can be cloned and sequenced using the techniques described herein. B lymphocyte antigens isolated for one species (e.g., humans) which exhibit cross-species reactivity may be used to modify T cell mediated immune responses in a different species (e.g., mice). Isolation of cDNA clones from other species can also be accomplished using human cDNA inserts, such as human B7-2 cDNA, as hybridization probes.

As described in Example 6, a murine B7-2 clone (mB7-2, clone 4) was obtained containing an insert of 1,163 base pairs with a single long open reading frame of 927 nucleotides and approximately 126 nucleotides of 3' noncoding sequences (FIG. 14, SEQ ID NO:22). The predicted amino acid sequence encoded by the open reading frame of the protein is shown below the nucleotide sequence in FIG. 14. The encoded murine B7-2 protein, is predicted to be 309 amino acid residues in length (SEQ ID NO:23). This protein sequence exhibits many features common to other type I Ig superfamily membrane proteins. Protein translation is predicted to begin at the methionine codon (ATG, nucleotides 111 to 113) based on the DNA homology in this region with the consensus eucaryotic translation initiation site (see Kozak, M. (1987) Nucl. Acids Res. 15:8125–8148). The amino terminus of the murine B7-2 protein (amino acids 1 to 23) has the characteristics of a secretory signal peptide with a predicted cleavage between the alanine at position 23 and the valine at position 24 (von Heijne (1987) Nucl. Acids Res. L4:4683). Processing at this site would result in a murine B7-2 membrane bound protein of 286 amino acids having an unmodified molecular weight of approximately 32 kDa. This protein would consist of an approximate extracellular Ig superfamily V and C like domains of from about amino acid residue 24 to 246, a hydrophobic transmembrane domain of from about amino acid residue 247 to 265, and a long cytoplasmic domain of from about amino acid residue 266 to 309. The homologies to the Ig superfamily are due to the two contiguous Ig-like domains in the extracellular region bound by the cysteines at positions 40 to 110 and 157 to 216. The extracellular domain also contains nine potential N-linked glycosylation sites and, like murine B7-1, is probably glycosylated. Glycosylation of the murine B7-2 protein may increase the molecular weight to about 50–70 kDa. The cytoplasmic domain of murine B7-2 contains a common region which has a cysteine followed by positively charged amino acids which presumably functions as signaling or regulatory domain within an APC. Comparison of both the nucleotide and amino acid sequences of murine B7-2 with the GenBank and EMBL databases yielded significant homology (about 26% amino acid sequence identity) with human and murine B7-1. Murine B7-2 exhibits about 50% identity and 67% similarity with its human homologue, hB7-2. E. coli (DH106/p3) transfected with a vector (plasmid pmBx4) containing a cDNA insert encoding murine B7-2 (clone 4) was deposited with the American Type Culture Collection (ATCC) on Aug. 18, 1993 as Accession No. 69388.

Nucleic acids which encode novel B lymphocyte antigens from other species, such as the murine B7-2, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, murine B7-2 cDNA or an appropriate sequence thereof can be used to clone genomic B7-2 in accordance with established techniques and the genomic sequences used to generate transgenic animals that contain cells which express B7-2 protein. Methods for generating transgenic animals, particularly animals such as mice, have become conventional in the art and are described, for example, in U.S. Pat. Nos. 4,736,866 and 4,870,009. Typically, particular cells would be targeted for B7-2 transgene incorporation with tissue specific enhancers, which could result in T cell costimulation and enhanced T cell proliferation and autoimmunity. Transgenic animals that include a copy of a B7-2 transgene introduced into the germ line of the animal at an embryonic stage can be used to examine the effect of increased B7 expression. Such animals can be used as tester animals for reagents thought to confer protection from, for example, autoimmune disease. In accordance with this facet of the invention, an animal is treated with the reagent and a reduced incidence of the disease, compared to untreated animals bearing the transgene, would indicate a potential therapeutic intervention for the disease.

Alternatively, the non-human homologues of B7-2 can be used to construct a B7-2 "knock out" animal which has a defective or altered B7-2 gene as a result of homologous recombination between the endogenous B7-2 gene and altered B7-2 genomic DNA introduced into an embryonic cell of the animal. For example, murine B7-2 cDNA can be used to clone genomic B7-2 in accordance with established techniques. A portion of the genomic B7-2 DNA (e.g., such as an exon which encodes an extracellular domain) can be deleted or replaced with another gene, such as a gene encoding a selectable marker which can be used to monitor integration. Typically, several kilobases of unaltered flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term to create a "knock out" animal. Progeny harbouring the homologously recombined DNA in their germ cells can be identified by standard techniques and used to breed animals in which all cells of the animal contain the homologously recombined DNA. Knockout animals can be characterized for their ability to accept grafts, reject tumors and defend against infectious diseases and can be used in the study of basic immunobiology.

VI. Expression of B Lymphocyte Antigens

Host cells transfected to express peptides having the activity of a novel B lymphocyte antigen are also within the scope of the invention. The host cell may be any procaryotic or eucaryotic cell. For example, a peptide having B7-2 activity may be expressed in bacterial cells such as *E. coli,* insect cells (baculovirus), yeast, or mammalian cells such as Chinese hamster ovary cells (CHO) and NSO cells. Other suitable host cells may be found in Goeddel, (1990) supra or are known to those skilled in the art.

For example, expression in eucaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39). Generally, COS cells (Gluzman, Y., (1981) *Cell* 23:175–182) are used in conjunction with such vectors as pCDM8 (Seed, B., (1987) *Nature* 329:840) for transient amplification/expression in mammalian cells, while CHO (dhfr$^-$ Chinese Hamster Ovary) cells are used with vectors such as pMT2PC (Kaufman et al. (1987), *EMBO J.* 6:187–195) for stable amplification/expression in mammalian cells. A preferred cell line for production of recombinant protein is the NSO myeloma cell line available from the ECACC (catalog #85110503) and described in Galfre, G. and Milstein, C. ((1981) *Methods in Enzymology* 73((13):3–46; and *Preparation of Monoclonal Antibodies: Strategies and Procedures,* Academic Press, N.Y., N.Y). Vector DNA can be introduced into mammalian cells via conventional techniques such as calcium phosphate or calcium chloride co-precipitation, DEAE-dextran-mediated transfection, lipofectin, or electroporation. Suitable methods for transforming host cells can be found in Sambrook et al. (*Molecular Cloning: A Laboratory Manual,* 2nd Edition, Cold Spring Harbor Laboratory press (1989)), and other laboratory textbooks. When used in mammalian cells, the expression vector's control functions are often provided by viral material. For example, commonly used promoters are derived from polyoma, Adenovirus 2, cytomegalovirus and most frequently, Simian Virus 40.

It is known that a small faction of cells (about 1 out of 105) typically integrate DNA into their genomes. In order to identify these integrants, a gene that contains a selectable marker (i.e., resistance to antibiotics) is generally introduced into the host cells along with the gene of interest. Preferred selectable markers include those which confer resistance to drugs, such as G418, hygromycin and methotrexate. Selectable markers may be introduced on the same plasmid as the gene of interest or may be introduced on a separate plasmid. Cells containing the gene of interest can be identified by drug selection; cells that have incorporated the selectable marker gene will survive, while the other cells die. The surviving cells can then be screened for production of novel B lymphocyte antigens by cell surface staining with ligands to the B cell antigens (e.g., CTLA4Ig and CD28Ig). Alternatively, the protein can be metabolically radiolabeled with a labeled amino acid and immunoprecipitated from cell supernatant with an anti-B lymphocyte antigen monoclonal antibody or a fusion protein such as CTLA4Ig or CD28Ig.

Expression in procaryotes is most often carried out in *E. coli* with vectors containing constitutive or inducible promotors directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

E. coli expression systems include the inducible expression vectors pTrc (Amann et al., (1988) *Gene* 69:301–315) and pET 11 (Studier et al., *Gene Expression Technology: Methods in Enzymology* 185, Academic Press, San Diego, Calif. (1990) 60–89; commercially available from Novagen). In the pTrc vector system, the inserted gene is expressed with a pelB signal sequence by host RNA polymerase transcription from a hybrid trp-lac fusion promoter. After induction, the recombinant protein can be purified from the periplasmic fraction. In the pET 11 vector system, the target gene is expressed as non-fusion protein by transcription from the T7 gn10-lac 0 fusion promoter mediated by a coexpressed viral RNA polymerase (T7 gn1). This viral polymerase is supplied by host *E. coli* strains BL21(DE3) or HMSI74(DE3) from a resident λ prophage harboring a T7 gn1 under the transcriptional control of the lacUV 5 promoter. In this system, the recombinant protein can be purified from inclusion bodies in a denatured form and, if desired, renatured by step gradient dialysis to remove denaturants.

One strategy to maximize recombinant B7-2 expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid sequence of the B7-2 gene or other DNA to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention could be carried out by standard DNA synthesis techniques.

Novel B lymphocyte antigens and portions thereof, expressed in mammalian cells or otherwise, can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22:233–577 (1971)). Once purified, partially or to homogeneity, the recombinantly produced B lymphocyte antigens or portions thereof can be utilized in compositions suitable for pharmaceutical administration as described in detail herein.

VII. Modifications of Nucleic Acid and Amino Acid Sequences of the Invention and Assays for B7 Lymphocyte Antigen Activity It will be appreciated by those skilled in the art that other nucleic acids encoding peptides having the activity of a novel B lymphocyte antigen can be isolated by the above process. Different cell lines can be expected to yield DNA molecules having different sequences of bases. Additionally, variations may exist due to genetic polymorphisms or cell-mediated modifications of the genetic material. Furthermore, the DNA sequence of a B lymphocyte antigen can be modified by genetic techniques to produce proteins or peptides with altered amino acid sequences. Such sequences are considered within the scope of the present invention, where the expressed peptide is capable of either inducing or inhibiting activated T cell mediated immune responses and immune function.

A number of processes can be used to generate equivalents or fragments of an isolated DNA sequence. Small subregions or fragments of the nucleic acid encoding the B7-2 protein, for example 1–30 bases in length, can be prepared by standard, synthetic organic chemical means. The technique is also useful for preparation of antisense oligonucleotides and primers for use in the generation of larger synthetic fragments of B7-2 DNA.

Larger subregions or fragments of the genes encoding B lymphocyte antigens can be expressed as peptides by synthesizing the relevant piece of DNA using the polymerase chain reaction (PCR) (Sambrook, Fritsch and Maniatis, 2 *Molecular Cloning; A Laboratory Manual,* Cold Spring Harbor, N.Y., (1989)), and ligating the thus obtained DNA into an appropriate expression vector. Using PCR, specific sequences of the cloned double stranded DNA are generated, cloned into an expression vector, and then assayed for CTLA4/CD28 binding activity. For example, to express a secreted (soluble) form of the human B7-2 protein, using PCR, a DNA can be synthesized which does not encode the transmembrane and cytoplasmic regions of the protein. This DNA molecule can be ligated into an appropriate expression vector and introduced into a host cell such as CHO, where the B7-2 protein fragment is synthesized and secreted. The B7-2 protein fragment can then readily be obtained from the culture media.

In another embodiment, mutations can be introduced into a DNA by any one of a number of methods, including those for producing simple deletions or insertions, systematic deletions, insertions or substitutions of clusters of bases or substitutions of single bases, to generate variants or modified equivalents of B lymphocyte antigen DNA. For example, changes in the human B7-2 cDNA sequence shown in FIG. 8 (SEQ ID NO:1) or murine B7-2 cDNA sequence shown in FIG. 14 (SEQ ID NO:22) such as amino acid substitutions or deletions are preferably obtained by site-directed mutagenesis. Site directed mutagenesis systems are well known in the art. Protocols and reagents can be obtained commercially from Amersham International PLC, Amersham, U.K.

Peptides having an activity of a novel B lymphocyte antigen, i.e., the ability to bind to the natural ligand(s) of a B lymphocyte antigen on T cells and either stimulate (amplify) or inhibit (block) activated T cell mediated immune responses, as evidenced by, for example, cytokine production and/or T cell proliferation by T cells that have received a primary activation signal are considered within the scope of the invention. More specifically, peptides that bind to T lymphocytes, for example CD28$^+$ cells, may be capable of delivering a costimulatory signal to the T lymphocytes, which, when transmitted in the presence of antigen and class II MHC, or other material capable of transmitting a primary signal to the T cell, results in activation of cytokine genes within the T cell. Alternatively, such a peptide can be used in conjunction with class I MHC to thereby activate CD8$^+$ cytolytic T cells. In addition, soluble, monomeric forms of the B7-2 protein, may retain the ability to bind to their natural ligand(s) on CD28$^+$ T cells but, perhaps because of insufficient cross-linking with the ligand, fail to deliver the secondary signal essential for enhanced cytokine production and cell division. Such peptides, which provide a means to induce a state of anergy or tolerance in the cells, are also considered within the scope of the invention.

Screening the peptides for those which retain a characteristic B lymphocyte antigen activity as described herein can be accomplished using one or more of several different assays. For example, the peptides can be screened for specific reactivity with an anti-B7-2 monoclonal antibody reactive with cell surface B7-2 or with a fusion protein, such as CTLA4Ig or CD28Ig. Specifically, appropriate cells, such as COS cells, can be transfected with a B7-2 DNA encoding a peptide and then analyzed for cell surface phenotype by indirect immunofluorescence and flow cytometry to determine whether the peptide has B7-2 activity. Cell surface expression of the transfected cells is evaluated using a monoclonal antibody specifically reactive with cell surface B7-2 or with a CTLA4Ig or CD28Ig fusion protein. Production of secreted forms of B7-2 is evaluated using anti-B7-2 monoclonal antibody or CTLA4Ig or CD28 fusion protein for immunoprecipitation.

Other, more preferred, assays take advantage of the functional characteristics of the B7-2 antigen. As previously set forth, the ability of T cells to synthesize cytokines depends not only on occupancy or cross-linking of the T cell receptor for antigen (the "primary activation signal" provided by, for example anti-CD3, or phorbol ester to produce an "activated T cell"), but also on the induction of a costimulatory signal, in this case, by interaction with a B lymphocyte antigen, such as B7-2, B7-1 or B7-3. The binding of B7-2 to its natural ligand(s) on, for example, $CD28^+$ T cells, has the effect of transmitting a signal to the T cell that induces the production of increased levels of cytokines, particularly of interleukin-2, which in turn stimulates the proliferation of the T lymphocytes. Other assays for B7-2 function thus involve assaying for the synthesis of cytokines, such as interleukin-2, interleukin-4 or other known or unknown novel cytokines, and/or assaying for T cell proliferation by $CD28^+$ T cells which have received a primary activation signal.

In vitro, T cells can be provided with a first or primary activation signal by anti-T3 monoclonal antibody (e.g. anti-CD3) or phorbol ester or, more preferably, by antigen in association with class II MHC. T cells which have received a primary activation signal are referred to herein as activated T cells. B7-2 function is assayed by adding a source of B7-2 (e.g., cells expressing a peptide having B7-2 activity or a secreted form of B7-2) and a primary activation signal such as antigen in association with Class II MHC to a T cell culture and assaying the culture supernatant for interleukin-2, gamma interferon, or other known or unknown cytokine. For example, any one of several conventional assays for interleukin-2 can be employed, such as the assay described in *Proc. Natl. Acad. Sci. USA,* 86:1333 (1989) the pertinent portions of which are incorporated herein by reference. A kit for an assay for the production of interferon is also available from Genzyme Corporation (Cambridge, Mass.). T cell proliferation can also be measured as described in the Examples below. Peptides that retain the characteristics of the B7-2 antigen as described herein may result in increased per cell production of cytokines, such as IL-2, by T cells and may also result in enhanced T cell proliferation when compared to a negative control in which a costimulatory signal is lacking.

The same basic functional assays can also be used to screen for peptides having B7-2 activity, but which lack the ability to deliver a costimulatory signal, but in the case of such peptides, addition of the B7-2 protein will not result in a marked increase in proliferation or cytokine secretion by the T cells. The ability of such proteins to inhibit or completely block the normal B7-2 costimulatory signal and induce a state of anergy can be determined using subsequent attempts at stimulation of the T cells with antigen presenting cells that express cell surface B7-2 and present antigen. If the T cells are unresponsive to the subsequent activation attempts, as determined by IL-2 synthesis and T cell proliferation, a state of anergy has been induced. See, e.g., Gimmi, C. D. et al. (1993) *Proc. Natl. Acad. Sci. USA* 90, 6586–6590; and Schwartz (1990) *Science,* 248, 1349–1356, for assay systems that can used as the basis for an assay in accordance with the present invention.

It is possible to modify the structure of a peptide having the activity of a novel B lymphocyte antigen for such purposes as increasing solubility, enhancing therapeutic or prophylactic efficacy, or stability (e.g., shelf life ex vivo and resistance to proteolytic degradation in vivo). Such modified peptides are considered functional equivalents of the B lymphocyte antigens as defined herein. For example, a peptide having B7-2 activity can be modified so that it maintains the ability to co-stimulate T cell proliferation and/or produce cytokines. Those residues shown to be essential to interact with the CTLA4/CD28 receptors on T cells can be modified by replacing the essential amino acid with another, preferably similar amino acid residue (a conservative substitution) whose presence is shown to enhance, diminish, but not eliminate, or not effect receptor interaction. In addition, those amino acid residues which are not essential for receptor interaction can be modified by being replaced by another amino acid whose incorporation may enhance, diminish, or not effect reactivity.

Another example of modification of a peptide having the activity of a novel B lymphocyte antigen is substitution of cysteine residues preferably with alanine, serine, threonine, leucine or glutamic acid residues to minimize dimerization via disulfide linkages. In addition, amino acid side chains of a peptide having B7-2 activity can be chemically modified. Another modification is cyclization of the peptide.

In order to enhance stability and/or reactivity, peptides having B7-2 activity can be modified to incorporate one or more polymorphisms in the amino acid sequence of the antigen resulting from any natural allelic variation. Additionally, D-amino acids, non-natural amino acids, or non-amino acid analogs can be substituted or added to produce a modified protein within the scope of this invention. Furthermore, the peptides can be modified using polyethylene glycol (PEG) according to the method of A. Sehon and co-workers (Wie et al. supra) to produce a peptide conjugated with PEG. In addition, PEG can be added during chemical synthesis of the peptide. Other modifications of the peptides include reduction/alkylation (Tarr in: *Methods of Protein Microcharacterization,* J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology,* W H Freeman, San Francisco, Calif. (1980), U.S. Pat. No. 4,939, 239; or mild formalin treatment (Marsh (1971), *Int. Arch. of Allergy and Appl. Immunol.* 41:199–215).

To facilitate purification and potentially increase solubility of a peptide, it is possible to add an amino acid fusion moiety to the protein backbone. For example, hexa-histidine can be added to the peptide for purification by immobilized metal ion affinity chromatography (Hochuli, E. et al., (1988) *Bio/Technology* 6:1321–1325). In addition, to facilitate isolation of a B lymphocyte antigen free of irrelevant sequences, specific endoprotease cleavage sites can be introduced between the sequences of a fusion moiety and the peptide. It may be necessary to increase the solubility of a peptide by adding functional groups to the peptide, or by omitting hydrophobic regions of the peptide.

VII. Uses of Nucleic Acid Sequences Encoding B Lymphocyte Antigens and Peptides Having B7-2 Activity A. Molecular Probes The nucleic acids of this invention are useful diagnostically, for tracking the progress of disease, by measuring the activation status of B lymphocytes in biological samples or for assaying the effect of a molecule on the expresssion of a B lymphocyte antigen (e.g., detecting cellular mRNA levels). In accordance with these diagnostic assays, the nucleic acid sequences are labeled with a detectable marker, e.g., a radioactive, fluorescent, or biotinylated marker and used in a conventional dot blot or Northern hybridization procedure to probe mRNA molecules of total or poly(A+) RNAs from a biological sample.

B. Antibody Production

The peptides and fusion proteins produced from the nucleic acid molecules of the present invention can also be used to produce antibodies specifically reactive with B lymphocyte antigens. For example, by using a full-length B7-2 protein, or a peptide fragment thereof, having an amino acid sequence based on the predicted amino acid sequence of B7-2, anti-protein/anti-peptide polyclonal antisera or monoclonal antibodies can be made using standard methods. A mammal, (e.g., a mouse, hamster, or rabbit) can be immunized with an immunogenic form of the protein or peptide which elicits an antibody response in the mammal. The immunogen can be, for example, a recombinant B7-2 protein, or fragment thereof, a synthetic peptide fragment or a cell that expresses a B lymphocyte antigen on its surface. The cell can be for example, a splenic B cell or a cell transfected with a nucleic acid encoding a B lymphocyte antigen of the invention (e.g., a B7-2 cDNA) such that the B lymphocyte antigen is expressed on the cell surface. The immunogen can be modified to increase its immunogenicity. For example, techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with the peptide and monoclonal antibodies isolated.

The term antibody as used herein is intended to include fragments thereof which are also specifically reactive with a peptide having the activity of a novel B lymphocyte antigen or fusion protein as described herein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-B lymphocyte antigen (i.e., B7-2, B7-3) portion.

Particularly preferred antibodies are anti-human B7-2 monoclonal antibodies produced by hybridomas HA3.1F9, HA5.2B7 and HF2.3D1. The preparation and characterization of these antibodies is described in detail in Example 8. Monoclonal antibody HA3.1F9 was determined to be of the IgG1 isotype; monoclonal antibody HA5.2B7 was determined to be of the IgG2b isotype; and monoclonal antibody HF2.3D1 was determined to be of the IgG2a isotype. Hybidoma cells were deposited with the American Type Culture Collection, which meets the requirements of the Budapest Treaty, on Jul. 19, 1994 as ATCC Accession No. HB 11688 (hybridoma HA3.1F9), ATCC Accession No. HB 11687 (HA5.2B7) and ATCC Accession No. HB 11686 (HF2.3D1).

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the gene product of the novel B lymphocyte antigens of the invention. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816, 567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a peptide having the activity of a B lymphocyte antigen as described herein can be further humanized by producing human variable region chimeras, in which parts of the variable regions, especially the conserved framework regions of the antigen-binding domain, are of human origin and only the hypervariable regions are of non-human origin. General reviews of "humanized" chimeric antibodies are provided by Morrison, S. L. (1985) *Science* 229:1202–1207 and by Oi et al. (1986) *BioTechniques* 4:214. Such altered immunoglobulin molecules may be made by any of several techniques known in the art, (e.g., Teng et al., *Proc. Natl. Acad Sci. U.S.A.*, 80:7308–7312 (1983); Kozbor et al., *Immunology Today*, 4:7279 (1983); Olsson et al., *Meth. Enzymol.*, 92:3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J. Immunol.* 141:4053–4060). Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

As an alternative to humanizing a monoclonal antibody from a mouse or other species, a human monoclonal antibody directed against a human protein can be generated. Transgenic mice carrying human antibody repertoires have been created which can be immunized with a human B lymphocyte antigen, such as B7-2. Splenocytes from these immunized transgenic mice can then be used to create hybridomas that secrete human monoclonal antibodies specifically reactive with a human B lymphocyte antigen (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci USA* 81:6851–6855; Bruggeman et al. (1993) *Year Immunol* 7:33–40; Tuaillon et al. (1993) *PNAS* 90:3720–3724; and Bruggeman et al. (1991) *Eur J Immunol* 21:1323–1326).

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies that bind a B lymphocyte antigen of the invention (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with a B lymphocyte antigen, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FRI) sequences, as well as primer to a conserved 3' constant region primer can be used for PCR amplification of the heavy and light chain variable regions from a number of murine antibodies (Larrick et al. (1991) *Biotechniques* 11:152–156). A similar strategy can also been used to amplify human heavy and light chain variable regions from human antibodies (Larrick et al. (1991) *Methods: Companion to Methods in Enzymology* 2:106–110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease The antibodies of the current invention can be used therapeutically to inhibit T cell activation through blocking receptor:ligand interactions necessary for costimulation of the T cell. These so-called "blocking antibodies" can be identified by their ability to inhibit T cell proliferation and/or cytokine production when added to an in vitro costimulation assay as described herein. The ability of blocking antibodies to inhibit T cell functions may result in immunosuppression and/or tolerance when these antibodies are administered in vivo.

C. Protein Purification

The polyclonal or monoclonal antibodies of the current invention, such as an antibody specifically reactive with a recombinant or synthetic peptide having B7-2 activity or B7-3 activity can also be used to isolate the native B lymphocyte antigen from cells. For example, antibodies reactive with the peptide can be used to isolate the naturally-occurring or native form of B7-2 from activated B lymphocytes by immunoaffinity chromatography. In addition, the native form of B7-3 can be isolated from B cells by immunoaffinity chromatography with monoclonal antibody BB-1.

D. Other Therapeutic Reagents

The nucleic acid sequences and novel B lymphocyte antigens described herein can be used in the development of therapeutic reagents having the ability to either upregulate (e.g., amplify) or downregulate (e.g., suppress or tolerize) T cell mediated immune responses. For example, peptides having B7-2 activity, including soluble, monomeric forms of the B7-2 antigen or a B7-2 fusion protein, e.g., B7-2Ig, and anti-B7-2 antibodies that fail to deliver a costimulatory signal to T cells that have received a primary activation signal, can be used to block the B7-2 ligand(s) on T cells and thereby provide a specific means by which to cause immunosuppression and/or induce tolerance in a subject. Such blocking or inhibitory forms of B lymphocyte antigens and fusion proteins and blocking antibodies can be identified by their ability to inhibit T cell proliferation and/or cytokine production when added to an in vitro costimulation assay as previously described herein. In contrast to the monomeric form, stimulatory forms of B7-2, such as an intact cell surface B7-2, retain the ability to transmit the costimulatory signal to the T cells, resulting in an increased secretion of cytokines when compared to activated T cells that have not received the secondary signal.

In addition, fusion proteins comprising a first peptide having an activity of B7-2 fused to a second peptide having an activity of another B lymphocyte antigen (e.g., B7-1) can be used to modify T cell mediated immune responses. Alternatively, two separate peptides having an activity of B lymphocyte antigens, for example, B7-2 and B7-1, or a combination of blocking antibodies (e.g., anti-B7-2 and anti-B7-1 monoclonal antibodies) can be combined as a single composition or administered separately (simultaneously or sequentially), to upregulate or downregulate T cell mediated immune responses in a subject. recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large diverse antibody display libraries, rapid sorting after each affinity separation round, and easy isolation of the antibody gene from purified display packages. In addition to commercially available kits for generating phage display libraries (e.g., the Pharmacia *Recombinant Phage Antibody System,* catalog no. 27-9400-01; and the Stratagene SurfZAP™ phage display kit, catalog no. 240612), examples of methods and reagents particularly amenable for use in generating a diverse antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370–1372; Hay et al. (1992) Hum Antibod Hybridomas 3:81–85; Huse et al. (1989) Science 246:1275–1281; Griffths et al. (1993) EMBO J. 12:725–734; Hawkins et al. (1992) J Mol Biol 226:889–896; Clackson et al. (1991) Nature 352:624–628; Gram et al. (1992) PNAS 89:3576–3580; Garrad et al. (1991) Bio/Technology 9:1373–1377; Hoogenboom et al. (1991) Nuc Acid Res 19:4133–4137; and Barbas et al. (1991) PNAS 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552–554, complete $V_H$ and $V_L$ domains of an antibody, joined by a flexible $(Gly_4\text{-}Ser)_3$ linker can be used to produce a single chain antibody which can render the display package separable based on antigen affinity. Isolated scFV antibodies immunoreactive with a peptide having activity of a B lymphocyte antigen can subsequently be formulated into a pharmaceutical preparation for use in the subject method.

Once displayed on the surface of a display package (e.g., filamentous phage), the antibody library is screened with a B lymphocyte antigen protein, or peptide fragment thereof, to identify and isolate packages that express an antibody having specificity for the B lymphocyte antigen. Nucleic acid encoding the selected antibody can be recovered from the display package (e.g., from the phage genome) and subcloned into other expression vectors by standard recombinant DNA techniques. Furthermore, a therapeutically active amount of one or more peptides having B7-2 activity and or B7-1 activity can be used in conjunction with other immunomodulating reagents to influence immune responses. Examples of other immunomodulating reagents include blocking antibodies, e.g., against CD28 or CTLA4, against other T cell markers or against cytokines, fusion proteins, e.g., CTLA4Ig, or immunosuppressive drugs, e.g., cyclosporine A or FK506.

The peptides produced from the nucleic acid molecules of the present invention may also be useful in the construction of therapeutic agents which block T cell function by destruction of the T cell. For example, as described, secreted forms of a B lymphocyte antigen can be constructed by standard genetic engineering techniques. By linking a soluble form of B7-1, B7-2 or B7-3 to a toxin such as ricin, an agent capable of preventing T cell activation can be made. Infusion of one or a combination of immunotoxins, e.g., B7-2-ricin, B7-1-ricin, into a patient may result in the death of T cells, particularly of activated T cells that express higher amounts of CD28 and CTLA4. Soluble forms of B7-2 in a monovalent form alone may be useful in blocking B7-2 function, as described above, in which case a carrier molecule may also be employed.

Another method of preventing the function of a B lymphocyte antigen is through the use of an antisense or triplex oligonucleotide. For example, an oligonucleotide complementary to the area around the B7-1, B7-2 or B7-3 translation initiation site, (e.g., for B7-1, TGGCCCATGGCTTCAGA, (SEQ ID NO:20) nucleotides 326–309 and for B7-2, GCCAAAATGGATCCCCA (SEQ ID NO:21)), can be synthesized. One or more antisense oligonucleotides can be added to cell media, typically at 200 μg/ml, or administered to a patient to prevent the synthesis of B7-1, B7-2 and/or B7-3. The antisense oligonucleotide is taken up by cells and hybridizes to the appropriate B lymphocyte antigen mRNA to prevent translation. Alternatively, an oligonucleotide which binds double-stranded DNA to form a triplex construct to prevent DNA unwinding and transcription can be used. As a result of either, synthesis of one or more B lymphocyte antigens is blocked.

E. Therapeutic Uses by Downregulation of Immune Responses

Given the structure and function of the novel B lymphocyte antigens disclosed herein, it is possible to downregulate the function of a B lymphocyte antigen, and thereby downregulate immune responses, in a number of ways. Downregulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Downregulating or preventing one or more B lymphocyte antigen functions, e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this manner prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens. For example, it may be desirable to block the function of B7-2 and B7-1, B7-2 and B7-3, B7-1 and B7-3 or B7-2, B7-1 and B7-3 by administering a soluble form of a combination of peptides having an activity of each of these antigens or a blocking antibody (separately or together in a single composition) prior to transplantation. Alternatively, inhibitory forms of B lymphocyte antigens can be used with other suppressive agents such as blocking antibodies against other T cell markers or against cytokines, other fusion proteins, e.g., CTLA4Ig, or immunosuppressive drugs.

The efficacy of particular blocking reagents in preventing organ transplant rejection or GVHD can be assessed using animal models that are predictive of efficacy in humans. The functionally important aspects of B7-1 are conserved structurally between species and it is therefore likely that other B lymphocyte antigens can function across species, thereby allowing use of reagents composed of human proteins in animal systems. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., *Science,* 257: 789–792 (1992) and Turka et al., *Proc. Natl. Acad. Sci. USA,* 89: 11102–11105 (1992). In addition, murine models of GVHD (see Paul ed., *Fundamental Immunology,* Raven Press, New York, 1989, pp. 846–847) can be used to determine the effect of blocking B lymphocyte antigen function in vivo on the development of that disease.

Blocking B lymphocyte antigen function, e.g., by use of a peptide having B7-2 activity alone or in combination with a peptide having B7-1 activity and/or a peptide having B7-3 activity, may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology,* Raven Press, New York, 1989, pp. 840–856).

The IgE antibody response in atopic allergy is highly T cell dependent and, thus, inhibition of B lymphocyte antigen induced T cell activation may be useful therapeutically in the treatment of allergy and allergic reactions. An inhibitory form of B7-2 protein, such as a peptide having B7-2 activity alone or in combination with a peptide having the activity of another B lymphocyte antigen, such as B7-1, can be administered to an allergic subject to inhibit T cell mediated allergic responses in the subject. Inhibition of B lymphocyte antigen costimulation of T cells may be accompanied by exposure to allergen in conjunction with appropriate MHC molecules. Allergic reactions may be systemic or local in nature, depending on the route of entry of the allergen and the pattern of deposition of IgE on mast cells or basophils. Thus, it may be necessary to inhibit T cell mediated allergic responses locally or systemically by proper administration of an inhibitory form of B7-2 protein.

Inhibition of T cell activation through blockage of B lymphocyte antigen function may also be important therapeutically in viral infections of T cells. For example, in the acquired immune deficiency syndrome (AIDS), viral replication is stimulated by T cell activation. Blocking B7-2 function could lead to a lower level of viral replication and thereby ameliorate the course of AIDS. In addition, it may also be necessary to block the function of a combination of B lymphocyte antigens i.e., B7-1, B7-2 and B7-3. Surprisingly, HTLV-I infected T cells express B7-1 and B7-2. This expression may be important in the growth of HTLV-I infected T cells and the blockage of B7-1 function together with the function of B7-2 and/or B7-3 may slow the growth of HTLV-I induced leukemias. Alternatively, stimulation of viral replication by T cell activation may be induced by contact with a stimulatory form of B7-2 protein, for such purposes as generating retroviruses (e.g., various HIV isolates) in sufficient quantities for isolatation and use.

F. Therapeutic Uses by Upregulation of Immune Responses

Upregulation of a B lymphocyte antigen function, as a means of upregulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. Viral infections are cleared primarily by cytolytic T cells. In accordance with the present invention, it is believed that B7-2 and thus, B7-1 and B7-3 with their natural ligand(s) on T cells may result in an increase in the cytolytic activity of at least some T cells. It is also believed that B7-2, B7-1, and B7-3 are involved in the initial activation and generation of CD8+ cytotoxic T cells. The addition of a soluble peptide having B7-2 activity, alone, or in combination with a peptide having the activity of another B lymphocyte antigen, in a multi-valent form, to stimulate T cell activity through the costimulation pathway would thus be therapeutically useful in situations where more rapid or thorough clearance of virus would be beneficial. These would include viral skin diseases such as Herpes or shingles, in which cases the multi-valent soluble peptide having B7-2 activity or combination of such peptide and/or a peptide having B7-1 activity and/or a peptide having B7-3 activity is delivered topically to the skin. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide having B7-2 activity (alone or in combination with a peptide having B7-1 activity and/or a peptide having B7-3 activity) or together with a stimulatory form of a soluble peptide having B7-2 activity (alone or in combination with a peptide having B7-1 activity and/or a peptide having B7-3 activity) and reintroducing the in vitro activated T cells into the patient. Another method of enhancing anti-viral immune responses would be to isolate infected cells from a patient, transfect them with a nucleic acid encoding a peptide having the activity of a B lymphocyte antigen as described herein such that the cells express all or a portion of a B lymphocyte antigen on their surface, e.g., B7-2 or B7-3, and reintroduce the transfected cells into the patient. The infected cells would now be capable of delivering a costimulatory signal to, and thereby activate, T cells in vivo.

Stimulatory forms of B lymphocyte antigens may also be used prophylactically in vaccines against various pathogens. Immunity against a pathogen, e.g., a virus, could be induced by vaccinating with a viral protein along with a stimulatory form of a peptide having B7-2 activity or another peptide having the activity of B lymphocyte antigen in an appropriate adjuvant. Alternately, an expression vector which encodes genes for both a pathogenic antigen and a peptide having the activity of a B lymphocyte antigen, e.g., a vaccinia virus expression vector engineered to express a nucleic acid encoding a viral protein and a nucleic acid encoding a peptide having B7-2 activity as described herein, can be used for vaccination. Presentation of B7-2 with class I MHC proteins by, for example, a cell transfected to coexpress a peptide having B7-2 activity and MHC class I α chain protein and $\beta_2$ microglobulin may also result in activation of cytolytic CD8+ T cells and provide immunity from viral infection. Pathogens for which vaccines may be useful include hepatitis B, hepatitis C, Epstein-Barr virus, cytomegalovirus, HIV-1, HIV-2, tuberculosis, malaria and schistosomiasis.

In another application, upregulation or enhancement of B lymphocyte antigen function may be useful in the induction of tumor immunity. Tumor cells (e.g., sarcoma, melanoma, lymphoma, leukemia, neuroblastoma, carcinoma) transfected with a nucleic acid encoding at least one peptide having the activity of a B lymphocyte antigen, such as B7-2, can be administered to a subject to overcome tumor-specific tolerance in the subject. If desired, the tumor cell can be transfected to express a combination of peptides having the activity of a number of B lymphocyte antigens (e.g., B7-1, B7-2, B7-3). For example, tumor cells obtained from a patient can be transfected ex vivo with an expression vector directing the expression of a peptide having B7-2 activity alone, or in conjuction with a peptide having B7-1 activity and/or B7-3 activity. The transfected tumor cells are returned to the patient to result in expression of the peptides on the surface of the transfected cell. Alternatively, gene therapy techniques can be used to target a tumor cell for transfection in vivo.

The presence of the peptide having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Expression of B7-1 by B7 negative murine tumor cells has been shown to induce T cell mediated specific immunity accompanied by tumor rejection and prolonged protection to tumor challenge in mice (Chen, L., et al. (1992) *Cell* 71, 1093–1102; Townsend, S. E. and Allison, J. P. (1993) *Science* 259, 368–370; Baskar, S., et al. (1993) *Proc. Natl. Acad. Sci.* 90, 5687–5690). Thus, the induction of a T cell mediated immune response in a human subject may be sufficient to overcome tumor-specific tolerance in the subject.

In another aspect, a stimulatory form of one or more soluble peptides having an activity of a B lymphocyte antigen can be administered to a tumor-bearing patient to provide a costimulatory signal to T cells in order to induce anti-tumor immunity.

G. Administration of Therapeutic Forms of B Lymphocyte Antigens

The peptides of the invention are administered to subjects in a biologically compatible form suitable for pharmaceutical administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of a peptide having the activity of a novel B lymphocyte antigen as described herein can be in any pharmacological form including a therapeutically active amount of peptide alone or in combination with a peptide having the activity of another B lymphocyte antigen and a pharmaceutically acceptable carrier. Administration of a therapeutically active amount of the therapeutic compositions of the present invention is defined as an amount effective, at dosages and for periods of time necessary to achieve the desired result. For example, a therapeutically active amount of a peptide having B7-2 activity may vary according to factors such as the disease state, age, sex, and weight of the individual, and the ability of peptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., peptide) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a peptide having B7-2 activity by other than parenteral administration, it may be necessary to coat the peptide with, or co-administer the peptide with, a material to prevent its inactivation. For example, a peptide having B7-2 activity may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether.

Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., peptide having B7-2 activity) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

H. Identification of Cytokines Induced by Costimulation

The nucleic acid sequences encoding peptides having the activity of novel B lymphocyte antigens as described herein can be used to identify cytokines which are produced by T cells in response to stimulation by a form of B lymphocyte antigen, e.g., B7-2. T cells can be suboptimally stimulated in vitro with a primary activation signal, such as phorbol ester, anti-CD3 antibody or preferably antigen in association with an MHC class II molecule, and given a costimulatory signal by a stimulatory form of B7-2 antigen, for instance by a cell transfected with nucleic acid encoding a peptide having B7-2 activity and expressing the peptide on its surface or by a soluble, stimulatory form of the peptide. Known cytokines released into the media can be identified by ELISA or by the ability of an antibody which blocks the cytokine to inhibit T cell proliferation or proliferation of other cell types that is induced by the cytokine. An IL-4 ELISA kit is available from Genzyme (Cambridge Mass.), as is an IL-7 blocking antibody. Blocking antibodies against IL-9 and IL-12 are available from Genetics Institute (Cambridge, Mass.).

An in vitro T cell costimulation assay as described above can also be used in a method for identifying novel cytokines which may be induced by costimulation. If a particular activity induced upon costimulation, e.g., T cell proliferation, cannot be inhibited by addition of blocking antibodies to known cytokines, the activity may result from the action of an unknown cytokine. Following costimulation, this cytokine could be purified from the media by conventional methods and its activity measured by its ability to induce T cell proliferation.

To identify cytokines which prevent the induction of tolerance, an in vitro T cell costimulation assay as described above can be used. In this case, T cells would be given the primary activation signal and contacted with a selected cytokine, but would not be given the costimulatory signal. After washing and resting the T cells, the cells would be rechallenged with both a primary activation signal and a costimulatory signal. If the T cells do not respond (e.g., proliferate or produce IL-2) they have become tolerized and the cytokine has not prevented the induction of tolerance. However, if the T cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a B7-2 blocking reagent together with a cytokine blocking antibody to a subject.

I. Identification of Molecules which Inhibit Costimulation

Another application of the peptide having the activity of a novel B lymphocyte antigen of the invention (e.g., B7-2 and B7-3) is the use of one or more of these peptides in screening assays to discover as yet undefined molecules which are inhibitors of costimulatory ligand binding and/or of intracellular signaling through T cells following costimulation. For example, a solid-phase binding assay using a peptide having the activity of a B lymphocyte antigen, such as B7-2, could be used to identify molecules which inhibit binding of the antigen with the appropriate T cell ligand (e.g., CTLA4, CD28). In addition, an in vitro T cell costimulation assay as described above could be used to identify molecules which interfere with intracellular signaling through the T cells following costimulation as determined by the ability of these molecules to inhibit T cell proliferation and/or cytokine production (yet which do not prevent binding of B lymphocyte antigens to their receptors). For example, the compound cyclosporine A inhibits T cell activation through stimulation via the T cell receptor pathway but not via the CD28/CTLA4 pathway. Therefore, a different intracellular signaling pathway is involved in costimulation. Molecules which interfere with intracellular signaling via the CD28/CTLA4 pathway may be effective as immunosuppressive agents in vivo (similar to the effects of cyclosporine A).

J. Identification of Molecules which Modulate B Lymphocyte Antigen Expression

The monoclonal antibodies produced using the proteins and peptides of the current invention can be used in a screening assay for molecules which modulate the expression of B lymphocyte antigens on cells. For example, molecules which effect intracellular signaling which leads to induction of B lymphocyte antigens, e.g. B7-2 or B7-3, can be identified by assaying expression of one or more B lymphocyte antigens on the cell surface. Reduced immunofluorescent staining by an anti-B7-2 antibody in the presence of the molecule would indicate that the molecule inhibits intracellular signals. Molecules which upregulate B lymphocyte antigen expression result in an increased immunofluorescent staining. Alternatively, the effect of a molecule on expression of a B lymphocyte antigen, such as B7-2, can be determined by detecting cellular B7-2 mRNA levels using a B7-2 cDNA as a probe. For example, a cell which expresses a peptide having B7-2 activity can be contacted with a molecule to be tested, and an increase or decrease in B7-2 mRNA levels in the cell detected by standard technique, such as Northern hybridization analysis or conventional dot blot of mRNA or total poly($A^+$)RNAs using a B7-2 CDNA probe labeled with a detectable marker. Molecules which modulate B lymphocyte antigen expression may be useful therapeutically for either upregulating or downregulating immune responses alone or in conjunction with soluble blocking or stimulating reagents. For instance, a molecule which inhibits expression of B7-2 could be administered together with a B7-2 blocking reagent for immunosuppressive purposes. Molecules which can be tested in the above-described assays include cytokines such as IL-4, γINF, IL-10, IL-12, GM-CSF and prostagladins.

This invention is further illustrated by the following examples which should not be construed as limiting. The contents of all references and published patent applications cited throughout this application are hereby incorporated by reference.

The following methodology was used in Examples 1, 2 and 3.

METHODS AND MATERIALS

A. Cells

Mononuclear cells were isolated by Ficoll-Hypaque density gradient centrifugation from single cell suspensions of normal human spleens and were separated into E− and E+ fractions by resetting with sheep red blood cells (Boyd, A. W., et al. (1985) *J. Immunol.* 134, 1516). B cells were purified from the E− fraction by adherence of monocytes on plastic and depletion of residual T, natural killer cells (NK) and residual monocytes by two treatments with anti-MsIgG and anti-MsIgM coated magnetic beads (Advanced Magnetics, Cambridge, Mass.), using monoclonal antibodies: anti-CD4, -CD8, -CD11b,-CD14 and -CD16. CD4+ T cells were isolated from the E+ fraction of the same spleens after adherence on plastic and depletion of NK, B cells and residual monocytes with magnetic beads and monoclonal antibodies: anti-CD20, -CD11b, -CD8 and -CD16. CD28+ T cells were identically isolated from the E+ fraction using anti-CD20, -CD11b, -CD 14 and -CD16 monoclonal antibodies. The efficiency of the purification was analyzed by indirect immunofluorescence and flow cytometry using an EPICS flow cytometer (Coulter). B cell preparations were >95% CD20+, <2% CD3+, <1% CD14+. CD4+ T cell preparations were >98% CD3+, >98% CD4+, <1% CD8+, <1% CD20+, <1% CD14+. CD28+ T cell preparations were >98% CD3+, >98% CD28+, <1% CD20+, <1% CD14+.

B. Monoclonal Antibodies and Fusion Proteins

Monoclonal antibodies were used as purified Ig unless indicated otherwise: anti-B7:133, IgM is a blocking antibody and has been previously described (Freedman, A. S. et al. (1987) *Immunol.* 137, 3260–3267); anti-B7:B1.1, IgGI (RepliGen Corp., Cambridge, Mass.) (Nickoloff, B., et al (1993) *Am. J. Pathol.* 142, 1029–1040) is a non-blocking monoclonal antibody; BB-1:IgM is a blocking antibody (Dr. E. Clark, University of Washington, Seattle, Wash.) (Yokochi, T., et al. (1982) *J. Immunol.* 128, 823–827); anti-CD20: B1, IgG2a (Stashenko, P., et al. (1980) *J. Immunol.* 125, 1678–1685); anti-B5: IgM (Freedman, A., et al. (1985) *J. Immunol* 134, 2228–2235); anti-CD8: 7PT 3F9, IgG2a; anti-CD4: 19Thy5D7, IgG2a; anti-CD11b: Mol, IgM and anti-CD14: Mo2, IgM (Todd, R, et al. (1981) *J. Immunol.* 126, 1435–1442); anti-MHC class II: 9–49, IgG2a (Dr R. Todd, University of Michigan, Ann Arbor) (Todd, R. I., et al. (1984) *Hum Immunol.* 10, 23–40; anti-CD28: 9.3, IgG2a (Dr. C. June, Naval Research Institute, Bethesda) (Hansen, J. A., et al. (1980) *Immunogenetics.* 10, 247–260); anti-CD16: 3G8, IgG1 (used as ascites) (Dr. J. Ritz, Dana-Farber Cancer Institute, Boston); anti-CD3: OKT3, IgG2a hybridoma was obtained from the American Type Culture Collection and the purified monoclonal antibody was adhered on plastic plates at a concentration of 1 μg/ml; anti-CD28 Fab fragments were generated from the 9.3 monoclonal antibody, by papain digestion and purification on a protein A column, according to the manufacturer's instructions (Pierce, Rockford, Ill.). Human CTLA4 fusion protein (CTLA4Ig) and control fusion protein (control-Ig) were prepared as previously described (Gimmi, C. D., et al. (1993) *Proc. Natl. Acad. Sci USA* 90:6586–6590); Boussiotis, V., et al *J. Exp. Med.* (accepted for publication)).

C. CHO Cell Transfection

B7-1 transfectants (CHO-B7) were prepared from the B7-1 negative chinese hamster ovary (CHO) cell line, fixed with paraformaldehyde and used as previously described (Gimmi, C. D., et al. *Proc. Natl. Acad. Sci USA* 88, 6575–6579).

D. In Vitro B Cell Activation and Selection of B7+ and B7− Cells

Splenic B cells were cultured at $2\times10^6$ cells/ml in complete culture media, {RPMI 1640 with 10% heat inactivated fetal calf serum (FCS), 2 mM glutamine, 1 mM sodium pyruvate, penicillin (100 units/ml), streptomycin sulfate (100 μg/ml) and gentamycin sulfate (5 μg/ml)}, in tissue culture flasks and were activated by crosslinking of slg with affinity purified rabbit anti-human IgM coupled to Affi-Gel 702 beads (Bio-Rad), Richmond, Calif.) (Boyd, A. W., et al., (1985) *J. Immunol.* 134,1516) or by crosslinking of MHC class II with 9–49 antibody coupled to Affi-Gel 702 beads. B cells activated for 72 hours, were used as total activated B cell populations or were indirectly stained with anti-B7 (B 1.1) monoclonal antibody and fluorscein isothiocyanate (FITC) labeled goat anti-mouse immunoglobulin (Fisher, Pittsburgh, PA), and fractionated into B7-1+ and B7-1− populations by flow cytometric cell sorting (EPICS Elite flow cytometer, Coulter).

E. Immunoflouorescence and Flow Cytometry

For surface phenotype analysis populations of B cells activated by either sIg or MHC class II crosslinking for 6, 12, 24, 48, 72 and 96 hours were stained with either anti-B7 (133), BB-1 monoclonal antibodies, control IgM antibody, CTLA4Ig or control-Ig. Cell suspensions were stained by two step indirect membrane staining with 10 µg/ml of primary monoclonal antibody followed by the appropriate secondary reagents. Specifically, immunoreactivity with anti-B7 (133) and BB-1 monoclonal antibodies was studied by indirect staining using goat anti-mouse Ig or immunoglobulin FITC (Fisher) as secondary reagent and immunoreactivity with fusion proteins was studied using biotinylated CTLA4Ig or biotinylated control-Ig and streptavidin-phycoerythrin as secondary reagent. PBS containing 10% AB serum was used as diluent and wash media. Cells were fixed with 0.1% paraformaldehyde and analyzed on a flow cytometer (EPICS Elite Coulter).

F. Proliferation Assay

T cells were cultured at a concentration of 1×10$^5$ cells per well in 96-well flat bottom microtiter plate at 37° C. for 3 days in 5% CO$_2$. Syngeneic activated B cells (total B cell population or B7+ and B7− fractions) were irradiated (2500 rad) and added into the cultures at a concentration of 1×10$^5$ cells per well. Factors under study were added to the required concentration for a total final volume of 200 µl per well. When indicated, T cells were incubated with anti-CD28 Fab (final concentration of 10 µg/ml), for 30 minutes at 4° C., prior to addition in experimental plates. Similarly, CHO-B7 or B cells were incubated with CTLA4Ig or control-Ig (10 µg/ml) for 30 minutes at 4° C.. Thymidine incorporation as an index of mitogenic activity, was assessed after incubation with 1 µCi (37 kBq) of {methyl-$^3$H} thymidine (Du Pont, Boston, Mass.) for the last 15 hours of the culture. The cells were harvested onto filters and the radioactivity on the dried filters was measured in a Pharmacia beta plate liquid scintillation counter.

G. IL-2 and IL-4 Assay

IL-2 and IL-4 concentrations were assayed by ELISA (R&D Systems, Minneapolis, Minn. and BioSource, Camarillo, Calif.) in culture supernatants collected at 24 hours after initiation of the culture.

EXAMPLE 1
Expression of a Novel CTLA4 Ligand on Activated B Cells Which Induces T Cell Proliferation Since crosslinking surface Ig induces human resting B cells to express B7-1 maximally (50–80%) at 72 hours, the ability of activated human B lymphocytes to induce submitogenically activated T cells to proliferate and secrete IL-2 was determined. FIG. 1 depicts the costimulatory response of human splenic CD28$^+$ T cells, submitogenically activated with anti-CD3 monoclonal antibody, to either B7 (B7-1) transfected CHO cells (CHO-B7) or syngeneic splenic B cells activated with anti-Ig for 72 hours. $^3$H-Thymidine incorporation was assessed for the last 15 hours of a 72 hours culture. IL-2 was assessed by ELISA in supernatants after 24 hours of culture (Detection limits of the assay: 31–2000 pg/ml). FIG. 1 is representative of seventeen experiments.

Submitogenically activated CD28+ T cells proliferated and secreted high levels of IL-2 in response to B7-1 costimulation provided by CHO-B7 (FIG. 1, panel a). Both proliferation and IL-2 secretion were totally inhibited by blocking the B7-1 molecule on CHO cells with either anti-B7-1 monoclonal antibody or by a fusion protein for its high affinity receptor, CTLA4. Similarly, proliferation and IL-2 secretion were abrogated by blocking B7-1 signalling via CD28 with Fab anti-CD28 monoclonal antibody. Control monoclonal antibody or control fusion protein had no effect. Nearly identical costimulation of proliferation and IL-2 secretion was provided by splenic B cells activated with anti-Ig for 72 hours (panel b). Though anti-B7-1 monoclonal antibody could completely abrogate both proliferation and IL-2 secretion delivered by CHO-B7, anti-B7-1 monoclonal antibody consistently inhibited proliferation induced by activated B cells by only 50% whereas IL-2 secretion was totally inhibited. In contrast to the partial blockage of proliferation induced by anti-B7-1 monoclonal antibody, both CTLA4Ig and Fab anti-CD28 monoclonal antibody completely blocked proliferation and IL-2 secretion. These results are consistent with the hypothesis that activated human B cells express one or more additional CTLA4/CD28 ligands which can induce T cell proliferation and IL-2 secretion.

EXAMPLE 2
Activated Human Splenic B Cells Express CTLA4 Ligand (s) Distinct from B7-1

Figure 2B:
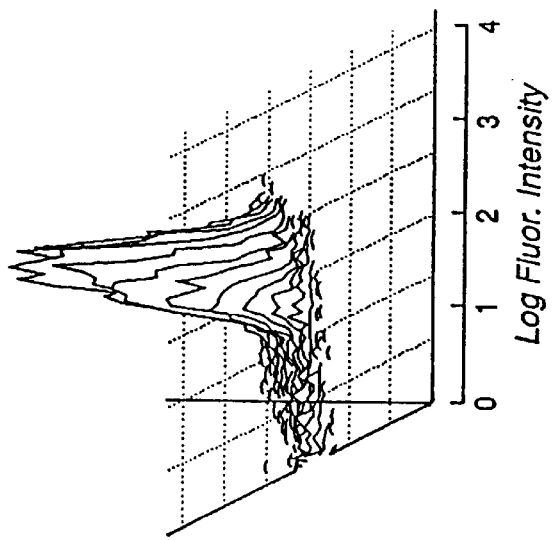
Figure 2C:
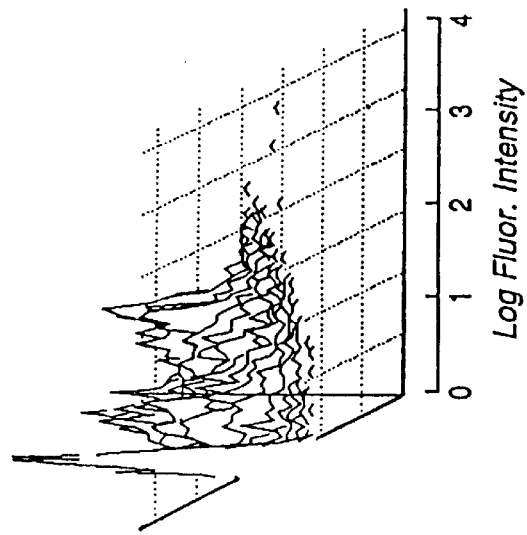

In light of the above observations, whether other CTLA4 binding counter-receptors were expressed on activated B cells was determined. To this end, human splenic B cells were activated for 72 hours with anti-Ig and then stained with an anti-B7-1 monoclonal antibody (B 1.1) which does not inhibit B7-1 mediated costimulation. Fluoroscein isothiocyanate (FITC) and mAb B 1.1 were used with flow cytometric cell sorting to isolate B7-1$^+$ and B7$^-$ fractions. The resulting post-sort positive population was 99% B7-1$^+$ and the post-sort negative population was 98% B7-1$^-$ (FIG. 2).

Figure 3A:
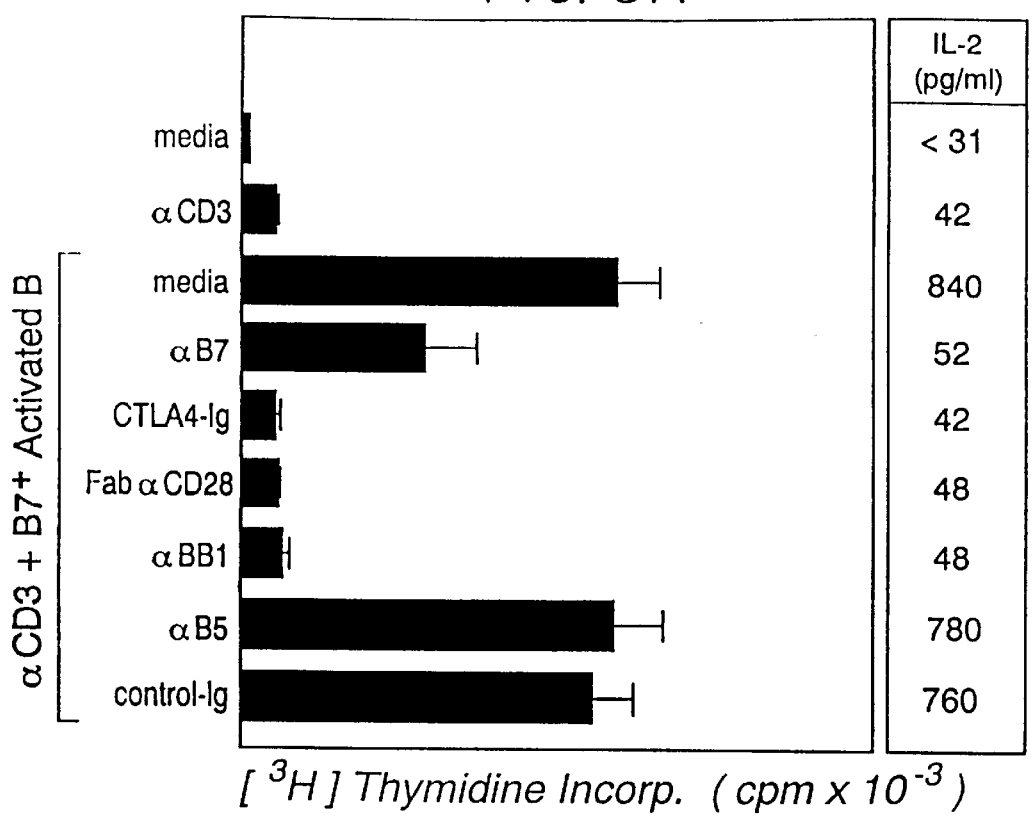
FIGS. 3A–B are graphic representations of the responses of $CD28^+$ T cells, as assessed by $^3$H-thymidine incorporation and IL-2 secretion, to costimulation provided by $B7-1^+$ (panel a) or B7-1- (panel b) activated syngeneic B lymphocytes cultured in media, anti-CD3 alone, or anti-CD3 in the presence of the following monoclonal antibodies or recombinant proteins: αBB-1 (133, anti-B7-1 and anti-B7-3); αB7 (anti-B7-1); CTLA4Ig; Fab αCD28; control Ig fusion protein or αB5 (anti-B5).
Figure 3B:
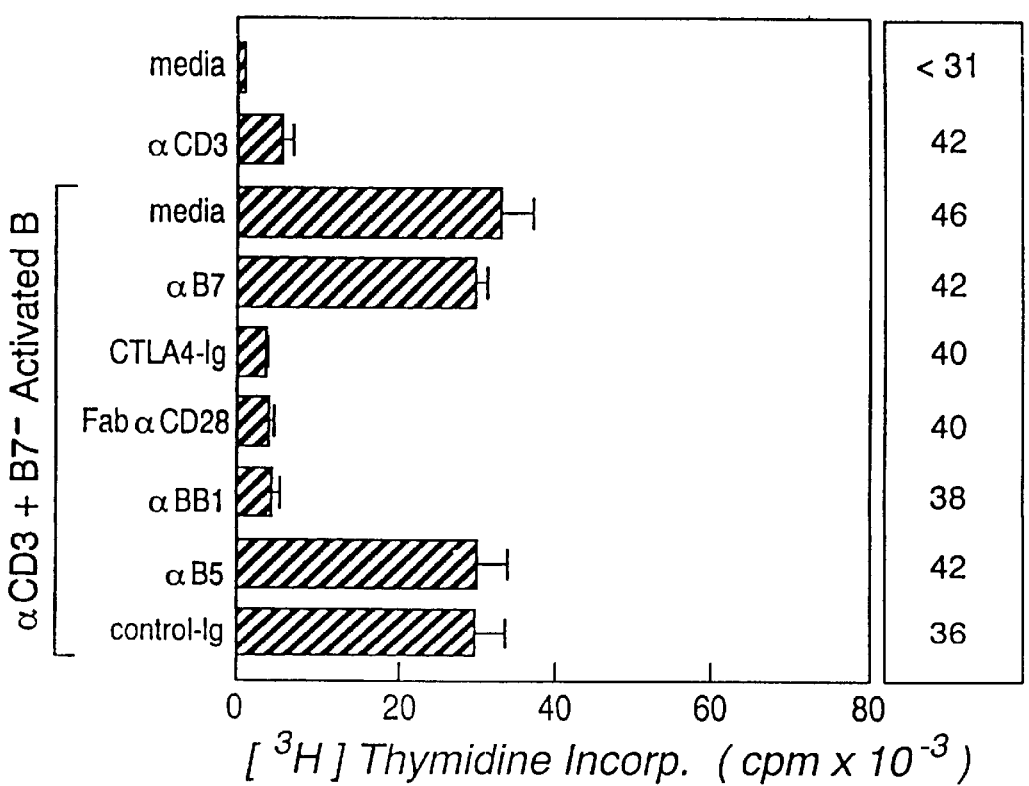

To examine the costimulatory potential of each population, human splenic CD28+ T cells were submitogenically stimulated with anti-CD3 monoclonal antibody in the presence of irradiated B7-1+ or B7-1− anti-Ig activated (72 hours) splenic B cells. $^3$H-Thymidine incorporation was assessed for the last 15 hours of a 72 hours culture. IL-2 was assessed by ELISA in supernatants after 24 hours of culture (Detection limits of the assay: 31–2000 pg/ml). The results of FIG. 3 are representative of ten experiments. B7-1+ B cells induced anti-CD3 activated T cells to proliferate and secrete IL-2 (FIG. 3a) but not IL-4. As was observed with the unfractionated activated B cell population, anti-B7-1 monoclonal antibody (133) inhibited proliferation only 50% but consistently abrogated IL-2 secretion. As above, CTLA4Ig binding or blockade of CD28 with Fab anti-CD28 monoclonal antibody completely inhibited both proliferation and IL-2 secretion. Control monoclonal antibody and control-Ig were not inhibitory. In an attempt to identify other potential CTLA4/CD28 binding costimulatory ligand(s) which might account for the residual, non-B7 mediated proliferation delivered by B7+ B cells, the effect of BB-1 monoclonal antibody on proliferation and IL-2 secretion was examined. As seen, BB-1 monoclonal antibody completely inhibited both proliferation and IL-2 secretion (FIG. 3a). FIG. 3b displays the costimulatory potential of B7-1- activated human splenic B cells. Irradiated B7-1- activated (72 hr) B cells could also deliver a significant costimulatory signal to submitogenically activated CD4+ lymphocytes. This costimulation was not accompanied by detectable IL-2 (FIG. 3b) or IL-4 accumulation and anti-B7-1 monoclonal antibody did not inhibit proliferation. However, CTLA4Ig, Fab anti-CD28 monoclonal antibody, and BB-1 monoclonal antibody all completely inhibited proliferation.

Figure 4:
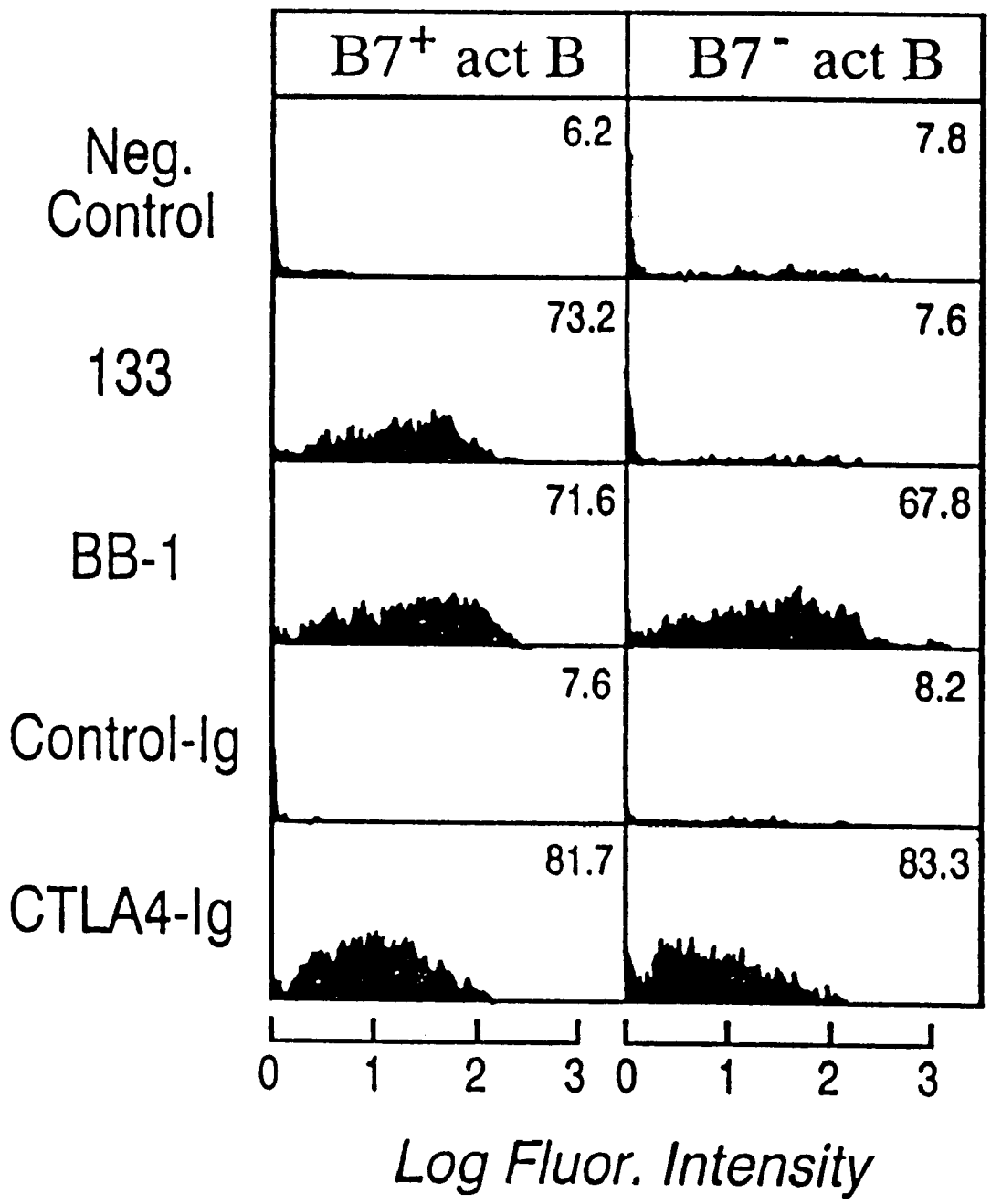
FIG. 4 is a graphic representation of the cell surface expression of B7-1, B7-3 and total CTLA4 counter-receptors on fractionated B7-1$^+$ and B7-1$^-$ activated B lymphocytes.

Phenotypic analysis of the B7-1+ and B7-1− activated splenic B cells confirmed the above functional results. FIG. 4 shows the cell surface expression of B7-1, B7-2 and B7-3 on fractionated B7-1$^+$ and B7-1$^−$ activated B cell. As seen in FIG. 4, B7-1+ activated splenic B cells stained with anti-B7-1 (133) monoclonal antibody, BB-1 monoclonal antibody, and bound CTLA4-Ig. In contrast, B7− activated splenic B cells did not stain with anti-B7-1 (133) monoclonal antibody but did stain with BB-1 monoclonal antibody and CTLA4Ig. These phenotypic and functional results demonstrate that both B7-1+ and B7-1-activated (72 hours) human B lymphocytes express CTLA4 binding counter-receptor(s) which: 1) can induce submitogenically activated T cells to proliferate without detectable IL-2 secretion; and 2) are identified by the BB-1 monoclonal antibody but not anti-B7-1 monoclonal antibody. Thus, these CTLA4/CD28 ligands can be distinguished on the basis of their temporal expression after B cell activation and their reactivity with CTLA4Ig and anti-B7 monoclonal antibodies. The results of FIG. 4 are representative of five experiments.

Figure 5:
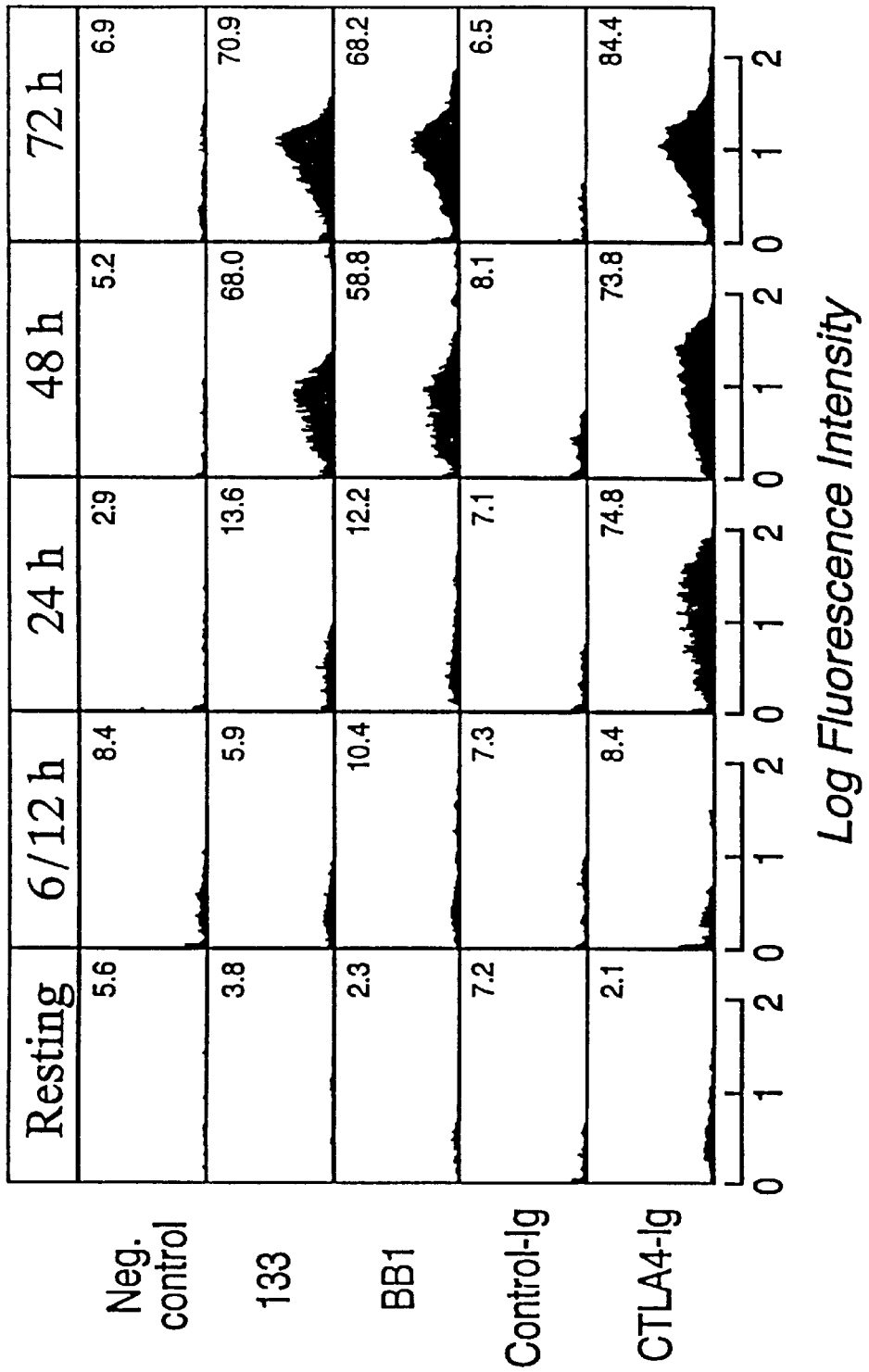
FIG. 5 is a graphic representation of temporal surface expression of B7-1 (CTLA4Ig and mAbs BB-1 and 133), B7-3 (CTLA4Ig and mAb BB1) and B7-2 (CTLA4Ig) counter-receptors on splenic B cells activated by sIg crosslinking.
Figure 6:
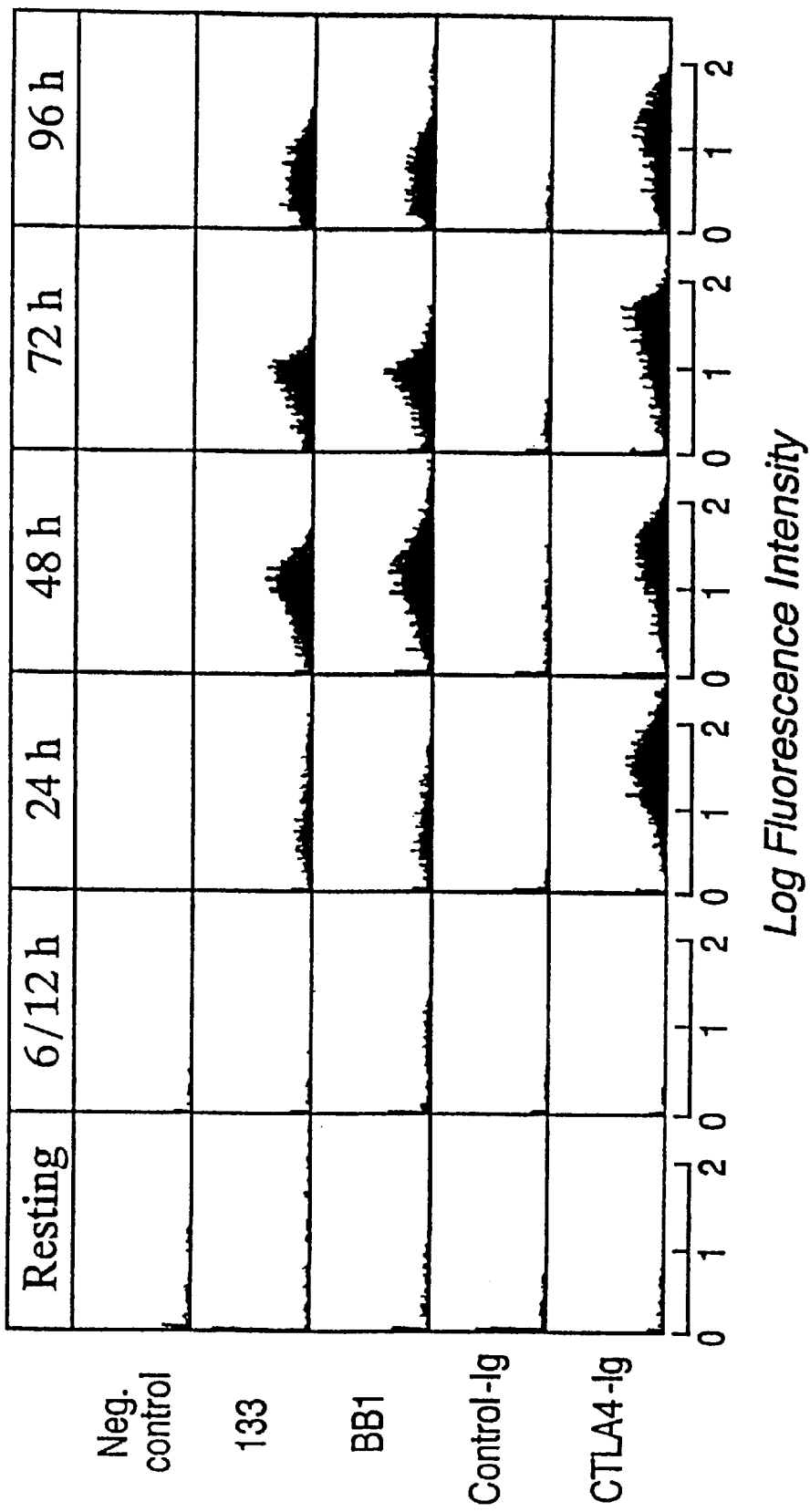
FIG. 6 is a graphic representation of temporal surface expression of B7-1 (CTLA4Ig and mAbs BB-1 and 133), B7-3 (CTLA4Ig and mAb BB1) and B7-2 (CTLA4Ig) counter-receptors on splenic B cells activated by MHC class II crosslinking.

EXAMPLE 3
Three Distinct CTLA4/CD28 Ligands Are Expressed Following Human B Cell Activation To determine the sequential expression of CTLA4 binding counter-receptors following activation, human splenic B cells were activated by crosslinking of either surface Ig or MHC class II and the expression of B7-1, B7-3 and B7-2 binding proteins were examined by flow cytometric analysis. Ig or MHC class II crosslinking induced a similar pattern of CTLA4Ig binding (FIGS. 5 and 6). FIG. 5 is representative of the results of 25 experiments for anti-137-1 and BB-1 binding and 5 experiments for CTLA4Ig binding. FIG. 6 is representative of 25 experiments for anti-B7-1 binding and 5 experiments for CTLA4Ig binding. The results of these experiments indicates that prior to 24 hours, none of these molecules are expressed. At 24 hours post-activation, the majority of cells express a protein that binds CTLA4Ig (B7-2), however, fewer than 20% express either B7-1 or B7-3. Crosslinking of MHC class II induces maximal expression and intensity of B7-1 and B7-3 at 48 hours whereas crosslinking of Ig induces maximal expression at 72 hours and expression declines thereafter. These results suggest that an additional CTLA4 binding counter-receptor is expressed by 24 hours and that the temporal expression of the distinct B7-1 and B7-3 proteins appears to coincide.

A series of experiments was conducted to determine whether the temporal expression of CTLA4 binding counter-receptors differentially correlated with their ability to costimulate T cell proliferation and/or IL-2 secretion. Human splenic CD28+ T cells submitogenically stimulated with anti-CD3 were cultured for 72 hours in the presence of irradiated human splenic B cells that had been previously activated in vitro by sIg crosslinking for 24, 48, or 72 hours. IL-2 secretion was assessed by ELISA in supernatants after 24 hours and T cell proliferation as assessed by $^3$H-thymidine incorporation for the last 15 hours of a 72 hour culture. The results of FIG. 7 are representative of 5 experiments. As seen in FIG. 7a, 24 hour activated B cells provided a costimulatory signal which was accompanied by modest levels of IL-2 production, although the magnitude of proliferation was significantly less than observed with 48 and 72 hours activated human B cells (note differences in scale for $^3$H-Thymidine incorporation). Neither proliferation nor IL-2 accumulation was inhibited by anti-B7-1 (133) or BB-1. In contrast, with CTLA4Ig and anti-CD28 Fab monoclonal antibody totally abrogated proliferation and IL-2 accumulation. B cells activated for 48 hours, provided costimulation which resulted in nearly maximal proliferation and IL-2 secretion (FIG. 7b). Here, anti-B7-1 (133) monoclonal antibody, inhibited proliferation approximately 50% but totally blocked IL-2 accumulation. BB-1 monoclonal antibody totally inhibited both proliferation and IL-2 secretion. As above, CTLA4Ig and Fab anti-CD28 also totally blocked proliferation and IL-2 production. Finally, 72 hour activated B cells induced T cell response identical to that induced by 48 hour activated B cells. Similar results are observed if the submitogenic signal is delivered by phorbol myristic acid (PMA) and if the human splenic B cells are activated by MHC class II rather than Ig crosslinking. These results indicate that there are three CTLA4 binding molecules that are temporarily expressed on activated B cells and each can induce submitogenically stimulated T cells to proliferate. Two of these molecules, the early CTLA4 binding counter-receptor (B7-2) and B7-1 (133) induce IL-2 production whereas B7-3 induces proliferation without detectable IL-2 production.

Previous studies provided conflicting evidence whether the anti-B7 monoclonal antibody,133 and monoclonal antibody BB-l identified the same molecule (Freedman, A. S. et al. (1987) *Immunol*. 137, 3260–3267; Yokochi, T., et al. (1982) *J. Immunol* 128, 823–827; Freeman, G. J., et al. (1989) *J. Immunol*. 143, 2714–2722.). Although both monoclonal antibodies identified molecules expressed 48 hours following human B-cell activation, several reports suggested that B7 (B7-1) and the molecule identified by monoclonal antibody BB-1 were distinct since they were differentially expressed on cell lines and B cell neoplasms (Freedman, A. S. et al. (1987) *Immunol*. 137, 3260–3267; Yokochi, T., et al. (1982) *J. Immunol*. 128, 823–827; Freeman, G. J., et al. (1989) *J. Immunol*. 143, 2714–2722; Clark, E and Yokochi, T. (1984) *Leukocyte Typing, 1st International References Workshop*. 339–346; Clark, E., et al. (1984) *Leukocyte Typing, 1st International References Workshop*. 740). In addition, immunoprecipitation and Western Blotting with these IgM monoclonal antibodies suggested that they identified different molecules (Clark, E and Yokochi, T. (1984) *Leukocyte Typing, 1st International References Workshop*. 339–346; Clark, E., et al. (1984) *Leukocyte Typing, 1st International References Workshop*. 740). The original anti-B7 monoclonal antibody, 133, was generated by immunization with anti-immunoglobulin activated human B lymphocytes whereas the BB-1 monoclonal antibody was generated by immunization with a baboon cell line. Thus, the BB-1 monoclonal antibody must identify an epitope on human cells that is conserved between baboons and humans.

Following the molecular cloning and expression of the human B7 gene (B7-1), B7 transfected COS cells were found to be identically stained with the anti-B7 (133) and BB-1 monoclonal antibodies and that they both precipitated the identical broad molecular band (44–54 kD) strongly suggesting that they identified the same molecule (Freeman, G. J., et al. (1989) *J. Immunol*. 143, 2714–2722). This observation was unexpected since the gene encoding the molecule identified by the BB-1 monoclonal antibody had been previously mapped to chromosome 12 (Katz, F. E., et al. (1985) *Eur. J. Immunol.* 103–6), whereas the B7 gene was located by two groups on chromosome 3 (Freeman, G. J., et al. (1992) *Blood.* 79, 489–494; Selvakumar, A., et al. (1992) *Immunogenetics* 36, 175–181.). Subsequently, additional discrepancies between the phenotypic expression of B7 (B7-1) and the molecule identified by the BB-1 monclonal antibody were noted. BB-1 monoclonal antibody stained thymic epithelial cells (Turka, L. A., et al. (1991) *J. Immunol.* 146, 1428–36; Munro, J. M., et al. *Blood* submitted.) and keratinocytes (Nickoloff, B., et al (1993) *Am. J. Pathol.* 142, 1029–1040; Augustin, M., et al. (1993) *J. Invest. Dermatol.* 100, 275–281.) whereas anti-B7 did not. Recently, Nickoloff et al. (1993) *Am. J. Pathol.* 142, 1029–1040, reported discordant expression of the molecule identified by the BB-1 monoclonal antibody and B7 on keratinocytes using a BB-1 and anti-B7 (B 1.1 and 133) monoclonal antibodies. Nickoloff et al. also demonstrated that these BB-1 positive cells did not express B7 mRNA yet bound CD28 transfected COS cells providing further support for the existence of a distinct protein which binds monoclonal antibody BB-1.

The present findings confirm that there is an additional CTLA4 counter-receptor identified by the BB-1 monoclonal antibody, B7-3, and that this protein appears to be functionally distinct from B7-1 (133). Although the expression of B7-1 and B7-3 following B cell activation appears to be concordant on B7 positive B cells, these studies demonstrate that the B7-3 molecule is also expressed on B7 negative activated B cells. More importantly, the B7-3 molecule appears to be capable of inducing T cell proliferation without detectable IL-2 or IL-4 production. This result is similar to the previous observation that ICAM-1 could costimulate T cell proliferation without detectable IL-2 or IL-4 production (Boussiotis, V., et al *J. Exp. Med.* (accepted for publication)). These data indicate that the BB-1 monoclonal antibody recognizes an epitope on the B7-1 protein and that this epitope is also found on a distinct B7-3 protein, which also has costimulatory function. Phenotypic and blocking studies demonstrate that the BB-1 monoclonal antibody could detect one (on B7 negative cells) or both (on B7 positive cells) of these proteins. In contrast, the anti-B7 monoclonal antibodies, 133 and B 1.1 detect only the B7-1 protein. Taken together, these results suggest that by 48 hours post B-cell activation by crosslinking of surface immunoglobulin or MHC class II, B cells express at least two distinct CTLA4 binding counter-receptors, one identified by both anti-B7 and BB-1 monclonal antibodies and the other identified only by BB-1 monoclonal antibody.

The B7-2 antigen is not detectable on activated B cells after 12 hours, but by 24 hours it is strongly expressed and functional. This molecule appears to signal via CD28 since proliferation and IL-2 production are completely blocked by Fab anti-CD28 monoclonal antibody. At 48 hours post activation, IL-2 secretion seems to be accounted for by B7-1 costimulation, since anti-B7 monoclonal antibody completely inhibits IL-2 production.

Previous studies and results presented here demonstrate that B7 (B7-1) is neither expressed (Freedman, A. S. et al. (1987) *Immunol.* 137, 3260–3267; Freedman, A. S., et al. (1991) *Cell. Immunol.* 137, 429–437) nor capable of costimulating T cell proliferation or IL-2 secretion until 48 hours post B-cell activation. Previous studies have shown that activation of T cells via the TCR in the absence of costimulation (Gimmi, C. D., et al. (1993) *Proc. Natl. Acad. Sci USA* 90:6586–6590; Schwartz, R. H., et al. (1989) *Cold Spring Harb. Symp. Quant. Biol* 54, 605–10; Beverly, B., et al. (1992) *Int. Immunol.* 4, 661–671.) and lack of IL-2 (Boussiotis, V., et al *J. Exp. Med.* (submitted); Beverly, B., et al. (1992) *Int. Immunol.* 4, 661–671; Wood, M., et al. (1993) *J. Exp. Med.* 177, 597–603) results in anergy. If B7-1 were the only costimulatory molecule capable of inducing IL-2 secretion, T cells would be anergized within the first 24 hours following activation since there is no B7-1 present to costimulate IL-2 production. Therefore, the existence of another, early inducible costimulatory molecule, which can costimulate IL-2 secretion during the first 24 hours would be necessary to induce an effective immune response rather than anergy. The appearance of the early CTLA4 binding counter-receptor, B7-2, between 12 and 24 hours post B cell activation, fulfills this function.

Two observations shed light on the biologic and potential clinical significance of these two additional CTLA4 binding counter-receptors. First, B7 (B7-1) deficient mouse has been developed and its antigen presenting cells were found to still bind CTLA4Ig (Freeman and Sharpe manuscript in preparation). This mouse is viable and isolated mononuclear cells induce detectable levels of IL-2 when cultured with T cells in vitro. Therefore, an alternative CD28 costimulatory counter-receptor or an alternative IL-2 producing pathway must be functional. Second, thus far the most effective reagents to induce antigen specific anergy in murine and human systems are CTLA4Ig and Fab anti-CD28, whereas anti-B7 monoclonal antibodies have been much less effective (Harding, F. A., et al. (1992) *Nature.* 356, 607–609; Lenschow, D. J., et al. (1992) *Science.* 257, 789–792; Chen, L., et al. (1992) *Cell.* 71, 1093–1102; Tan, P., et al. (1993) *J. Exp. Med.* 177, 165–173.). These observations are also consistent with the hypothesis that alternative CTLA4/CD28 ligands capable of inducing IL-2 exist, and taken together with the results presented herein, suggest that all three CTLA4 binding counter-receptors may be critical for the induction of T cell immunity. Furthermore, their blockade will likely be required for the induction of T cell anergy. Identical results have been observed in the murine system with the identification of two CTLA4 binding ligands, corresponding to the human B7-1 and B7-2 molecules. APCs in the B7 deficient mouse bind to the CTLA4 and can induce IL-2 secretion. Taken together, these observations indicate that multiple CTLA-4 binding counter-receptors exist and sequentially costimulate T cell activation in the murine system.

EXAMPLE 4

Cloning, Sequencing and Expression of the B7-2 Antigen

A. Construction of cDNA Library

A cDNA library was constructed in the pCDM8 vector (Seed, *Nature,* 329:840 (1987)) using poly (A)$^+$ RNA from the human anti-IgM activated B cells as described (Aruffo et al., *Proc. Natl. Acad. Sci. USA,* 84:3365 (1987)). Splenic B cells were cultured at $2\times10^6$ cells/ml in complete culture media, {RPMI 1640 with 10% heat inactivated fetal calf serum (FCS), 2 mM glutamine, 1 mM sodium pyruvate, penicillin (100 units/ml), streptomycin sulfate (100 µg/ml) and gentamycin sulfate (5 µg/ml)}, in tissue culture flasks and were activated by crosslinking of sIg with affinity purified rabbit anti-human IgM coupled to Affi-Gel 702 beads (Bio-Rad), Richmond, Calif.) (Boyd, A. W., et al., (1985) *J. Immunol.* 134,1516). Activated B cells were harvested after ⅙, ½, 4, 8 12, 24, 48, 72 and 96 hours.

RNA was prepared by homogenizing activated B cells in a solution of 4M guanidine thiocyanate, 0.5% sarkosyl, 25 mM EDTA, pH 7.5, 0.13% Sigma anti-foam A, and 0.7% mercaptoethanol. RNA was purified from the homogenate by centrifugation for 24 hour at 32,000 rpm through a solution of 5.7M CsCl, 10 mM EDTA, 25mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)$^+$ RNA used in cDNA library construction was purified by two cycles of oligo (dT)-cellulose selection.

Complementary DNA was synthesized from 5.5 μg of anti-IgM activated human B cell poly(A)$^+$ RNA in a reaction containing 50 mM Tris, pH 8.3, 75 mM KCl, 3 mM MgCl$_2$, 10 mM dithiothreitol, 500 μM dATP, dCTP, dGTP, dTTP, 50 μg/ml oligo(dT)$_{12-18}$, 180 units/ml RNasin, and 10,000 units/ml Moloney-MLV reverse transcriptase in a total volume of 55 μl at 37° for 1 hr. Following reverse transcription, the cDNA was converted to double-stranded DNA by adjusting the solution to 25 mM Tris, pH 8.3, 100 mM KCl, 5 mM MgCl$_2$, 250 μM each dATP, dCTP, dGTP, dTTP, 5 mM dithiothreitol, 250 units/ml DNA polymerase I, 8.5 units/ml ribonuclease H and incubating at 16° for 2 hr. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier. In addition, cDNA was synthesized from 4 μg of anti-IgM activated human B cell poly(A)$^+$ RNA in a reaction containing 50 mM Tris, pH 8.8, 50 μg/ml oligo(dT)$_{12-18}$, 327 units/ml RNasin, and 952 units/ml AMV reverse transcriptase in a total volume of 100 μl at 42° for 0.67 hr. Following reverse transcription, the reverse transcriptase was inactivated by heating at 70° for 10 min. The cDNA was converted to double-stranded DNA by adding 320 μl H$_2$O and 80 μl of a solution of 0.1M Tris, pH 7.5, 25 mM MgCl$_2$, 0.5M KCl, 250 μg/ml bovine serum albumin, and 50 mM dithiothreitol, and adjusting the solution to 200 μM each DATP, dCTP, dGTP, dTTP, 50 units/ml DNA polymerase I, 8 units/ml ribonuclease H and incubating at 16° C. for 2 hours. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier.

The DNA from 4 μg of AMV reverse transcription and 2 μg of Moloney MLV reverse transcription was combined. Non-selfcomplementary BstXI adaptors were added to the DNA as follows: The double-stranded cDNA from 6 μg of poly(A)$^+$ RNA was incubated with 3.6 μg of a kinased oligonucleotide of the sequence CTTTAGAGCACA (SEQ ID NO:15) and 2.4 μg of a kinased oligonucleotide of the sequence CTCTAAAG (SEQ ID NO:16) in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 0.45 ml at 15° C. for 16 hours. EDTA was added to 34 mM and the solution was extracted with an equal volume of 50% phenol, 49% chloroform, 1% isoamyl alcohol. DNA was precipitated with two volumes of ethanol in the presence of 2.5M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) was pooled and ethanol precipitated.

The pCDM8 vector was prepared for cDNA cloning by digestion with BstXI and purification on an agarose gel. Adaptored DNA from 6 μg of poly(A)$^+$RNA was ligated to 2.25 μg of BstXI cut pCDM8 in a solution containing 6 mM Tris, pH 7.5, 6 mM MgCl$_2$, 5 mM NaCl, 350 μg/ml bovine serum albumin, 7 mM mercaptoethanol, 0.1 mM ATP, 2 mM dithiothreitol, 1 mM spermidine, and 600 units T4 DNA ligase in a total volume of 1.5 ml at 15° for 24 hr. The ligation reaction mixture was transformed into competent $E.$ $coli$ MC1061/P3 and a total of 4,290,000 independent cDNA clones were obtained.

Plasmid DNA was prepared from a 500 ml culture of the original transformation of the cDNA library. Plasmid DNA was purified by the alkaline lysis procedure followed by twice banding in CsCl equilibrium gradients (Maniatis et al., $Molecular$ $Cloning:$ $A$ $Laboratory$ $Manual,$ Cold Spring Harbor, N.Y. (1987)).

B. Cloning Procedure

In the first round of screening, thirty 100 mm dishes of 50% confluent COS cells were transfected with 0.05 μg/ml anti-IgM activated human B cells library DNA using the DEAE-Dextran method (Seed et al., $Proc.$ $Natl.$ $Acad.$ $Sci.$ $USA,$ 84:3365 (1987)). The cells were trypsinized and re-plated after 24 hours. After 47 hours, the cells were detached by incubation in PBS/0.5 mM EDTA, pH 7.4/ 0.02% Na azide at 37° C. for 30 min. The detached cells were treated with 10 μg/ml/CTLA4Ig and CD28Ig for 45 minutes at 4° C.. Cells were washed and distributed into panning dishes coated with affinity-purified Goat anti-human IgG antibody and allowed to attach at room temperature. After 3 hours, the plates were gently washed twice with PBS/0.5 mM EDTA, pH 7.4/0.02% Na azide, 5% FCS and once with 0.15M NaCl, 0.01 M Hepes, pH 7.4, 5% FCS. Episomal DNA was recovered from the panned cells and transformed into $E.$ $coli$ DH10B/P3. The plasmid DNA was re-introduced into COS cells via spheroplast fusion as described (Seed et al., $Proc.$ $Natl.$ $Acad.$ $Sci.$ $USA,$ 84:3365 (1987)) and the cycle of expression and panning was repeated twice. In the second and third rounds of selection, after 47 hours, the detached COS cells were first incubated with α-B7-1 mAbs (133 and B1.1, 10 μg/ml), and COS cells expressing B7-1 were removed by α-mouse IgG and IgM coated magnetic beads. COS cells were then treated with 10 μg/ml of human CTLA4Ig (hCTLA4Ig) and human CD28Ig (hCD28Ig) and human B7-2 expressing COS cells were selected by panning on dishes with goat anti-human IgG antibody plates. After the third round, plasmid DNA was prepared from individual colonies and transfected into COS cells by the DEAE-Dextran method. Expression of B7-2 on transfected COS cells was analyzed by indirect immunofluorescence with CTLA4Ig.

After the final round of selection, plasmid DNA was prepared from individual colonies. A total of 4 of 48 candidate clones contained a cDNA insert of approximately 1.2 kb. Plasmid DNA from these four clones was transfected into COS cells. All four clones were strongly positive for B7-2 expression by indirect immunofluorescence using CTLA4Ig and flow cytometric analysis.

C. Sequencing

The B7-2 cDNA insert in clone29 was sequenced in the pCDM8 expression vector employing the following strategy. Initial sequencing was performed using sequencing primers T7, CDM8R (Invitrogen) homologous to pCDM8 vector sequences adjacent to the cloned B7-2 cDNA (see Table I). Sequencing was performed using dye terminator chemistry and an ABI automated DNA sequencer. (ABI, Foster City, Calif.). DNA sequence obtained using these primers was used to design additional sequencing primers (see Table I). This cycle of sequencing and selection of additional primers was continued until the B7-2 cDNA was completely sequenced on both strands.

TABLE I

| | |
|---|---|
| T7(F) (SEQ ID NO:3) | 5'd[TAATACGACTCACTATAGGG]3' |
| CDM8(R) (SEQ ID NO:4) | 5'd[TAAGGTTCCTTCACAAAG]3' |
| CDM8 RGV(2) (SEQ ID NO:5) | 5'd[ACTGGTAGGTATGGAAGATCC]3' |
| HBX29-5P (2R) (SEQ ID NO:6) | 5'd[ATGCGAATCATTCCTGTGGGC]3' |
| HBX29-5P (2F) (SEQ ID NO:7) | 5'd[AAAGCCCACAGGAATGATTCG]3' |
| HBX29-5P (SEQ ID NO:8) | 5'd[CTCTCAAAACCAAABCCTGAG]3' |
| 5PA (SEQ ID NO:9) | 5'd[TTAGGTCACAGCAGAAGCAGC]3' |
| 5PA (3FA) (SEQ ID NO:10) | 5'd[TCTGGAAACTGACAAGACGCG]3' |
| HBX29-5P(1R) (SEQ ID NO:11) | 5'd[CTCAGGCTTTGGTTTTGAGAG]3' |
| HBX29-3P(1R) (SEQ ID NO:12) | 5'd[CACTCTCTTCCCTCTCCATTG]3' |
| HBX29-5P(3R) (SEQ ID NO:13) | 5'd[GACAAGCTGATGGAAACGTCG]3' |
| HBX29-3P(1P) (SEQ ID NO:14) | 5'd[CAATGGAGAGGGAAGAGAGTG]3' |

The human B7-2 clone 29 contained an insert of 1,120 base pairs with a single long open reading frame of 987 nucleotides and approximately 27 nucleotides of 3' noncoding sequences (FIG. 8 (SEQ ID NO:1)). The predicted amino acid sequence encoded by the open reading frame of the protein is shown below the nucleotide sequence in FIG. 8. The encoded protein, human B7-2, is predicted to be 329 amino acids in length (SEQ ID NO:2). This protein sequence exhibits many features common to other type 1 Ig superfamily membrane proteins. Protein translation is predicted to begin at the ATG codon (nucleotide 107–109) based on DNA homology in this region with the consensus eukaryotic translation initiation site (Kozak, M. (1987) *Nucl. Acids Res.* 15:8125–8148). The amino terminus of the human B7-2 protein (amino acids 1 to 23) has the characteristics of a secretory signal peptide with a predicted cleavage between the alanines at positions 23 and 24 (von Heijne (1986) *Nucl. Acids Res.* 14:4683). Processing at this site would result in a human B7-2 membrane bound protein of 306 amino acid with an unmodified molecular weight of approximately 34 kDa. This protein would consist of an extracellular Ig superfamily V and C like domains, of from about amino acid residue 24–245, a hydrophobic transmembrane domain of from about amino acid residue 246–268 and a long cytoplasmic domain of from about amino acid residue 269–329. The homologies to the Ig superfamily are due to the two contiguous Ig-like domains in the extracellular region bound by the cysteines at positions 40 to 110 and 157 to 218. The extracellular domain also contains eight potential N-linked glycosylation sites. *E. coli* transfected with a vector containing the cDNA insert of clone 29, encoding the human B7-2 protein, was deposited with the American Type Culture Collection (ATCC) on Jul. 26, 1993 as Accession No. 69357.

Comparison of both the nucleotide and amino acid sequences of human B7-2 with the GenBank and EMBL databases showed that only the human and murine B7-1 proteins are related. Alignment of the three B7 protein sequences (see FIG. 13) shows that human B7-2 has approximately 26% amino acid identity with human B7-1. FIG. 13 represents the comparison of the amino acid sequences for human B7-2 (hB7-2) (SEQ ID NO:2), human B7-1 (hB7-1) (SEQ ID NO:28 and 29) and murine B7 (mB7) (SEQ ID NO:30 and 31). The amino acid sequences for the human B7-1 and murine B7 (referred to herein as murine B7-1) can be found in Genbank at Accession #M27533 and X60958 respectively. Vertical lines in FIG. 13 show identical amino acids between the hB7-2 and hB7-1 or hB7. Identical amino acids between hB7-1 and mB7 are not shown. The hB7-2 protein exhibits the same general structure as hB7-1 as defined by the common cysteines (positions 40 and 110, IgV domains; positions 157 and 217, IgC domain) which the Ig superfamily domains and by many other common amino acids. Since both hB7-1 and mB7 have been shown to bind to both human CTLA4 and human CD28, the amino acids in common between these two related proteins will be those necessary to comprise a CTLA4 or CD28 binding sequence. An example of such a sequence would be the KYMGRTSFD (position 81–89, hB7-2) (SEQ ID NO:17) or KSQDNVTELYDVS (position 188–200, hB7-2) (SEQ ID NO:18). Additional related sequences are evident from the sequence comparison and others can be inferred by considering homologous related amino acids such as aspartic acid and glutamic acid, alanine and glycine and other recognized functionally related amino acids. The B7 sequences share a highly positive charged domain with the cytoplasmic portion WKWKKKKRPRN-SYKC (position 269–282, hB7-2) (SEQ ID NO:19) which is probably involved in intracellular signaling.

EXAMPLE 5

Characterization of the Recombinant B7-2 Antigen

A. B7-2 Binds CTLA4Ig and Not Anti-B7-1 and Anti-B7-3 Monoclonal Antibodies

Figure 9:
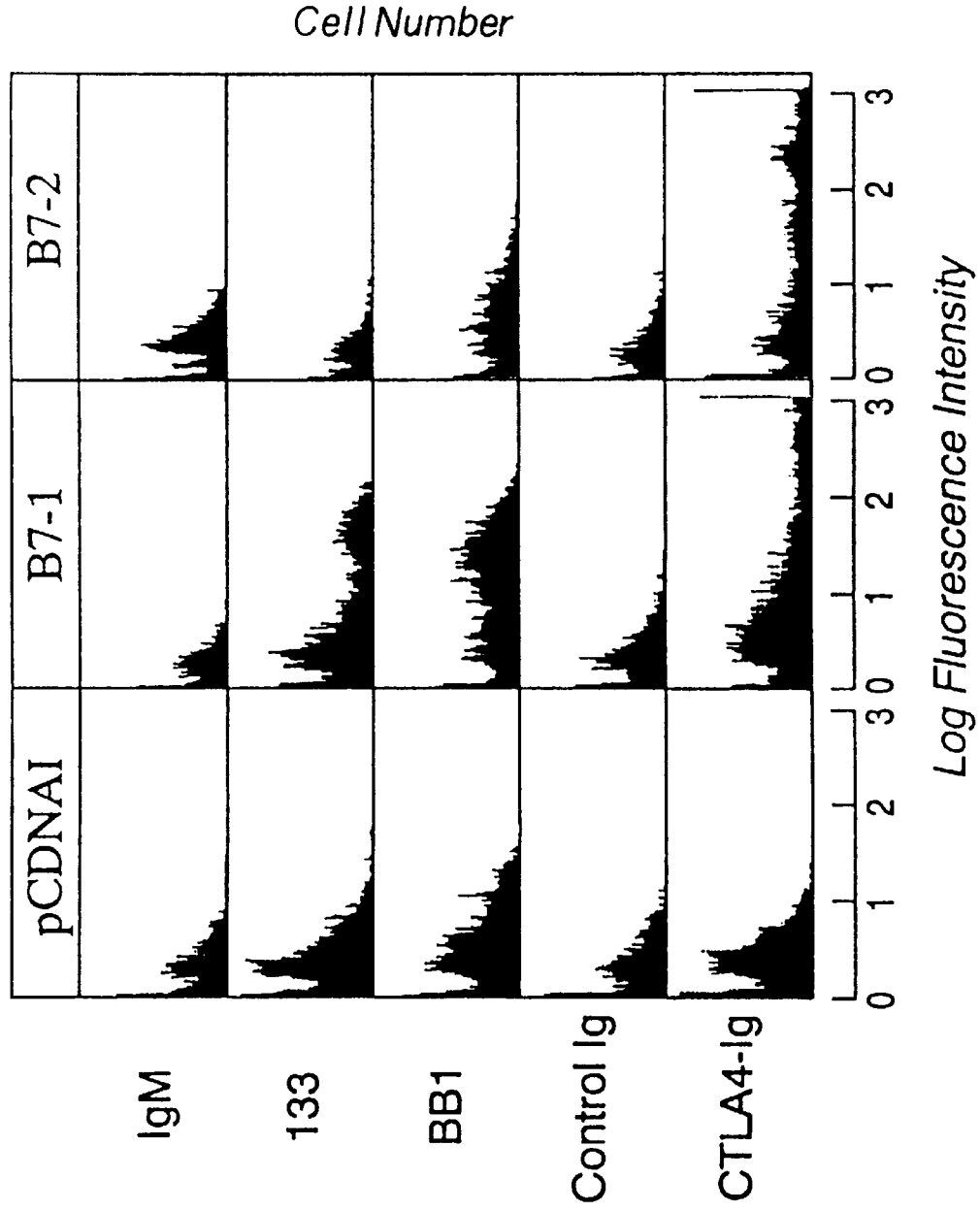
FIG. 9 is a graphic representation of COS cells transfected with control plasmid (pCDNAI), plasmid expressing B7-1 (B7-1), or plasmid expressing B7-2 (B7-2) stained with either control mAb (IgM), anti-B7-1 (mAbs 133 and BB-1), recombinant protein CTLA4Ig, or isotype matched control Ig protein followed by the appropriate second FITC labelled immunoglobulin and analyzed by flow cytometry.

COS cells transfected with either vector DNA (pCDNAI), or an expression plasmid containing B7-1 (B7-1) or B7-2 (B7-2) were prepared. After 72 hours, the transfected COS cells were detached by incubation in PBS containing 0.5 mM EDTA and 0.02% Na azide for 30 min. at 37° C.. Cells were analyzed for cell surface expression by indirect immunofluorescence and flow cytometric analysis using fluoroscein isothiocyanate conjugated (FITC) goat-anti-mouse Ig or goat-anti-human IgG FITC (FIG. 9). Cell surface expression of B7-1 was detected with mAbs 133 (anti-B7-1) and BB-1 (anti-B7-1 and anti-B7-3) and with CTLA4Ig, whereas B7-2 reacted only with CTLA4Ig. Neither of the B7 transfectants showed any staining with the isotype controls (IgM or control Ig). The vector transfected COS cells showed no staining with any of the detection reagents. In addition, one of the cells showed any staining with the FITC labeled detection reagents and alone. This demonstrates that B7-2 encodes a protein that is a CTLA4 counter-receptor but is distinct from B7-1 and B7-3.

B. RNA Blot Analysis of B7-2 Expression in Unstimulated and Activated Human B Cells, Cell Lines, and Myelomas Human splenic B cells were isolated by removing T cells and monocytes as previously described (Freedman, A. S., Freeman, G. J., Horowitz, J. C., Daley, J., Nadler, L. M., *J. Immunol.* (1987) 137:3260–3267). Splenic B cells were activated using anti-Ig beads and cells were harvested at the indicated times (Freedman et al., (1987), cited supra).

Figure 10A:
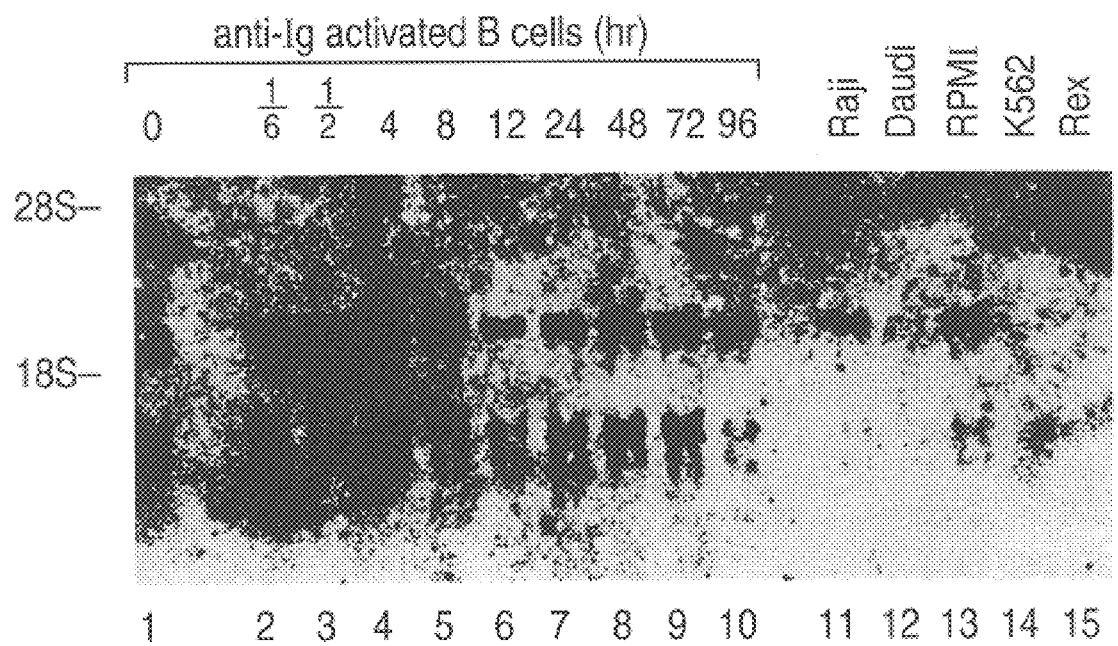
FIGS. 10A–B show RNA blot analyses of B7-2 expression in unstimulated and anti-Ig activated human spenic B cells and cell lines (panel a) and human myelomas (panel b).
Figure 10B:
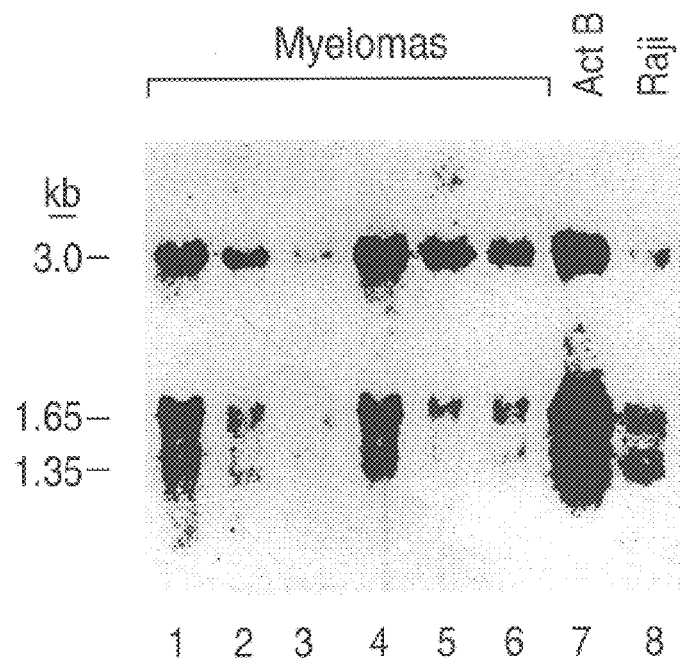

Human myelomas from bone marrow specimens were enriched by removing T cells and monocytes using E rosettes and adherence as previously described (Freeman, G. J., et al., *J. Immunol.* (1989) 143:2714–2722). RNA was prepared by guanidine thiocyanate homogenization and cesium chloride centrifugation. Equal amounts of RNA (20 µg) were electrophoresed on an agarose gel, blotted, and hybridized to $^{32}$P-labelled B7-2 cDNA. FIG. 10, panel a, shows RNA blot analysis of unstimulated and anti-Ig activated human splenic B cells and of cell lines including Raji (B cell Burkitts lymphoma), Daudi (B cell Burkitt's lymphoma), RPMI 8226 (myeloma), K562 (erythroleukemia), and REX (T cell acute lymphoblastic leukemia). FIG. 10, panel b shows RNA blot analysis of human myeloma specimens.

Three mRNA transcripts of 1.35, 1.65 and 3.0 kb were identified by hybridization to the B7-2 cDNA (FIG. 10, panel b). RNA blot analysis demonstrated that B7-2 mRNA is expressed in unstimulated human splenic B cells and increases 4-fold following activation (FIG. 10, panel a). B7-2 mRNA was expressed in B cell neoplastic lines (Raji, Daudi) and a myeloma (RPMI 8226) but not in the erythroleukemia K562 and the T cell line REX. In contrast, we have previously shown that B7-1 mRNA is not expressed in resting B cells and is transiently expressed following activation (G. J. Freeman et al. (1989) supra). Examination of mRNA isolated from human myelomas demonstrates that B7-2 mRNA is expressed in 6 of 6 patients, whereas B7-1 was found in only 1 of these 6 (G. J. Freeman et al. (1989) supra). Thus, B7-1 and B7-2 expression appears to be independently regulated.

C. Costimulation

Human CD28$^+$ T cells were isolated by immunomagnetic bead depletion using monoclonal antibodies directed against B cells, natural killer cells and macrophages as previously described (Gimmi, C. D., et al. (1993) *Proc. Natl. Acad. Sci. USA* 90, 6586–6590).

B7-1, B7-2 and vector transfected COS cells were harvested 72 hours after transfection, incubated with 25 µg/ml of mitomycin-C for 1 hour, and then extensively washed. $10^5$ CD28$^+$ and T cells were incubated with 1 ng/ml of phorbol myristic acid (PMA) and the indicated number of COS transfectants (FIG. 11). As shown in FIG. 11, panel a, T cell proliferation was measured by 3H-thymidine (1 µCi) incorporated for the last 12 hours of a 72 hour incubation. Panel b of FIG. 11 shows IL-2 production by T cells as measured by ELISA (Biosource, CA) using supernatants harvested 24 hours after the initiation of culture.

B7-1 and B7-2 transfected COS cells costimulated equivalent levels of T cell proliferation when tested at various stimulator to responder ratios (FIG. 11). Like B7-1, B7-2 transfected COS cell costimulation resulted in the production of IL-2 over a wide range of stimulator to responder cell ratios (FIG. 11). In contrast, vector transfected COS cells did not costimulate T cell proliferation or IL-2 production.

D. B7-2 Costimulation is not Blocked by Anti-B7-1 and Anti-B7-3 mAbs but is Blocked by CTLA4-Ig and Anti-CD28 Fab Human CD28$^+$ T cells were isolated by immunomagnetic bead depletion using mAbs directed against B cells, natural killer cells, and macrophages as previously described (Gimmi, C. D., Freeman, G. J., Gribben, J. G., Gray, G., Nadler, L. M. (1993) *Proc. Natl. Acad. Sci USA* 90, 6586–6590). B7-1, B7-2, and vector transfected COS cells were harvested 72 hours after transfection, incubated with 25 µg/ml of mitomycin-C for 1 hour, and then extensively washed. $10^5$ CD28$^+$ T cells were incubated with 1 ng/ml of phorbol myristic acetate (PMA) and $2\times10^4$ COS transfectants. Blocking agents (10 µg/ml) are indicated on the left side of FIG. 12 and include: 1) no monoclonal antibody (no blocking agents), 2) mAb 133 (anti-B7-1 mAb), 3) mAb BB1 (anti-B7-1 and anti-B7-3 mAb), 4) mAb B5 (control IgM mAb), 5) anti-CD28 Fab (mAb 9.3), 6) CTLA-Ig, and 7) control Ig. Panel a of FIG. 12 shows proliferation measured by $^3$H-thymidine (1 µCi) incorporation for the last 12 hours of a 72 hour incubation. FIG. 12, panel b, shows IL-2 production as measured by ELISA (Biosource, CA) using supernatants harvested 24 hours after the initiation of culture.

To distinguish B7-2 from B7-1 and B7-3, mAbs directed against B7-1 and B7-3 were used to inhibit proliferation and IL-2 production of submitogenically activated human CD28+T cells. Both B7-1 and B7-2 COS transfectants costimulated T cell proliferation and IL-2 production (FIG. 12). MAbs 133 (Freedman, A. S. et al. (1987) supra) (anti-B7-1) and BB1 (Boussiotis, V. A., et al., (in review) *Proc. Natl. Acad. Sci. USA;* Yokochi, T., Holly, R. D., Clark, E. A. (1982) *J. Immunol.* 128, 823–827) (anti-B7-1 and anti-B7-3) completely inhibited proliferation and IL-2 secretion induced by B7- 1 but had no effect upon costimulation by B7-2 transfected COS cells. Isotype matched control B5 mAb had no effect. To determine whether B7-2 signals via the CD28/CTLA4 pathway, anti-CD28 Fab and CTLA4-Ig fusion protein were tested to determine whether they inhibited B7-2 costimulation. Both anti-CD28 Fab and CTLA4-Ig inhibited proliferation and IL-2 production induced by either B7-1 or B7-2 COS transfectants whereas control Ig fusion protein had no effect (FIG. 12). While CTLA4-Ig inhibited B7-2 costimulation of proliferation by only 90%, in other experiments inhibition was more pronounced (98–100%). None of the blocking agents inhibited T cell proliferation or IL-2 production induced by the combination of PMA and phytohemagglutinin.

Like B7-1, B7-2 is a counter-receptor for the CD28 and CTLA4 T cell surface molecules. Both proteins are similar in that they are: 1) expressed on the surface of APCs; 2) structurally related to the Ig supergene family with an IgV and IgC domain which share 26% amino acid identity, and 3) capable of costimulating T cells to produce IL-2 and proliferate. However, B7-1 and B7-2 differ in several fundamental ways. First, B7-2 mRNA is constitutively expressed in unstimulated B cells, whereas B7-1 mRNA does not appear until 4 hours and cell surface protein is not detected until 24 hours (Freedman, A. S., et al. (1987) supra; Freeman, G. J., et al. (1989) supra). Unstimulated human B cells do not express CTLA4 counter-receptors on the cell surface and do not costimulate T cell proliferation (Boussiotis, V. A., et al. supra). Therefore, expression of B7-2 mRNA in unstimulated B cells would allow rapid expression of B7-2 protein on the cell surface following activation, presumably from stored mRNA or protein. Costimulation by B7-2 transfectants is partially sensitive to paraformaldehyde fixation, whereas B7-2 costimulation is resistant (Gimmi, C. D., et al. (1991) *Proc. Natl. Acad. Sci. USA* 88, 6575–6579). Second, expression of B7-1 and B7-2 in cell lines and human B cell neoplasms substantially differs. Third, B7-2 protein contains a longer cytoplasmic domain than B7-1 and this could play a role in signaling B-cell differentiation. These phenotypic and functional differences suggest that these homologous molecules may have biologically distinct functions.

EXAMPLE 6
Cloning and Sequencing of the Murine B7-2 Antigen

A. Construction of cDNA Library

A cDNA library was constructed in the pCDM8 vector (Seed, *Nature,* 329:840 (1987)) using poly (A)⁺ RNA from dibutryl cyclic AMP (cAMP) activated M12 cells (a murine B cell tumor line) as described (Aruffo et al., *Proc. Natl. Acad. Sci. USA,* 84:3365 (1987)).

M12 cells were cultured at 1×10⁶ cells/ml in complete culture media, {RPMI 1640 with 10% heat inactivated fetal calf serum (FCS), 2 mM glutamine, I mM sodium pyruvate, penicillin (100 units/ml), streptomycin sulfate (100 µg/ml) and gentamycin sulfate (5 µg/ml)}, in tissue culture flasks and were activated by 300 µg/ml dibutryl cAMP (Nabavi, N., et al. (1992) *Nature* 360, 266–268). Activated M12 cells were harvested after 0, 6, 12, 18, 24 and 30 hours.

RNA was prepared by homogenizing activated M12 cells in a solution of 4M guanidine thiocyanate, 0.5% sarkosyl, 25 mM EDTA, pH 7.5, 0.13% Sigma anti-foam A, and 0.7% mercaptoethanol. RNA was purified from the homogenate by centrifugation for 24 hour at 32,000 rpm through a solution of 5.7M CsCl, 10 mM EDTA, 25 mM Na acetate, pH 7. The pellet of RNA was dissolved in 5% sarkosyl, 1 mM EDTA, 10 mM Tris, pH 7.5 and extracted with two volumes of 50% phenol, 49% chloroform, 1% isoamyl alcohol. RNA was ethanol precipitated twice. Poly (A)⁺ RNA used in cDNA library construction was purified by two cycles of oligo (dT)-cellulose selection Complementary DNA was synthesized from 5.5 µg of dibutryl cAMP activated murine M12 cell poly(A)⁺ RNA in a reaction containing 50 mM Tris, pH 8.3, 75 mM KCl, 3 mM MgCl₂, 10 mM dithiothreitol, 500 µM dATP, dCTP, dGTP, dTTP, 50 µg/ml oligo(dT)₁₂₋₁₈, 180 units/ml RNasin, and 10,000 units/ml Moloney-MLV reverse transcriptase in a total volume of 55 µl at 37° C. for 1 hr. Following reverse transcription, the cDNA was converted to double-stranded DNA by adjusting the solution to 25 mM Tris, pH 8.3, 100 mM KCl, 5 mM MgCl₂, 250 µM each DATP, dCTP, dGTP, dTTP, 5 mM dithiothreitol, 250 units/ml DNA polymerase I, 8.5 units/ml ribonuclease H and incubating at 16° C. for 2 hr. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier. Following reverse transcription, the reverse transcriptase was inactivated by heating at 70° C. for 10 min. The cDNA was converted to double-stranded DNA by adding 320 µl H₂O and 80 µl of a solution of 0.1M Tris, pH 7.5, 25 mM MgCl₂, 0.5M KCl, 250 µg/ml bovine serum albumin, and 50 mM dithiothreitol, and adjusting the solution to 200 µM each dATP, dCTP, dGTP, dTTP, 50 units/ml DNA polymerase I, 8 units/ml ribonuclease H and incubating at 16° C. for 2 hours. EDTA was added to 18 mM and the solution was extracted with an equal volume of 50% phenol, 49% chloroform, 1% isoamyl alcohol. DNA was precipitated with two volumes of ethanol in the presence of 2.5M ammonium acetate and with 4 micrograms of linear polyacrylamide as carrier.

2 µg of non-selfcomplementary BstXI adaptors were added to the DNA as follows: The double-stranded cDNA from 5.5 µg of poly(A)⁺ RNA was incubated with 3.6 µg of a kinased oligonucleotide of the sequence CTTTAGAG-CACA (SEQ ID NO:15) and 2.4 µg of a kinased oligonucleotide of the sequence CTCTAAAG (SEQ ID NO:16) in a solution containing 6 mM Tris, pH 7.5, 6 mM MgCl₂, 5 mM NaCl, 350 µg/ml bovine serum albumin, 7 mM mercaptoethanol, 0.1 mM ATP, 2 mM dithiothreitol, 1 mM spermidine, and 600 units T4 DNA ligase in a total volume of 0.45 ml at 15° for 16 hours. EDTA was added to 34 mM and the solution was extracted with an equal volume of 50% phenol, 49% chloroform, 1% isoamyl alcohol. DNA was precipitated with two volumes of ethanol in the presence of 2.5M ammonium acetate.

DNA larger than 600 bp was selected as follows: The adaptored DNA was redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) was pooled and ethanol precipitated.

The pCDM8 vector was prepared for cDNA cloning by digestion with BstXI and purification on an agarose gel. Adaptored DNA from 5.5 µg of poly(A)⁺RNA was ligated to 2.25 µg of BstXI cut pCDM8 in a solution containing 6 mM Tris, pH 7.5, 6 mM MgCl₂, 5 mM NaCl, 350 µg/ml bovine serum albumin, 7 mM mercaptoethanol, 0.1 mM ATP, 2 mM dithiothreitol, 1 mM spermidine, and 600 units T4 DNA ligase in a total volume of 1 .5 ml at 15° for 24 hr. The ligation reaction mixture was transformed into competent *E. coli* MC1061/P3 and a total of 200×10⁶ independent cDNA clones were obtained.

Plasmid DNA was prepared from a 500 ml culture of the original transformation of the cDNA library. Plasmid DNA was purified by the alkaline lysis procedure followed by twice banding in CsCl equilibrium gradients (Maniatis et al., *Molecular Cloning: A Laboratory Manual,* Cold Spring Harbor, N.Y. (1987)).

B. Cloning Procedure

In the first round of screening, thirty 100 mm dishes of 50% confluent COS cells were transfected with 0.05 µg/ml activated M12 murine B cell library DNA using the DEAE-Dextran method (Seed et al., *Proc. Natl. Acad. Sci. USA,* 84:3365 (1987)). The cells were trypsinized and re-plated after 24 hours. After 47 hours, the cells were detached by incubation in PBS/0.5 mM EDTA, pH 7.4/0.02% Na azide at 37° C. for 30 min. The detached cells were treated with 10 µg/ml/human CTLA4Ig and murine CD28Ig for 45 minutes at 4° C.. Cells were washed and distributed into panning dishes coated with affinity-purified Goat anti-human IgG antibody and allowed to attach at room temperature. After 3 hours, the plates were gently washed twice with PBS/0.5 mM EDTA, pH 7.4/0.02% Na azide, 5% FCS and once with 0. 15M NaCl, 0.01 M Hepes, pH 7.4, 5% FCS. Episomal DNA was recovered from the panned cells and transformed into *E. coli* DH10B/P3. The plasmid DNA was re-introduced into COS cells via spheroplast fusion as described (Seed et al., *Proc. Natl. Acad. Sci. USA,* 84:3365 (1987)) and the cycle of expression and panning was repeated twice. In the second and third rounds of selection, after 47 hours, the detached COS cells were first incubated with α-murine B7-1 mAb (16-10A1, 10 µg/ml), and COS cells expressing B7-1 were removed by α-mouse IgG and IgM coated magnetic beads. COS cells were then treated with 10 µg/ml of human CTLA4Ig and murine CD28Ig and murine B7-2 expressing COS cells were selected by panning on dishes coated with goat anti-human IgG antibody. After the third round, plasmid DNA was prepared from individual colonies and transfected into COS cells by the DEAE-Dextran method. Expression of B7-2 on transfected COS cells was analyzed by indirect immunofluorescence with CTLA4Ig.

After the final round of selection, plasmid DNA was prepared from individual colonies. A total of 6 of 8 candidate clones contained a cDNA insert of approximately 1.2 kb.

Plasmid DNA from these eight clones was transfected into COS cells. All six clones with the 1.2 Kb cDNA insert were strongly positive for B7-2 expression by indirect immunofluorescence using CTLA4Ig and flow cytometric analysis.

C. Sequencing

The B7-2 cDNA insert in clone4 was sequenced in the pCDM8 expression vector employing the following strategy. Initial sequencing was performed using sequencing primers T7, CDM8R (Invitrogen) homologous to pCDM8 vector sequences adjacent to the cloned B7-2 cDNA (see Table II). Sequencing was performed using dye terminator chemistry and an ABI automated DNA sequencer. (ABI, Foster City, Calif.). DNA sequence obtained using these primers was used to design additional sequencing primers (see Table II). This cycle of sequencing and selection of additional primers was continued until the murine B7-2 cDNA was completely sequenced on both strands.

TABLE II

| | |
|---|---|
| T7(F) (SEQ ID NO:3) | 5'd[TAATACGACTCACTATAGGG]3' |
| CDM8(R) (SEQ ID NO:4) | 5'd[TAAGGTTCCTTCACAAAG]3' |
| MBX4-1F (SEQ ID NO:24) | 5'd[ACATAAGCCTGAGTGAGCTGG]3' |
| MBX4-2R (SEQ ID NO:25) | 5'd[ATGATGAGCAGCATCACAAGG]3' |
| MBX4-14 (SEQ ID NO:26) | 5'd[TGGTCGAGTGAGTCCGAATAC]3' |
| MBX4-2F (SEQ ID NO:27) | 5'd[GACGAGTAGTAACATACAGTG]3' |

A murine B7-2 clone (mB7-2, clone 4) was obtained containing an insert of 1,163 base pairs with a single long open reading frame of 927 nucleotides and approximately 126 nucleotides of 3' noncoding sequences (FIG. 14, SEQ ID NO:22). The predicted amino acid sequence encoded by the open reading frame of the protein is shown below the nucleotide sequence in FIG. 14. The encoded murine B7-2 protein, is predicted to be 309 amino acid residues in length (SEQ ID NO:23). This protein sequence exhibits many features common to other type I Ig superfamily membrane proteins. Protein translation is predicted to begin at the methionine codon (ATG, nucleotides 111 to 113) based on the DNA homology in this region with the consensus eucaryotic translation initiation site (see Kozak, M. (1987) *Nucl. Acids Res.* 15:8125–8148). The amino terminus of the murine B7-2 protein (amino acids 1 to 23) has the characteristics of a secretory signal peptide with a predicted cleavage between the alanine at position 23 and the valine at position 24 (von Heijne (1987) *Nucl. Acids Res.* 14:4683). Processing at this site would result in a murine B7-2 membrane bound protein of 286 amino acids having an unmodified molecular weight of approximately 32 kDa. This protein would consist of an approximate extracellular Ig superfamily V and C like domains of from about amino acid residue 24 to 246, a hydrophobic transmembrane domain of from about amino acid residue 247 to 265, and a long cytoplasmic domain of from about amino acid residue 266 to 309. The homologies to the Ig superfamily are due to the two contiguous Ig-like domains in the extracellular region bound by the cysteines at positions 40 to 110 and 157 to 216. The extracellular domain also contains nine potential N-linked glycosylation sites and, like murine B7-1, is probably glycosylated. Glycosylation of the murine B7-2 protein may increase the molecular weight to about 50–70 kDa. The cytoplasmic domain of murine B7-2 contains a common region which has a cysteine followed by positively charged amino acids which presumably functions as signaling or regulatory domain within an APC. Comparison of both the nucleotide and amino acid sequences of murine B7-2 with the GenBank and EMBL databases yielded significant homology (about 26% amino acid sequence identity) with human and murine B7-1. Murine B7-2 exhibits about 50% identity and 67% similarity with its human homologue, hB7-2. *E. coli* (DH106/p3) transfected with a vector (plasmid pmBx4) containing a cDNA insert encoding murine B7-2 (clone 4) was deposited with the American Type Culture Collection (ATCC) on Aug. 18, 1993 as Accession No. 69388.

D. Costimulation $CD4^+$ murine T cells were purified by first depleting red blood cells by treatment with Tris-$NH_4Cl$. T cells were enriched by passage over a nylon wool column. $CD4^+$ T cells were purified by two-fold treatment with a mixture of anti-MHC class II and anti-CD28 mAbs and rabbit complement. Murine B7-1 (obtained from Dr. Gordon Freeman, Dana-Farber Cancer Institute, Boston, Mass.; see also, Freeman, G. J. et al (1991) *J. Exp. Med.* 174, 625–631) murine B7-2, and vector transfected COS cells were harvested 72 hours after transfection, incubated with 25 μg/ml mitomycin-C for one hour, and then extensively washed. $10^5$ murine $CD4^+$ T cells were incubated with 1 ng/ml of phorbol myristic acid (PMA) and $2 \times 10^4$ COS transfectants (Table III). T cell proliferation was measured by 3H-thymidine (1 μCi) incorporated for the last 12 hours of a 72 hour incubation.

TABLE III

| | 3H-Thymidine Incorporation (cpm) |
|---|---|
| $CD4^+$ T cells | 175 |
| $CD4^+$ T cells + 1 ng/ml PMA | 49 |
| $CD4^+$ T cells + COS-vector | 1750 |
| $CD4^+$ T cells + COS-B7-1 | 4400 |
| $CD4^+$ T cells + COS-B7-2 | 2236 |
| $CD4^+$ T cells + 1 ng/ml PMA + COS-vector | 2354 |
| $CD4^+$ T cells + 1 ng/ml PMA + COS-B7-1 | 67935 |
| $CD4^+$ T cells + 1 ng/ml PMA + COS-B7-2 | 43847 |

EXAMPLE 7

Construction and Characterization of Human B7-2 Immunoglobulin Fusion Proteins

A. Preparation of Human B7-2Ig Fusion Proteins

The extracellular portion of human B7-2 was prepared as a fusion protein coupled to an immunoglobulin constant region. The immunoglobulin constant region may contain genetic modifications including those which reduce or eliminate effector activity inherent in the immunoglobulin structure. Briefly, DNA encoding the extracellular portion of hB7-2 was joined to DNA encoding the hinge, CH2 and CH3 regions of human IgCγ1 or IgCγ4 modified by directed mutagenesis. This was accomplished as described in the following subsections.

B. Preparation of Gene Fusions

DNA fragments corresponding to the DNA sequences of interest were prepared by polymerase chain reaction (PCR) using primer pairs described below. In general, PCR reactions were prepared in 100 μl final volume composed of Taq, polymerase buffer (Gene Amp PCR Kit, Perkin-Elmer/Cetus, Norwalk, Conn.) containing primers (1 μM each), dNTPs (200 μM each) 1 ng of template DNA, and Taq, polymerase (Saiki, R. K., et al. (1988) *Science* 239:487–491). PCR DNA amplifications were run on a thermocycler (Ericomp, San Diego, Calif.) for 25 to 30 cycles each composed of a denaturation step (1 minute at 94° C.), a renaturation step (30 seconds at 54° C.), and a chain elongation step (1 minute at 72° C.). The structure of each hB7-2 Ig genetic fusion consisted of a signal sequence to facilitate secretion coupled to the extracellular domain of B7-2 and the hinge, CH2 and CH3 domains of human IgCγ1 or IgCγ4. The IgC gamma 1 and IgC gamma 4 sequences contained nucleotide changes within the hinge region to replace cysteine residues available for disulfide bond formation with serine residues and may contain nucleotide changes to replace amino acids within the CH2 domain thought to be required for IgC binding to Fc receptors and complement activation.

Sequence analysis confirmed structures of both $m\gamma_4$ and $\gamma_1$ clones, and each construct was used to transfect 293 cells to test transient expression. hIgG ELISA measured/confirmed transient expression levels approximately equal to 100 ng protein/ml cell supernatant for both constructs. NSO cell lines were transfected for permanent expression the the fusion proteins.

C. Genetic Construction of hB7-2Ig Fusion Proteins (1). Preparation of Signal Sequence PCR amplification was used to generate an immunoglobulin signal sequence suitable for secretion of the B7-2Ig fusion protein from mammalian cells. The Ig signal sequence was prepared from a plasmid containing the murine IgG heavy chain gene (Orlandi, R. et al. (1989) *Proc. Natl. Acad. Sci. USA*. 86:38333837) using the oligonucleotide 5'-GGCACTAGGTCTCCAGCTTGAGATCAC-AGTTCTCTCTAC-3' (#01) (SEQ ID NO:32) as the forward primer and the oligonucleotide 5'-GCTTGAATCTTCAGAGGAGCGGAGTGGACACC-TGTGG-3' (#02) (SEQ ID NO:33) as the reverse PCR primer. The forward PCR primer (SEQ ID NO:32) contains recognition sequences for restriction enzymes BsaI and is homologous to sequences 5' to the initiating methionine of the Ig signal sequence. The reverse PCR primer (SEQ ID NO:33) is composed of sequences derived from the 5' end of the extracellular domain of hB7-2 and the 3' end of the Ig signal sequence. PCR amplification of the murine Ig signal template DNA using these primers resulted in a 224 bp product which is composed of BsaI restriction sites followed by the sequence of the Ig signal region fused to the first 20 nucleotides of the coding sequence of the extracellular domain of hB7-2. The junction between the signal sequence and hB7-2 is such that protein translation beginning at the signal sequence will continue into and through hB7-2 in the correct reading frame.

(2). Preparation of the hB7-2 Gene Segment

The extracellular domain of the hB7.2 gene was prepared by PCR amplification of plasmid containing the hB7-2 cDNA inserted into expression vector pCDNAI (Freeman et al., *Science* 262:909–11 (1994)):

The extracellular domain of hB7-2 was prepared by PCR amplification using oligonucleotide 5'-GCTCCTCTGAAGATTCAAGC-3' (#03) (SEQ ID NO:34) as the forward primer and oligonucleotide 5'-GGCACTATGATCAGGGGGAGGCTGAGGTCC-3' (#04) (SEQ ID NO:35) as the reverse primer. The forward PCR primer contained sequences corresponding to the first 20 nucleotides of the B7-2 extracellular domain and the reverse primer contained sequences corresponding to the last 22 nucleotides of the B7-2 extracellular domain followed by a Bcl I restriction site and 7 noncoding nucleotides. PCR amplification with primer #03 (SEQ ID NO:34) and #04 (SEQ ID NO:35) yields a 673 bp product corresponding to the extracellular IgV and IgC like domains of hB7-2 followed by a unique Bcl I restriction site.

The signal sequence was attached to the extracellular portion of hB7-2 by PCR as follows. DNA-PCR products obtained above corresponding to the signal sequence and the hB7-2 extracellular domain were mixed in equimolar amounts, denatured by heating to 100° C., held at 54° C. for 30° C. to allow the complementary ends to anneal and the strands were filled in using dNTPs and Taq polymerase. PCR primers #01 (SEQ ID NO:32) and #04 (SEQ ID NO:35) were added and the entire fragment produced by PCR amplification to yield a ~880 fragment composed of a BsaI restriction site followed by the signal sequence fused to the extracellular domain of hB7-2, followed by a Bcl I restriction site.

(3). Cloning and Modification of Immunoglobulin Fusion Domain

Plasmid pSP721 gG1 was prepared by cloning the 2000 bp segment of human IgGI heavy chain genomic DNA (Ellison, J. W., et al. (1982) *Nucl. Acids. Res.* 10:4071–4079) into the multiple cloning site of cloning vector pSP72 (Promega, Madison, Wis.). Plasmid pSP72lgG1 contained genomic DNA encoding the CH1, hinge, CH2 and CH3 domains of the heavy chain human IgCγ1 gene. PCR primers designed to amplify the hinge-CH2-CH3 portion of the heavy chain along with the intervening DNA were prepared as follows. The forward PCR primer 5'-GCATTTTAAGCTTTTTCCTGATCAGGAGCCC-AAATCTTCT GACAAAACTCACACATCTCCACCGT-CTCCAGGTAAGCC-3' (SEQ ID NO:36) contained HindIII and Bcl I restriction sites and was homologous to the hinge domain sequence except for five nucleotide substitutions which would change the three cysteine residues to serines. The reverse PCR primer 5'TAATACGACTCACTATAGGG-3' (SEQ ID NO:37) was identical to the commercially available T7 primer (Promega, Madison, Wis.). Amplification with these primers yielded a 1050 bp fragment bounded on the 5' end by HindIII and BclI restriction sites and on the 3' end by BamH1, Sma1, Kpn1, Sac1, EcoR1, Cla1, EcoR5 and Bglll restriction sites. This fragment contained the IgC hinge domain in which the three cysteine codons had been replaced by serine codons followed by an intron, the CH2 domain, an intron, the CH3 domain and additional 3' sequences. After PCR amplification, the DNA fragment was digested with Hindlll and EcoR1 and cloned into expression vector pNRDSH digested with the same restriction enzymes. This created plasmid pNRDSH/IgG1.

A similar PCR based strategy was used to clone the hinge-CH2-CH3 domains of human IgCgamma4 constant regions. A plasmid, p428D (Medical Research Council, London, England) containing the complete IgCgamma4 heavy chain genomic sequence (Ellison, J. Buxbaum, J. and Hood, L. E. (1981) *DNA* 1:11–18) was used as atemplate for PCR amplification using oligonucleotide 5'GAGCATTTTC-CTGATCAGGA GTCCAAATATGGTCCCCC-ATCCCATCATCCCCAGGTAAGCCAACCC-3' (SEQ ID NO:38) as the forward PCR primer and oligonucleotide 5'GCAGAGGAATCGAGCTCGGTACCCGGG-GATCCCCAGTGTGGGGACAGTGGGA CCGCTCTGCCTCCC-3' (SEQ ID NO:39) as the reverse PCR primer. The forward PCR primer (SEQ ID NO:38) contains a Bcl1 restriction site followed by the coding sequence for the hinge domain of IgCgamma4. Nucleotide substitutions have been made in the hinge region to replace the cysteines residues with serines. The reverse PCR primer (SEQ ID NO:39) contains a PspAI restriction site (5° C.CCGGG-3'). PCR amplification with these primers results in a 1179 bp DNA fragment. The PCR product was digested with BclI and PspAI and ligated to pNRDSH/IgG1 digested with the same restriction enzymes to yield plasmid pNRDSH/IgG4. In this reaction, the IgCγ4 domain replaced the IgCγ1 domain present in pNRDSH/IgG1.

Modification of the CH2 domain in IgC to replace amino acids thought to be involved in binding to Fc receptor was accomplished as follows. Plasmid pNRDSH/IgG1 served as template for modifications of the IgCγ1 CH2 domain and plasmid pNRDSH/IgG4 served as template for modifications of the IgCγ4 CH2 domain. Plasmid pNRDSH/IgG1 was PCR amplified using a forward PCR primer (SEQ ID NO:36) and oligonucleotide 5'-GGGTTTT GGGGGGAA-GAGGAAGACTGACGGTGCCCCC TCGGCTTCAGGTGCTGAGGAAG-3' (SEQ ID NO:40) as the reverse primer. The forward PCR primer (SEQ ID NO:36) has been previously described and the reverse PCR primer (SEQ ID NO:40) was homologous to the amino terminal portion of the CH2 domain of IgG1 except for five nucleotide substitutions designed to change amino acids 234, 235, and 237 (Canfield, S. M. and Morrison, S. L. (1991) *J. Exp. Med.* 173: 1483–1491.) from Leu to Ala, Leu to Glu, and Gly to Ala, respectively. Amplification with these PCR primers will yield a 239 bp DNA fragment consisting of a modified hinge domain, an intron and modified portion of the CH2 domain. Plasmid pNRDSH/IgG1 was also PCR amplified with the oligonucleotide 5'-CATCTCTTCCTCAGCACCTGAAGCCGAGGGGG-CACCGTCAGTCTTCCTCTTCCC (SEQ ID NO:) as the forward primer and ligonucleotide (SEQ ID NO:) as the reverse PCR primer. The forward PCR primer (SEQ ID NO:41) is complementary to primer (SEQ ID NO:40) and contains the five complementary nucleotide changes necessary for the CH2 amino acid replacements. The reverse PCR primer (SEQ ID NO:37) has been previously described. Amplification with these primes yields a 875 bp fragment consisting of the modified portion of the CH2 domain, an intron, the CH3 domain, and 3' additional sequences. The complete IgCγ1 segment consisting of modified hinge domain, modified CH2 domain and CH3 domain was prepared by an additional PCR reaction. The purified products of the two PCR reactions above were mixed, denatured (95° C.,1 minute) and then renatured (54° C., 30 seconds) to allow complementary ends of the two fragments to anneal. The strands were filled in using dNTP and Taq polymerase and the entire fragment amplified using forward PCR primer (SEQ ID NO:36) and reverse PCR primer (SEQ ID NO:37). The resulting fragment of 1050 bp was purified, digested with HindII and EcoR1 and ligated to pNRDSH previously digested with the same restriction enzymes to yield plasmid pNRDSHIgG1 m.

Two amino acids at immunoglobulin positions 235 and 237 were changed from Leu to Glu and Gly to Ala, respectively, within the IgCγ4 CH2 domain to eliminate Fc receptor binding. Plasmid pNRDSH/IgG4 was PCR amplified using the forward primer (SEQ ID NO: 38) and the oligonucleotide 5' -CGCACGTGACCTCAGGGG-TCCGGGAGATCATGAGAGTGCCT-TGGGTTTTGGGG GGAACAGGAAGACTGATGG-TGCCCCCTCGAACTCAGGTGCTGAGG-3' (SEQ ID NO:42) as the reverse primer. The forward primer has been previously described and the reverse primer was homologous to the amino terminal portion of the CH2 domain, except for three nucleotide substitutions designed to replace the amino acids described above. This primer also contained a PmlI restriction site for subsequent cloning. Amplification with these primers yields a 265 bp fragment composed of the modified hinge region, and intron, and the modified 5' portion of the CH2 domain.

Plasmid pNRDSH/1gG4 was also PCR amplified with the oligonucleotide 5 '-CCTCAGCACCTGAGTTCGA-GGGGGCACCATCAGTCTCCTGTTCCCCCC AAAAC-CCAAGGA CACTCTCATGATCTCCC GGACCCC-TGAGGTCACGTGCG-3' (SEQ ID NO:43) as the forward primer and oligonucleotide (SEQ ID NO:39) as the reverse PCR primer. The forward PCR primer (SEQ ID NO:43) is complimentary to primer (SEQ ID NO:42) and contains the three complementary nucleotide changes necessary for the CH2 amino acid replacements. The reverse PCR primer (SEQ ID NO:39) has been previously described. Amplification with these primers yields a 1012 bp fragment consisting of the modified portion of the CH2 domain, an intron, the CH3 domain, and 3' additional sequences. The complete IgCγ4 segment consisting of modified hinge domain, modified CH2 domain and CH3 domain was prepared by an additional PCR reaction. The purified products of the two PCR reactions above were mixed, denatured (95° C.,1 minute) and then renatured (54° C., 30 seconds) to allow complementary ends of the two fragments to anneal. The strands were filled in using DNTP and Taq polymerase and the entire fragment amplified using forward PCR primer (SEQ ID NO:38) and reverse PCR primer (SEQ ID NO:39). The resulting fragment of 1179 bp was purified, digested with BclI and PspAI and ligated to pNRDSH previously digested with the same restriction enzymes to yield plasmid pNRDSH/IgG4m.

(4). Assembly of Final hB7-2Ig Genes

The PCR fragment corresponding to the Ig signal-hB7-2 gene fusion prepared above was digested with BsaI and Bcl1 restriction enzymes and ligated to pNRDSH/IgG1, pNRDSH/IgG1m, pNRDSH/IgG4, and pNRDSH/IgG4m previously digested with Hind III and BclI. The ligated plasmids were transformed into *E. coli* JM109 using CaCl$_2$ competent cells and transformants were selected on L-agar containing ampicillin (50 μg/ml; Molecular Cloning: A Laboratory Manual (1982) Eds. Maniatis, T., Fritsch, E. E., and Sambrook, J. Cold Spring Harbor Laboratory). Plasmids isolated from the transformed *E. coli* were analyzed by restriction enzyme digestion. Plasmids with the expected restriction plasmid were sequenced to verify all portions of the signal-hB7-2-IgG gene fusion segments.

D. Expression Cloning of hB7-2V-IgG1 and hB7-2C IgG1

The variable and constant domains of human B7-2 were separately cloned into pNRDSH/IgG1. These clonings were accomplished using PCR. The portions of hB7-2 corresponding to the variable and constant regions were determined from intron/exon mapping and previously published gene structure analysis.

```
Human B7-2 Variable Domain
5'GCTCCTCTGAAGATT...................GAACTGTCAGTGCTT3'      (SEQ ID NO:44)
```

```
          -continued
    A  P  L  K  I                      E  L  S  V  L    (SEQ ID NO:45)

Human B7-2 Constant Domain
    5'GCTAACTTCAGTCAA.....................CCTTTCTCTATAGAG3'  (SEQ ID NO:46)
       A  N  F  S  Q                  P  F  S  I  E    (SEQ ID NO:47)
```

(1). Assembly of hB7-2VIg

The hB7-2V domain Ig sequence was assembled using a PCR strategy similar to that shown above. The signal sequence was derived from the onco M gene by PCR amplification of a plasmid containing the onco M gene using oligonucleotide 5'-GCAACCGGAAGCTTGCCA-CCATGGGGGTACTGCTCACACAGAGGACG-3' (#05) (SEQ ID NO:48) as the forward PCR primer and 5'-AGTCTCATTGAAATAAGCTTGAATCTTCAGAGG-AGCCATGCTGGCCATGCTTGGAAACAGGAG-3' (#06) (SEQ ID NO:49) as the reverse primer. The forward PCR primer (#05) (SEQ ID NO:48) contains a Hind III restriction site and the amino terminal portion of the onco M signal sequence. The reverse PCR (#06) (SEQ ID NO:49) contains the sequence corresponding to the 3' portion of the onco M signal sequence fused to the 5' end of the hB7-2 IgV like domain.

The hB7-2 IgV like domain was obtained by PCR amplification of the hB7-2 cDNA using oligonucleotide 5'-CTCCTGTTTCCAAGCATGGCCAGCATGGCTCCT-CTGAA GATTCAGGCTTATTTCAATGAGAC-3' (#07) (SEQ ID NO:50) as the forward and oligonucleotide 5'-TGTGTGTGGAATTCTCATTACTGATCAAGCACT-GACAGTTCAGAATTCATC-3' (#08) (SEQ ID NO:51) as the reverse PCR primer. PCR amplification with these primers yields the hB7-2 IgV domain with a portion of the 3' end of the onco M signal sequence on the 5' end and a Bcl I restriction site on the 3' end. The signal and IgV domain were linked together in a PCR reaction in which equimolar amounts of the onco M signal and IgV domain DNA fragments were mixed, denatured, annealed, and the strands filled in. Subsequent PCR amplification using forward primer #05 (SEQ ID NO:48) and reverse primer #08 (SEQ ID NO:51) yielded a DNA fragment containing a Hind III restriction site, followed by the onco M signal fused to the B7-2 IgV domain followed by a Bcl I restriction site. This PCR fragment was digested with Hind II and Bcl I and cloned into expression vector pNRDSH/IgG1 digested with the same restriction enzymes to yield pNRDSH/B7-2CIg.

(2). Assembly of hB7-2CIg

The expression plasmid for hB7-2IgC domain was prepared as described above for the IgV domain except for using PCR primers specific for the IgC domain. The onco M signal sequence was prepared using oligonucleotide #05 (SEQ ID NO:48) as the forward PCR primer and oligonucleotide 5'-AGAAATTGGTACTATTTCAGGTT- GACT-GAAGTTAGCCATGCTGGCCATGCTTGGA AACAGGAG-3' (#09) (SEQ ID NO:52) as the reverse PCR primer. The hB7-2 IgC domain was prepared using oligonucleotide 5'-CTCCTGTTTCCAAGCATGGCCA-GCATGGCTAACTTCAGTC AACCTGAAA-TAGTACCAATTTC-3' (#11) (SEQ ID NO:53) as the reverse PCR primer. The two PCR products were mixed and amplified with primers #05 (SEQ ID NO:48) and #11 (SEQ ID NO:53) to assemble the onco M signal sequence with the hB7-2IgC domain. The PCR product was subsequently digested with Hind III and BclI and ligated to pNRDSH/IgG1 digested with similar restriction enzymes to yield the final expression plasmid pNRDSH/hB7-2CIgG1.

E. Competition Binding Assays With Human B7-2Ig Fusion Proteins

The ability of various B7 family-Ig fusion proteins to competitively inhibit the binding of biotinylated-CTLA4Ig to immobilized B7-2Ig was determined. Competition binding assays were done as follows and analysed according to McPherson (McPherson, G. A. (1985) *J. Pharmacol. Methods* 14:213–228). Soluble hCTLA4Ig was labelled with $^{125}$I to a specific activity of approximately $2\times10^6$ cpm/pmol. hB7-2-Ig fusion protein was coated overnight onto microtiter plates at 10 µg/ml in 10 mM Tris-HCl, pH8.0, 50 µl/well. The wells were blocked with binding buffer (DMEM containing 10% heat-inactivated FBS, 0.1% BSA, and 50 mM BES, pH 6.8) for 2 h at room temperature. The labeled CTLA4-Ig (4 nM) was added to each well in the presence or absence of unlabeled competing Ig fusion proteins, including full-length B7-2 (hB7-21g), full-length B7-1 (hB7-1Ig), the variable region-like domain of B7-2 (B7-2VIg) and the constant region-like domain of B7-2 (hB7-2CIg) and allowed to bind for 2.5 h at room temperature. The wells were washed once with ice-cold binding buffer and then four times with ice-cold PBS. Bound radioactivity was recovered by treatment of the wells with 0.5 N NaOH for 5 min and the solubilized material removed and counted in a gamma counter.

Figure 15:
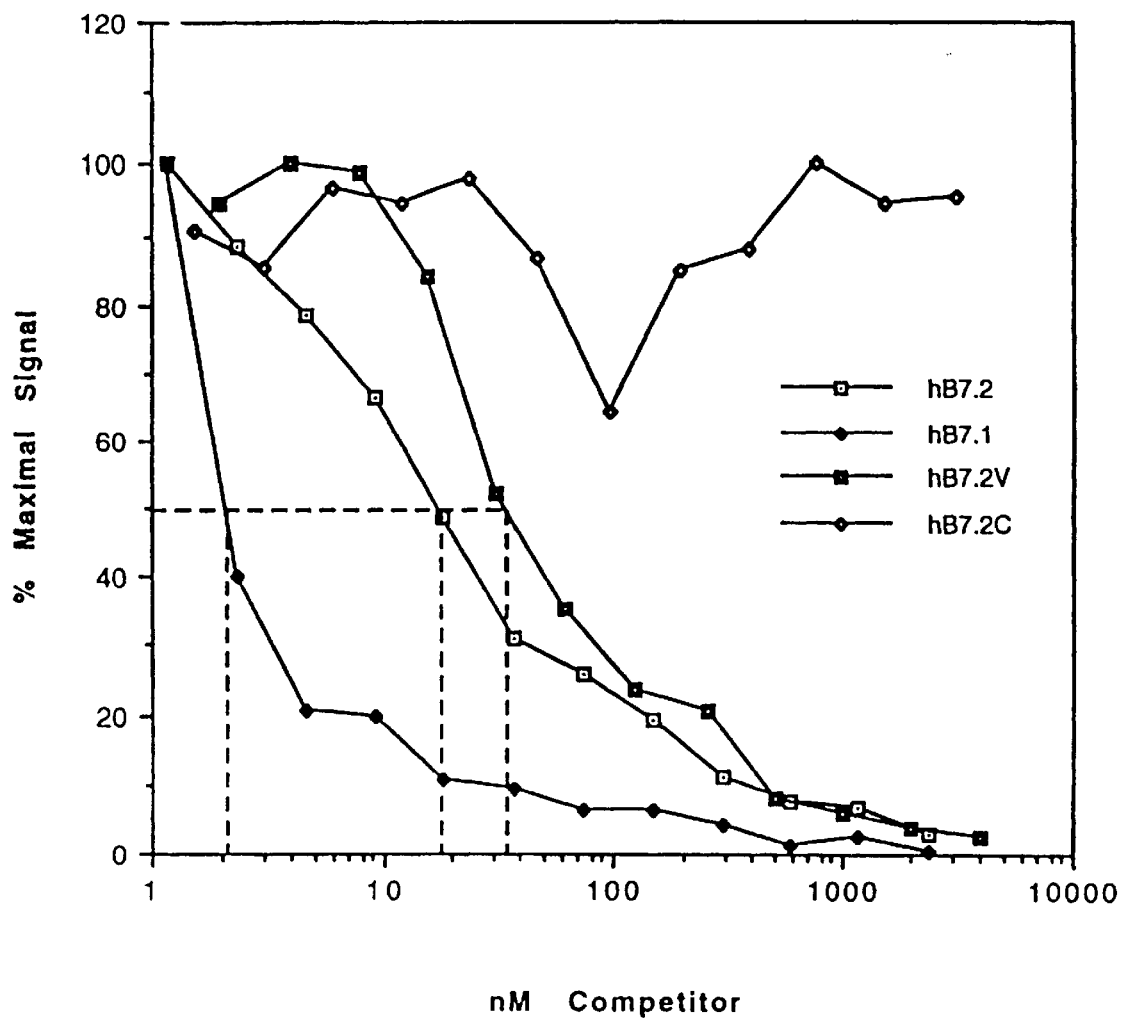
FIG. 15 is a graphic representation of the competitive inhibition of binding of biotinylated-CTLA4Ig to immobilized B7-2 Ig by B7 family-Ig fusion proteins. The Ig fusion proteins examined as competitors were: full-length B7-2 (hB7.2), full-length B7-1 (hB7.1), the variable region-like domain of B7-2 (hB7.2V) or the constant region-like domain of B7-2 (hB7.2C).

The results of these assays are shown in FIG. 15 in which both hB7-2Ig (10–20 nM) and hB7-2VIg (30–40 nM) competitively inhibit the binding of CTLA4Ig to immobilized B7 -2 protein. hB7-2CIg is unable to compete with soluble CTLA4, indicating that the B7-2 binding region is in found in the variable-region like domain.

F. Competitive binding Assays for B7-1 and B7-2 Fusion Proteins

Figure 16A:
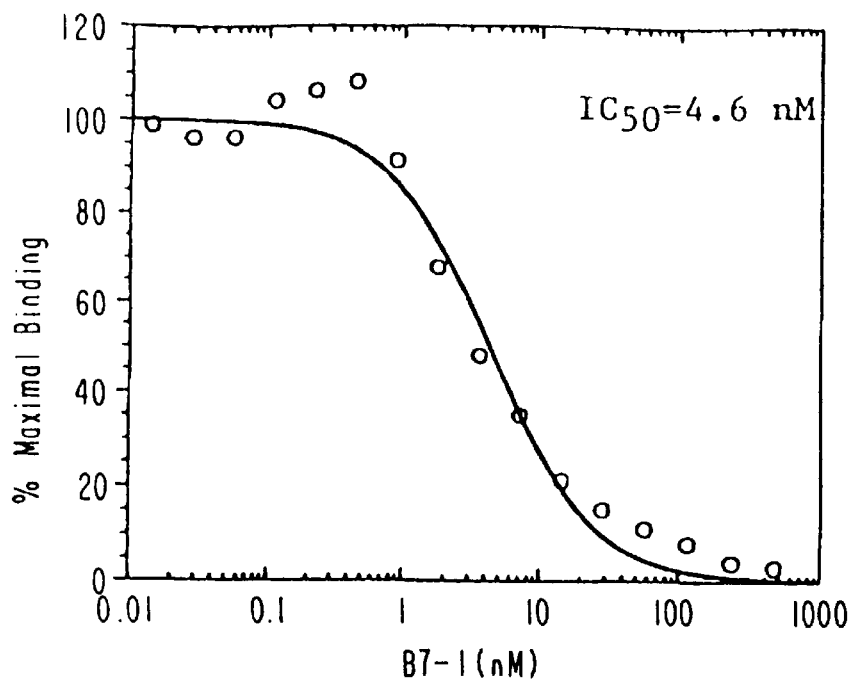
FIGS. 16A–B are graphic representations of the competitive inhibition of binding of biotinylated-B7-1-Ig (panel A) or B7-2-Ig (panel B) to immobilized CTLA4-Ig by increasing concentrations of unlabelled B7-1-Ig (panel A) or B7-2-Ig (panel B). The experimentally determined IC$_{50}$ values are indicated in the upper right corner of the panels.
Figure 16B:
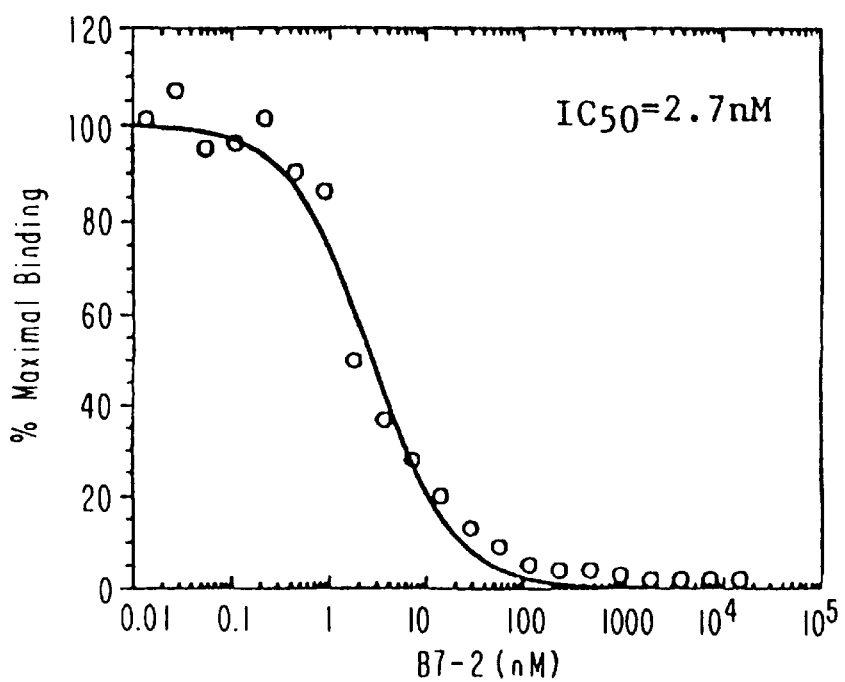

The ability of the various recombinant CTLA4 forms to bind to hB7-1 or hB7-2 was assessed in a competitive binding ELISA assay as follows. Purified recombinant hB7-Ig (20 µg/ml in PBS) was bound to a Costar EIA/RIA 96 well microtiter dish (Costar Corp, Cambridge Mass., USA) in 50 µL overnight at room temperature. The wells were washed three times with 200 µL of PBS and the unbound sites blocked by the addition of 1% BSA in PBS (200/well) for 1 hour at room temperature. The wells were washed as above. Biotinylated hCTLA4IgG1 (ref, MFGR;1 µg/ml serially diluted in twofold steps to 15.6 ng/mL; 50 µL) was added to each well and incubated for 2.5 hours at room temperature. The wells were washed as above. The bound biotinylated CTLA4Ig was detected by the addition of 50 l/l of a 1:2000 dilution of streptavidin-HRP (Pierce Chemical Co., Rockford, Ill.) for 30 minutes at room temperature. The wells were washed as above and 50 µL of ABTS (Zymed, Calif.) added and the developing blue color monitored at 405 nm after 30 min. A graphic representation of a typical binding assay is shown in FIG. 16. The ability of the various forms of CTLA4 to compete with biotinylated CTLA4IgG1 was assessed by mixing varying amounts of the competing protein with a quantity of biotinylated CTLA4IgG1 shown to be non-saturating (i.e., 70 ng/mL; 1.5nM) and performing the binding assays as described above (FIG. 15). A reduction in the signal (Abs 405 nm) expected for biotinylated CTLA4IgG1 indicated a competition for binding to hB7-1.

Considering the previous evidence that CTLA4 was the high affinity receptor for B7-1, the avidity of binding of CTLA4 and CD28 to B7-1 and B7-2 was compared. B7-1-Ig or B7-2-Ig was labelled with biotin and bound to immobilized CTLA4-Ig in the presence or absence of increasing concentrations of unlabeled B7-1-Ig or B7-2-Ig. The experiment was repeated with $^{125}$-I-labeled B7-1-Ig or B7-2-Ig. Using this solid phase binding assay, the avidity of B7-2 (2.7 nM) for CTLA4 was determined to be approximately two-fold greater than that observed for B7-1 (4.6 nM). The experimentally determined $IC_{50}$ values are indicated in the upper right corner of the panels. The affinity of both B7-1 and B7-2 for CD28 was lower and was difficult to confidently determine.

EXAMPLE 8

Production and Characterization of Monoclonal Antibodies to Human B7-2

A. Immunizations and Cell Fusions

Balb/c female mice (obtained from Taconic Labs, Germantown, N.Y.) were immunized intraperitoneally with 50 μg human B7.2-Ig emulsified in complete Freund's adjuvant (Sigma Chemical Co., St. Louis, Mo.) or $10^6$ CHO-human B7.2 cells per mouse. The mice were given two booster immunizations with 10–25 μg human B7.2-Ig emulsified in incomplete Freund's adjuvant (Sigma Chemical Co., St. Louis, Mo.) or CHO-human B7.2 cells at fourteen day intervals following the initial immunization for the next two months. The mice were bled by retro-orbital bleed and the sera assayed for the presence of antibodies reactive to the immunogen by ELISA against human B7.2-Ig. ELISA against hCTLA4-Ig was also used to control for Ig tail directed antibody responses. Mice showing a strong serological response were boosted intravenously via the tail vein with 25 μg human hB7.2-Ig diluted in phosphate-buffered saline (PBS), pH 7.2 (GIBCO, Grand Island, N.Y.). Three to four days following this boost, the spleens from these mice were fused 5:1 with SP 2/0 myeloma cells (American Type Culture Collection, Rockville, Md., No. CRL8006), which are incapable of secreting both heavy and light immunoglobulin chains (Kearney et al. (1979) *J. Immunol.* 123:1548). Standard methods based upon those developed by Kohler and Milstein (*Nature* (1975) 256:495) were used.

B. Antibody Screening

After 10–21 days, supernatants from wells containing hybridoma colonies from the fusion were screened for the presence of antibodies reactive to human B7.2 as follows: Each well of a 96 well flat bottomed plate (Costar Corp., Cat. #3590) was coated with 50 μl per well of a 1 μg/ml human B7.2-Ig solution or 5×10$^4$ 3T3-hB7.2 cells on lysine coated plates in phosphate-buffered saline, pH 7.2, overnight at 4° C.. The human B7.2-Ig solution was aspirated off, or the cells were cross-linked to the plates with glutaraldehyde, and the wells were washed three times with PBS, then blocked with 1% BSA solution (in PBS) (100 μl/well) for one hour at room temperature. Following this blocking incubation, the wells were washed three times with PBS and 50 μl of hybridoma supernatant was added per well and incubated for 1.5 hours at room temperature. Following this incubation, the wells were washed three times with PBS and then incubated for 1.5 hours at room temperature with 50 μl per well of a 1:4000 dilution of horseradish peroxidase-conjugated, affinity purified, goat anti-mouse IgG or IgM heavy and light chain-specific antibodies (HRP; Zymed Laboratories, San Francisco, Calif.). The wells were then washed three times with PBS, followed by a 30 minute incubation in 50 μl per well of 1 mM 2,2-azino-bis-3-ethylbenzthiazoline-6-sulfonic acid (ABTS) in 0.1 M Na-Citrate, pH 4.2 to which a 1:1000 dilution of 30% hydrogen peroxide had been added as a substrate for HRP to detect bound antibody. The absorbence was then determined at $OD_{410}$ on a spectrophotometric autoreader (Dynatech, Virginia).

Three hybridomas, HA3.1F9, HA5.2B7 and HF2.3D1, were identified that produced antibodies to human B7.2-Ig. HA3.1F9 was determined to be of the IgG1 isotype, HA5.2B7 was determined to be of the IgG2b isotype and HF2.3D1 as determined to be of the IgG2a isotype. Each of these hybridomas were subcloned two additional times to insure that they were monoclonal. Hybidoma cells were deposited with the American Type Culture Collection, which meets the requirements of the Budapest Treaty, on Jul. 19, 1994 as ATCC Accession No. HB 11688 (hybridoma HA3.1F9), ATCC Accession No. HB 11687 (HA5.2B7) and ATCC Accession No. HB 11686 (HF2.3D1).

C. Competitive ELISA

Supernatants from the hybridomas HA3.1F9, HA5.2B7 and HF2.3D1 were further characterized by competitive ELISA, in which the ability of the monoclonal antibodies to inhibit the binding of biotinylated hCTLA4Ig to immobilized hB7-2 immunoglobulin fusion proteins was examined. Biotinylation of hCTLA4Ig was performed using Pierce Immunopure NHS-LC Biotin (Cat. No. 21335). B7-2 immunoglobulin fusion proteins used were: hB7.2-Ig (full-length hB7-2), hB7.2-VIg (hB7-2 variable domain only) and hB7.2-CIg (B7-2 constant domain only). A hB7.1 -Ig fusion protein was used as a control. For the ELISA, 96 well plates were coated with the Ig fusion protein (50 μl/well of a 20 μg/ml solution) overnight at room temperature. The wells were washed three times with PBS, blocked with 10% fetal bovine serum (FBS), 0.1% bovine serum albumin (BSA) in PBS for 1 hour at room temperature, and washed again three times with PBS. To each well was added 50 μl of Bio-hCTLA4-Ig (70 ng/ml) and 50 μl of competitor monoclonal antibody supernatant. Control antibodies were an anti-B7.1 mAb (EW3.5D12) and the anti-hB7-2 mAb B70 (IgG2bκ, obtained from Pharmingen). The wells were washed again and streptavidin-conjugated horse radish peroxidase (from Pierce, Cat. No. 21126; 1:2000 dilution, 50 μl/well) was added and incubated for 30 minutes at room temperature. The wells were washed again, followed by a 30 minute incubation in 50 μl per well of ABTS in 0.1 M Na-Citrate, pH 4.2 to which a 1:1000 dilution of 30% hydrogen peroxide had been added as a substrate for HRP to detect bound antibody. The absorbence was then determined at $OD_{410}$ on a spectrophotometric autoreader (Dynatech, Virginia). The results, shown in Table IV below, demonstrate that each of the mAbs produced by the hybridomas HA3.1F9, HA5.2B7 and HF2.3D1 are able to competitively inhibit the binding of hCLTA4Ig to full-length hB7.2-Ig or hB7.2-VIg (hCTLA4Ig does not bind to hB7.2CIg).

TABLE IV

|  | Blocking of Binding | | | |
| --- | --- | --- | --- | --- |
|  | hB7.1-Ig | hB7.2-Ig | hB7.2-VIg | hB7.2-CIg |
| EW3.5D12 (anti-hB7.1 mAb) | Yes | No | No | No |
| B70 (anti-hB7-2) | No | Yes | Yes | No |
| HA3.1F9 (anti-hB7-2) | No | Yes | Yes | No |
| HA5.2B7 (anti-hB7-2) | No | Yes | Yes | No |
| HF2.3D1 (anti-hB7-2) | No | Yes | Yes | No |

D. Flow Cytometry

Figure 17B:
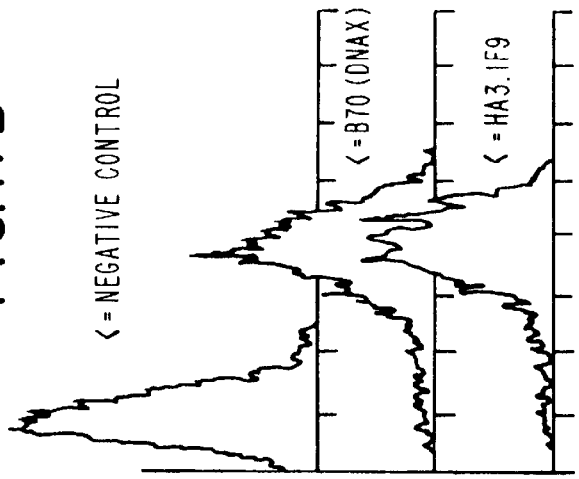
FIG. 17 depicts flow cytometric profiles of cells stained with an anti-hB7-2 monoclonal antibody, HA3.1F9. Cells stained with the antibody were CHO cells transfected to express human B7-2 (CHO-hB7.2), NIH 3T3 cells transfected to express human B7-2 (3T3-hB7.2) and control transfected NIH 3T3 cells (3T3-neo). The anti-hB7.2 antibody B70 was used as a positive control.
Figure 17C:
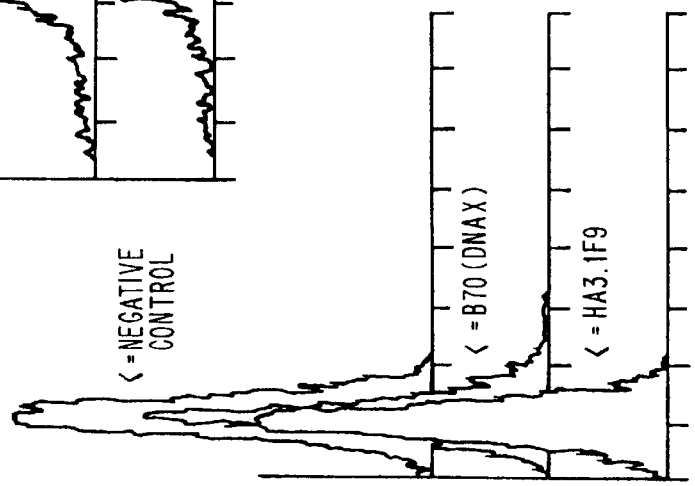
Figure 17A:
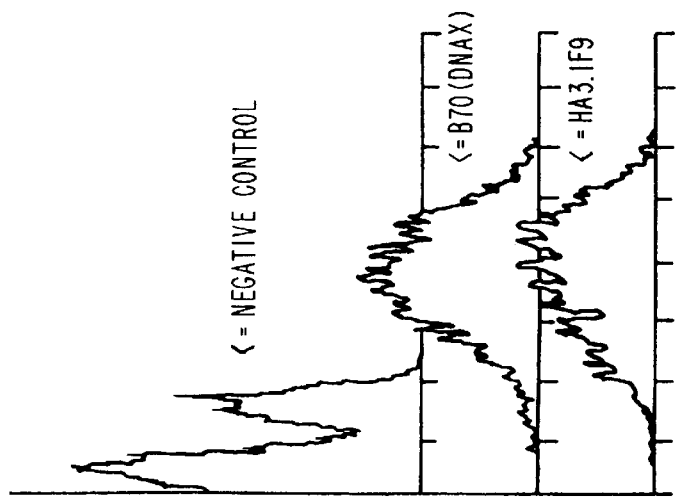
Figure 18B:
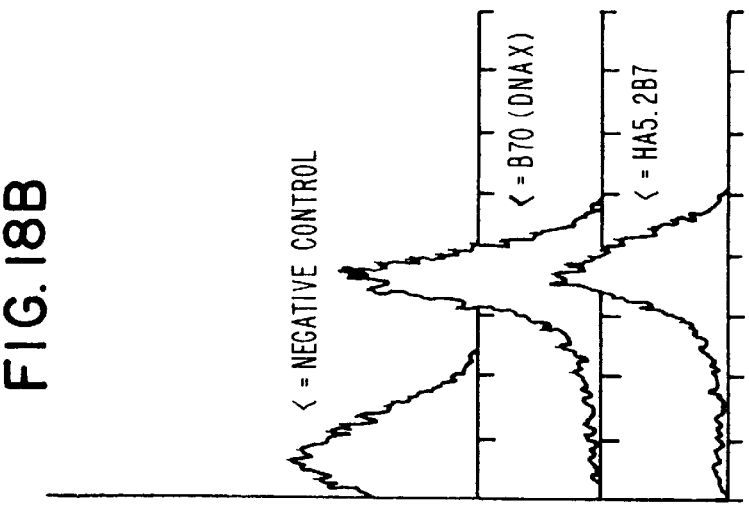
FIG. 18 depicts flow cytometric profiles of cells stained with an anti-hB7-2 monoclonal antibody, HA5.2B7. Cells stained with the antibody were CHO cells transfected to express human B7-2 (CHO-hB7.2), NIH 3T3 cells transfected to express human B7-2 (3T3-hB7.2) and control transfected NIH 3T3 cells (3T3-neo). The anti-hB7.2 antibody B70 was used as a positive control.
Figure 18C:
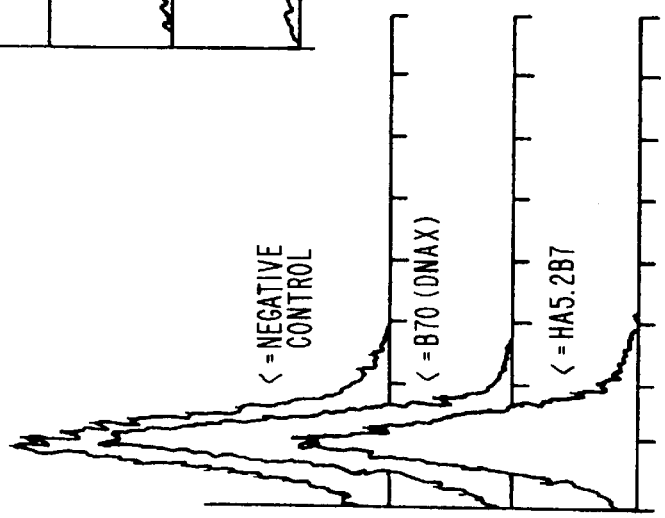
Figure 18A:
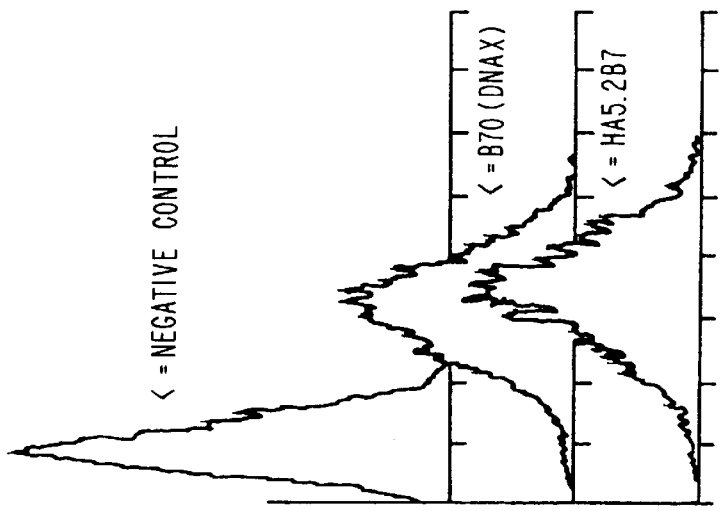
Figure 19B:
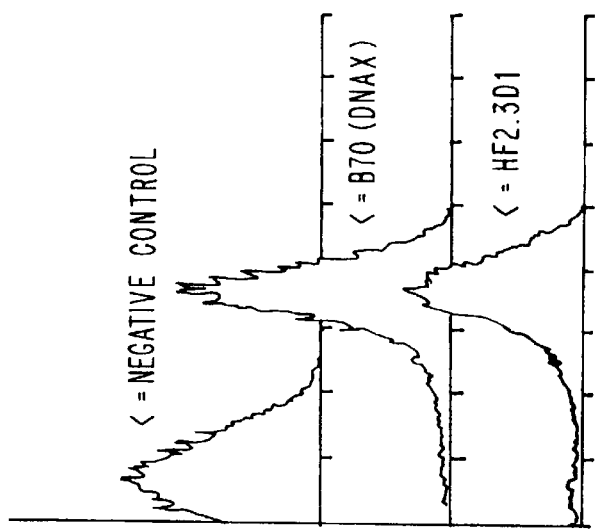
FIG. 19 depicts flow cytometric profiles of cells stained with an anti-hB7-2 monoclonal antibody, HF2.3D1. Cells stained with the antibody were CHO cells transfected to express human B7-2 (CHO-hB7.2), NIH 3T3 cells transfected to express human B7-2 (3T3-hB7.2) and control transfected NIH 3T3 cells (3T3-neo). The anti-hB7.2 antibody B70 was used as a positive control.
Figure 19C:
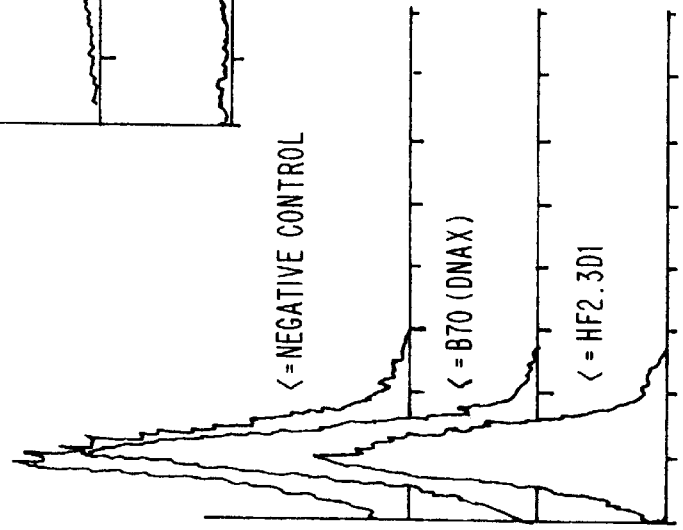
Figure 19A:
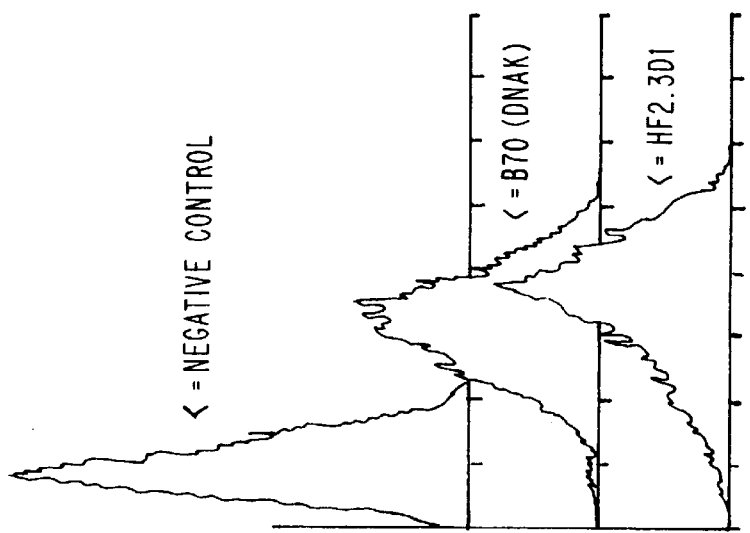

Supernatants from the hybridomas HA3.1F9, HA5.2B7 and HF2.3D1 were also characterized by flow cytometry. Supernatants collected from the clones were screened by flow cytometry on CHO and 3T3 cells transfected to express hB7.2 (CHO-hB7.2 and 3T3-hB7.2, respectively) or control transfected 3T3 cells (3T3-Neo). Flow cytometry was performed as follows: 1×10⁶ cells were washed three times in 1% BSA in PBS, then the cells were incubated in 50 µl hybridoma supernatant or culture media per 1×10⁶ cells for 30 minutes at 4° C.. Following the incubation, the cells were washed three times with 1% BSA in PBS, then incubated in 50 µl fluorescein-conjugated goat anti-mouse IgG or IgM antibodies (Zymed Laboratories, San Francisco, Calif.) at 1:50 dilution per 1×10⁶ cells for 30 minutes at 4° C.. The cells were then washed three times in 1% BSA in PBS and fixed with 1% paraformaldehyde solution. The cell samples were then analyzed on a FACScan flow cytometer (Becton Dickinson, San Jose Calif.). The results, shown in FIGS. 17, 18 and 19, demonstrate the monoclonal antibodies produced by the hybridomas HA3.1F9, HA5.2B7 and HF2.3D1 each bind to hB7-2 on the surface of cells.

E. Inhibition of Proliferation of Human T Cells by Anti-hB7-2 mAbs

Hybridoma supernatants containing anti-human B7-2 mAbs were tested for their ability to inhibit hB7-2 costimulation of human T cells. In this assay, purified CD28⁺ human T cells were treated with submitogenic amounts of PMA (1 ng/ml) to deliver the primary signal and with CHO cells expressing hB7-2 on their surface to deliver the costimulatory signal. Proliferation of the T cells was measured after three days in culture by the addition of ³H-thymidine for the remaining 18 hours. As shown in Table V, resting T cells show little proliferation as measured by ³H-thymidine incorporation (510 pm). Delivery of signal 1 by PMA results in some proliferation (3800 pm) and T cells receiving both the primary (PMA) and costimulatory (CHO/hB7-2) signals proliferate maximally (9020 cpm). All three anti-hB7-2 mAbs tested reduce the costimulatory signal induced proliferation to that found for PMA treated cells alone showing that these mAbs can inhibit T cell proliferation by blocking the B7/CD28 costimulatory pathway.

TABLE V

| Addition to CD28⁺ T Cells | hB7-2 mAb | CPM |
|---|---|---|
| — | — | 510 |
| +PMA | — | 3800 |
| +PMA + CHO/hB7-2 | — | 9020 |
| +PMA + CHO/hB7-2 | HF2.301 | 3030 |
| — | HA5.2B7 | 1460 |
| — | HA3.1F9 | 2980 |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule encoding a fusion protein comprising a first nucleotide sequence encoding a first peptide having the ability to bind CD28 or CTLA4, which first peptide has at least about 50% amino acid sequence identity with the extracellular domain of a human B7-2 peptide shown in FIG. 8 (SEQ ID NO:2) and a second nucleotide sequence encoding a second peptide.

2. The isolated nucleic acid molecule of claim 1, wherein said first peptide costimulates T cell proliferation or T cell cytokine production.

3. The isolated nucleic acid molecule of claim 1, wherein the first peptide comprises the extracellular domain of the human B7-2 peptide shown in FIG. 8 (SEQ ID NO:2).

4. The isolated nucleic acid molecule of claim 1, wherein the first peptide comprises amino acid residues 24–245 of the sequence shown in FIG. 8 (SEQ ID NO:2).

5. The isolated nucleic acid molecule of claim 1, wherein the first peptide comprises a variable region-like domain of the human B7-2 peptide shown in FIG. 8 (SEQ ID NO:2).

6. The isolated nucleic acid molecule of claim 1, wherein the first peptide comprises a constant region-like domain of the human B7-2 peptide shown in FIG. 8 (SEQ ID NO:2).

7. The isolated nucleic acid molecule of claim 1, wherein the second peptide comprises an immunoglobulin constant region.

8. The isolated nucleic acid molecule of claim 7, wherein the immunoglobulin constant region is a Cγ1 domain, including the hinge, CH2 and CH3 region.

9. The isolated nucleic acid molecule of claim 7, wherein the immunoglobulin constant region is modified to reduce constant region-mediated biological effector functions.

10. The isolated nucleic acid molecule of claim 9, wherein the biological effector function is selected from the group consisting of: complement activation and Fc receptor interaction.

11. The isolated nucleic acid molecule of claim 10, wherein the immunoglobulin constant region is a Cγ4 domain, including the hinge, CH2 and CH3 region.

12. The isolated nucleic acid molecule of claim 11, wherein at least one amino acid residue of the CH2 domain is modified by substitution, addition or deletion.

13. The isolated nucleic acid molecule of claim 1, wherein said nucleic acid molecule comprises a nucleotide sequence encoding a first peptide having at least about 70% amino acid sequence identity with the extracellular domain of a human B7-2 peptide comprising the amino acid sequence shown in FIG. 8 (SEQ ID NO:2).

14. The isolated nucleic acid molecule of claim 1, wherein said nucleic acid molecule comprises a nucleotide sequence encoding a first peptide having at least about 80% amino acid sequence identity with the extracellular domain of a human B7-2 peptide comprising the amino acid sequence shown in FIG. 8 (SEQ ID NO:2).

15. The isolated nucleic acid molecule of claim 14, wherein said first peptide costimulates T cell proliferation or T cell cytokine production.

16. The isolated nucleic acid molecule of claim 1, wherein said nucleic acid molecule comprises a nucleotide sequence encoding a first peptide having at least about 90% amino acid sequence identity with the extracellular domain of a human B7-2 peptide comprising the amino acid sequence shown in FIG. 8 (SEQ ID NO:2).

17. An isolated nucleic acid molecule encoding a fusion protein, said nucleic acid molecule comprising a first nucleotide sequence encoding a first peptide and a second nucleotide sequence encoding a second peptide, wherein said first nucleotide sequence hybridizes in 6.0× sodium chloride/sodium citrate (SSC) at about 45° C., followed by a wash in about 0.2× SSC at a temperature of about 50° C. to a portion of the nucleotide sequence shown in SEQ ID NO:1 or SEQ ID NO:22 that encodes a B7-2 extracellular domain, said first peptide having the ability to bind CD28 or CTLA4.

18. The isolated nucleic acid molecule of claim 17, wherein said first peptide costimulates T cell proliferation or T cell cytokine production.

19. The isolated nucleic acid molecule of claim 17 which is a DNA or cDNA molecule.

20. An isolated nucleic acid molecule encoding a fusion protein comprising a first peptide having an amino acid sequence which is substantially identical to the amino acid sequence of the extracellular domain of the human B7-2 peptide shown in FIG. 8 (SEQ ID NO:2) and a second peptide, wherein the first peptide of the fusion protein binds CD28 or CTLA4, wherein said nucleic acid molecule is not identical. The nucleic acid molecule shown in SEQ ID NO:1.

21. The isolated nucleic acid molecule of claim 20, wherein said first peptide costimulates T cell proliferation or T cell cytokine production.

22. The isolated nucleic acid molecule of claim 20 which is a DNA or cDNA molecule.

23. An isolated fusion protein comprising a first peptide having the ability to bind CD28 or CTLA4, which peptide has at least 50% amino acid sequence identity with the extracellular domain of a human B7-2 peptide comprising the amino acid sequence shown in FIG. 8 (SEQ 1D NO:2) and a second peptide.

24. The isolated fusion protein of claim 23 wherein said first peptide costimulates T cell proliferation or T cell cytokine production.

25. The isolated fusion protein of claim 23, wherein the first peptide comprises amino acid residues 24–245 of the sequence shown in FIG. 8 (SEQ ID NO:2).

26. The isolated fusion protein of claim 23, wherein the first peptide comprises a variable region-like domain of the human B7-2 peptide shown in FIG. 8 (SEQ ID NO:2).

27. The isolated fusion protein of claim 23, wherein the first peptide comprises a constant region-like domain of the human B7-2 peptide shown in FIG. 8 (SEQ ID NO:2).

28. The isolated fusion protein of claim 23, wherein said first peptide has at least about 70% amino acid sequence identity with the extracellular domain of a human B7-2 peptide comprising the amino acid sequence shown in FIG. 8 (SEQ ID NO:2).

29. The isolated fusion protein of claim 23, wherein said first peptide has at least about 80% amino acid sequence identity with the extracellular domain of a human B7-2 peptide comprising the amino acid sequence shown in FIG. 8 (SEQ ID NO:2).

30. The isolated fusion protein of claim 23, wherein said first peptide has at least about 90% amino acid sequence identity with the extracellular domain of a human B7-2 peptide comprising the amino acid sequence shown in FIG. 8 (SEQ ID NO;2).

31. The isolated fusion protein of claim 30, wherein said first peptide has an amino acid sequence which differs from the amino acid sequence of the extracellular domain shown in FIG. 8 (SEQ ID NO:2) due to substitution, addition, or deletion of at least one amino acid residue.

32. The isolated fusion protein of claim 23, wherein the first peptide comprises the extracellular domain of the human B7-2 peptide shown in FIG. 8 (SEQ ID NO:2).

33. A composition comprising a fusion protein of claim 32 and a pharmaceutically acceptable carrier.

34. The isolated fusion protein of claim 24, wherein the second peptide comprises an immunoglobulin constant region.

35. The isolated fusion protein of claim 34, wherein the immunoglobulin constant region is a Cγ1 domain, including the hinge, CH2 and CH3 region.

36. The isolated fusion protein of claim 34, wherein the immunoglobulin constant region is modified to reduce constant region-mediated biological effector functions.

37. A composition comprising a fusion protein of claim 36 and a pharmaceutically acceptable carrier.

38. The isolated fusion protein of claim 38, wherein the biological effector function is selected from the group consisting of: complement activation and Fc receptor interaction.

39. The isolated fusion protein of claim 38, wherein the immunoglobulin constant region is a Cγ4 domain, including the hinge, CH2 and CH3 region.

40. The isolated nucleic acid molecule of claim 39, wherein at least one amino acid residue of the CH2 domain is modified by substitution, addition or deletion.

41. A composition comprising a fusion protein of claim 34 and a pharmaceutically acceptable carrier.

42. A composition comprising a fusion protein of claim 23 and a pharmaceutically acceptable carrier.

43. An isolated fusion protein comprising a first peptide having the ability to bind CD28 or CTLA4 and a second peptide, wherein The first peptide is encoded by a nucleic acid molecule which hybridizes in 6.0× sodium chloride/sodium citrate (SSC) at about 45° C., followed by a wash in about 0.2× SSC at a temperature of about 50° C. to a portion of the nucleotide sequence shown in SEQ ID NO:1 or SEQ ID NO:22 that encodes a B7-2 extracellular domain.

44. The isolated fusion protein of claim 43, wherein said first peptide costimulates T cell proliferation or T cell cytokine production.

45. The isolated fusion protein of claim 43, wherein said first peptide comprises an amino acid sequence selected from the group consisting of: SEQ ID NO:17, SEQ ID NO:1, and SEQ ID NO:19.

46. A composition comprising a fusion protein of claim 43 and a pharmaceutically acceptable carrier.

47. The isolated fusion protein of claim 43, wherein the first peptide comprises the extracellular domain of the human B7-2 peptide shown in FIG. 8 (SEQ ID NO:2).

48. A composition comprising a fusion protein of claim 47 and a pharmaceutically acceptable carrier.

49. The isolated fusion protein of claim 47, wherein the second peptide comprises an immunoglobulin constant region.

50. The isolated fusion protein of claim 49, wherein he immunoglobulin constant region is a Cγ1 domain, including the hinge, CH2 and CH3 region.

51. A composition comprising a fusion protein of claim 49 and a pharmaceutically acceptable carrier.

52. The isolated fusion protein of claim 49, wherein the immunoglobulin constant region is modified to reduce constant region-mediated biological effector functions.

53. A composition comprising a fusion protein of claim 52 and a pharmaceutically acceptable carrier.

54. The isolated fusion protein of claim 52, wherein the biological effector function is selected from the group consisting of: complement activation and Fc receptor interaction.

55. The isolated fusion protein of claim 54, wherein the immunoglobulin constant region is a Cγ4 domain, including the hinge, CH2 and CH3 region.

56. The isolated nucleic acid molecule of claim 55, wherein at least one amino acid residue of the CH2 domain is modified by substitution, addition or deletion.

57. A fusion protein comprising a first peptide substantially identical to the extracellular domain of the human B7-2 peptide comprising the amino acid sequence shown in FIG. 8 (SEQ ID NO:2) and a second peptide, wherein the first peptide of the fusion protein binds CD28 or CTLA4.

58. The fusion protein of claim 57, wherein said first peptide costimulates T cell proliferation or T cell cytokine production.

59. A composition comprising a fusion protein of claim 57 and a pharmaceutically acceptable carrier.

60. The isolated fusion protein of claim 57, wherein the first peptide comprises the extracellular domain of the human B7-2 peptide shown in FIG. 8 (SEQ ID NO:2).

61. A composition comprising a fusion protein of claim 60 and a pharmaceutically acceptable carrier.

62. The isolated fusion protein of claim 60, wherein the second peptide comprises an immunoglobulin constant region.

63. The isolated fusion protein of claim 62, wherein the immunoglobulin constant region is a Cγ1 domain, including the hinge, CH2 and CH3 region.

64. A composition comprising a fusion protein of claim 62 and a pharmaceutically acceptable carrier.

65. The isolated fusion protein of claim 62, wherein the immunoglobulin constant region is modified to reduce constant region-mediated biological effector functions.

66. A composition comprising a fusion protein of claim 65 and a pharmaceutically acceptable carrier.

67. The isolated fusion protein of claim 65, wherein the biological effector function is selected from the group consisting of: complement activation and Fc receptor interaction.

68. The isolated fusion protein of claim 67, wherein the immunoglobulin constant region is a Cγ4 domain, including the hinge, CH2 and CH3 region.

69. The isolated nucleic acid molecule of claim 68, wherein at least one amino acid residue of the CH2 domain is modified by substitution, addition or deletion.

* * * * *

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 1120 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 107..1093

(xi) SEQUENCE DESCRIPTION: SEQ ID NO:1:

```
CACAGGGTGA AAGCTTTGCT TCTCTGCTGC TGTAACAGGG ACTAGCACAG ACACACGGAT        60

GAGTGGGGTC ATTTCCAGAT ATTAGGTCAC AGCAGAAGCA GCCAAA ATG GAT CCC          115
                                                Met Asp Pro
                                                  1

CAG TGC ACT ATG GGA CTG AGT AAC ATT CTC TTT GTG ATG GCC TTC CTG         163
Gln Cys Thr Met Gly Leu Ser Asn Ile Leu Phe Val Met Ala Phe Leu
      5                  10                  15

CTC TCT GGT GCT GCT CCT CTG AAG ATT CAA GCT TAT TTC AAT GAG ACT         211
Leu Ser Gly Ala Ala Pro Leu Lys Ile Gln Ala Tyr Phe Asn Glu Thr
 20                  25                  30                  35

GCA GAC CTG CCA TGC CAA TTT GCA AAC TCT CAA AAC CAA AGC CTG AGT         259
Ala Asp Leu Pro Cys Gln Phe Ala Asn Ser Gln Asn Gln Ser Leu Ser
                 40                  45                  50

GAG CTA GTA GTA TTT TGG CAG GAC CAG GAA AAC TTG GTT CTG AAT GAG         307
```

```
Glu Leu Val Val Phe Trp Gln Asp Gln Glu Asn Leu Val Leu Asn Glu
         55                  60                  65

GTA TAC TTA GGC AAA GAG AAA TTT GAC AGT GTT CAT TCC AAG TAT ATG    355
Val Tyr Leu Gly Lys Glu Lys Phe Asp Ser Val His Ser Lys Tyr Met
         70                  75                  80

GGC CGC ACA AGT TTT GAT TCG GAC AGT TGG ACC CTG AGA CTT CAC AAT    403
Gly Arg Thr Ser Phe Asp Ser Asp Ser Trp Thr Leu Arg Leu His Asn
 85                  90                  95

CTT CAG ATC AAG GAC AAG GGC TTG TAT CAA TGT ATC ATC CAT CAC AAA    451
Leu Gln Ile Lys Asp Lys Gly Leu Tyr Gln Cys Ile Ile His His Lys
100                 105                 110                 115

AAG CCC ACA GGA ATG ATT CGC ATC CAC CAG ATG AAT TCT GAA CTG TCA    499
Lys Pro Thr Gly Met Ile Arg Ile His Gln Met Asn Ser Glu Leu Ser
                120                 125                 130

GTG CTT GCT AAC TTC AGT CAA CCT GAA ATA GTA CCA ATT TCT AAT ATA    547
Val Leu Ala Asn Phe Ser Gln Pro Glu Ile Val Pro Ile Ser Asn Ile
                135                 140                 145

ACA GAA AAT GTG TAC ATA AAT TTG ACC TGC TCA TCT ATA CAC GGT TAC    595
Thr Glu Asn Val Tyr Ile Asn Leu Thr Cys Ser Ser Ile His Gly Tyr
                150                 155                 160

CCA GAA CCT AAG AAG ATG AGT GTT TTG CTA AGA ACC AAG AAT TCA ACT    643
Pro Glu Pro Lys Lys Met Ser Val Leu Leu Arg Thr Lys Asn Ser Thr
165                 170                 175

ATC GAG TAT GAT GGT ATT ATG CAG AAA TCT CAA GAT AAT GTC ACA GAA    691
Ile Glu Tyr Asp Gly Ile Met Gln Lys Ser Gln Asp Asn Val Thr Glu
180                 185                 190                 195

CTG TAC GAC GTT TCC ATC AGC TTG TCT GTT TCA TTC CCT GAT GTT ACG    739
Leu Tyr Asp Val Ser Ile Ser Leu Ser Val Ser Phe Pro Asp Val Thr
                200                 205                 210

AGC AAT ATG ACC ATC TTC TGT ATT CTG GAA ACT GAC AAG ACG CGG CTT    787
Ser Asn Met Thr Ile Phe Cys Ile Leu Glu Thr Asp Lys Thr Arg Leu
                215                 220                 225

TTA TCT TCA CCT TTC TCT ATA GAG CTT GAG GAC CCT CAG CCT CCC CCA    835
Leu Ser Ser Pro Phe Ser Ile Glu Leu Glu Asp Pro Gln Pro Pro Pro
                230                 235                 240

GAC CAC ATT CCT TGG ATT ACA GCT GTA CTT CCA ACA GTT ATT ATA TGT    883
Asp His Ile Pro Trp Ile Thr Ala Val Leu Pro Thr Val Ile Ile Cys
                245                 250                 255

GTG ATG GTT TTC TGT CTA ATT CTA TGG AAA TGG AAG AAG AAG AAG CGG    931
Val Met Val Phe Cys Leu Ile Leu Trp Lys Trp Lys Lys Lys Lys Arg
260                 265                 270                 275

CCT CGC AAC TCT TAT AAA TGT GGA ACC AAC ACA ATG GAG AGG GAA GAG    979
Pro Arg Asn Ser Tyr Lys Cys Gly Thr Asn Thr Met Glu Arg Glu Glu
                280                 285                 290

AGT GAA CAG ACC AAG AAA AGA GAA AAA ATC CAT ATA CCT GAA AGA TCT   1027
Ser Glu Gln Thr Lys Lys Arg Glu Lys Ile His Ile Pro Glu Arg Ser
                295                 300                 305

GAT GAA GCC CAG CGT GTT TTT AAA AGT TCG AAG ACA TCT TCA TGC GAC   1075
Asp Glu Ala Gln Arg Val Phe Lys Ser Ser Lys Thr Ser Ser Cys Asp
                310                 315                 320

AAA AGT GAT ACA TGT TTT TAATTAAAGA GTAAAGCCCA AAAAAAA             1120
Lys Ser Asp Thr Cys Phe
            325
```

(2) INFORMATION FOR SEQ ID NO:2:

(i) SEQUENCE CHARACTERISTICS:
        (A) LENGTH: 329 amino acids
        (B) TYPE: amino acid
        (D) TOPOLOGY: linear -continued

```
    (ii) MOLECULE TYPE: protein (xi) SEQUENCE DESCRIPTION: SEQ ID NO:2:

Met Asp Pro Gln Cys Thr Met Gly Leu Ser Asn Ile Leu Phe Val Met
 1               5                  10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:3:
```

```
TAATACGACT CACTATAGGG                                           20

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:4:

TAAGGTTCCT TCACAAAG                                             18

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

ACTGGTAGGT ATGGAAGATC C                                         21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

ATGCGAATCA TTCCTGTGGG C                                         21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

AAAGCCCACA GGAATGATTC G                                         21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

CTCTCAAAAC CAAAGCCTGA G                                         21
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

TTAGGTCACA GCAGAAGCAG C                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

TCTGGAAACT GACAAGACGC G                                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

CTCAGGCTTT GGTTTTGAGA G                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CACTCTCTTC CCTCTCCATT G                                              21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

GACAAGCTGA TGGAAACGTC G                                              21

(2) INFORMATION FOR SEQ ID NO:14:

(i) SEQUENCE CHARACTERISTICS:
        (A) LENGTH: 21 base pairs (B) TYPE: nucleic acid
                (C) STRANDEDNESS: single
                (D) TOPOLOGY: linear (ii) MOLECULE TYPE: oligonucleotide (xi) SEQUENCE DESCRIPTION: SEQ ID NO:14:

CAATGGAGAG GGAAGAGAGT G                                              21

(2) INFORMATION FOR SEQ ID NO:15:

(i) SEQUENCE CHARACTERISTICS:
                (A) LENGTH: 12 base pairs
                (B) TYPE: nucleic acid
                (C) STRANDEDNESS: single
                (D) TOPOLOGY: linear (ii) MOLECULE TYPE: oligonucleotide (xi) SEQUENCE DESCRIPTION: SEQ ID NO:15:

CTTTAGAGCA CA                                                        12

(2) INFORMATION FOR SEQ ID NO:16:

(i) SEQUENCE CHARACTERISTICS:
                (A) LENGTH: 8 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:16:

CTCTAAAG                                                              8

(2) INFORMATION FOR SEQ ID NO:17:

(i) SEQUENCE CHARACTERISTICS:
                (A) LENGTH: 9 amino acids
                (B) TYPE: amino acid
                (D) TOPOLOGY: linear (ii) MOLECULE TYPE: peptide (xi) SEQUENCE DESCRIPTION: SEQ ID NO:17:

Lys Tyr Met Gly Arg Thr Ser Phe Asp
                  5

(2) INFORMATION FOR SEQ ID NO:18:

(i) SEQUENCE CHARACTERISTICS:
                (A) LENGTH: 13 amino acids
                (B) TYPE: amino acid
                (D) TOPOLOGY: linear (ii) MOLECULE TYPE: peptide (xi) SEQUENCE DESCRIPTION: SEQ ID NO:18:

Lys Ser Gln Asp Asn Val Thr Glu Lys Tyr Asp Val Ser
                  5                  10

(2) INFORMATION FOR SEQ ID NO:19:

(i) SEQUENCE CHARACTERISTICS:
                (A) LENGTH: 15 amino acids
                (B) TYPE: amino acid
                (D) TOPOLOGY: linear (ii) MOLECULE TYPE: peptide (xi) SEQUENCE DESCRIPTION: SEQ ID NO:19:

Trp Lys Trp Lys Lys Lys Arg Pro Arg Asn Ser Tyr Lys Cys
                5                   10                  15

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:20:

TGGCCCATGG CTTCAGA                                                          17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:21:

GCCAAAATGG ATCCCCA                                                          17

(2) INFORMATION FOR SEQ ID NO:22:

(i) SEQUENCE CHARACTERISTICS:
        (A) LENGTH: 1163 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 111..1040

(xi) SEQUENCE DESCRIPTION: SEQ ID NO:22:

CCCACGCGTC CGGGAGCAAG CAGACGCGTA AGAGTGGCTC CTGTAGGCAG CACGGACTTG    60

AACAACCAGA CTCCTGTAGA CGTGTTCCAG AACTTACGGA AGCACCCACG ATG GAC    116
                                                                                                   Met Asp
                                                                                                   1

CCC AGA TGC ACC ATG GGC TTG GCA ATC CTT ATC TTT GTG ACA GTC TTG    164
Pro Arg Cys Thr Met Gly Leu Ala Ile Leu Ile Phe Val Thr Val Leu
    5                    10                    15

CTG ATC TCA GAT GCT GTT TCC GTG GAG ACG CAA GCT TAT TTC AAT GGG    212
Leu Ile Ser Asp Ala Val Ser Val Glu Thr Gln Ala Tyr Phe Asn Gly
    20                  25                 30

ACT GCA TAT CTG CCG TGC CCA TTT ACA AAG GCT CAA AAC ATA AGC CTG    260
Thr Ala Tyr Leu Pro Cys Pro Phe Thr Lys Ala Gln Asn Ile Ser Leu
35                  40                  45                  50

AGT GAG CTG GTA GTA TTT TGG CAG GAC CAG CAA AAG TTG GTT CTG TAC    308
Ser Glu Leu Val Val Phe Trp Gln Asp Gln Gln Lys Leu Val Leu Tyr
                55                  60                  65

GAG CAC TAT TTG GGC ACA GAG AAA CTT GAT AGT GTG AAT GCC AAG TAC    356
Glu His Tyr Leu Gly Thr Glu Lys Leu Asp Ser Val Asn Ala Lys Tyr
                    70                  75                  80

```
CTG GGC CGC ACG AGC TTT GAC AGG AAC AAC TGG ACT CTA CGA CTT CAC       404
Leu Gly Arg Thr Ser Phe Asp Arg Asn Asn Trp Thr Leu Arg Leu His
        85                  90                  95

AAT GTT CAG ATC AAG GAC ATG GGC TCG TAT GAT TGT TTT ATA CAA AAA       452
Asn Val Gln Ile Lys Asp Met Gly Ser Tyr Asp Cys Phe Ile Gln Lys
100                 105                 110

AAG CCA CCC ACA GGA TCA ATT ATC CTC CAA CAG ACA TTA ACA GAA CTG       500
Lys Pro Pro Thr Gly Ser Ile Ile Leu Gln Gln Thr Leu Thr Glu Leu
115                 120                 125                 130

TCA GTG ATC GCC AAC TTC AGT GAA CCT GAA ATA AAA CTG GCT CAG AAT       548
Ser Val Ile Ala Asn Phe Ser Glu Pro Glu Ile Lys Leu Ala Gln Asn
                135                 140                 145

GTA ACA GGA AAT TCT GGC ATA AAT TTG ACC TGC ACG TCT AAG CAA GGT       596
Val Thr Gly Asn Ser Gly Ile Asn Leu Thr Cys Thr Ser Lys Gln Gly
            150                 155                 160

CAC CCG AAA CCT AAG AAG ATG TAT TTT CTG ATA ACT AAT TCA ACT AAT       644
His Pro Lys Pro Lys Lys Met Tyr Phe Leu Ile Thr Asn Ser Thr Asn
        165                 170                 175

GAG TAT GGT GAT AAC ATG CAG ATA TCA CAA GAT AAT GTC ACA GAA CTG       692
Glu Tyr Gly Asp Asn Met Gln Ile Ser Gln Asp Asn Val Thr Glu Leu
180                 185                 190

TTC AGT ATC TCC AAC AGC CTC TCT CTT TCA TTC CCG GAT GGT GTG TGG       740
Phe Ser Ile Ser Asn Ser Leu Ser Leu Ser Phe Pro Asp Gly Val Trp
195                 200                 205                 210

CAT ATG ACC GTT GTG TGT GTT CTG GAA ACG GAG TCA ATG AAG ATT TCC       788
His Met Thr Val Val Cys Val Leu Glu Thr Glu Ser Met Lys Ile Ser
                215                 220                 225

TCC AAA CCT CTC AAT TTC ACT CAA GAG TTT CCA TCT CCT CAA ACG TAT       836
Ser Lys Pro Leu Asn Phe Thr Gln Glu Phe Pro Ser Pro Gln Thr Tyr
            230                 235                 240

TGG AAG GAG ATT ACA GCT TCA GTT ACT GTG GCC CTC CTC CTT GTG ATG       884
Trp Lys Glu Ile Thr Ala Ser Val Thr Val Ala Leu Leu Leu Val Met
        245                 250                 255

CTG CTC ATC ATT GTA TGT CAC AAG AAG CCG AAT CAG CCT AGC AGG CCC       932
Leu Leu Ile Ile Val Cys His Lys Lys Pro Asn Gln Pro Ser Arg Pro
260                 265                 270

AGC AAC ACA GCC TCT AAG TTA GAG CGG GAT AGT AAC GCT GAC AGA GAG       980
Ser Asn Thr Ala Ser Lys Leu Glu Arg Asp Ser Asn Ala Asp Arg Glu
275                 280                 285                 290

ACT ATC AAC CTG AAG GAA CTT GAA CCC CAA ATT GCT TCA GCA AAA CCA      1028
Thr Ile Asn Leu Lys Glu Leu Glu Pro Gln Ile Ala Ser Ala Lys Pro
                295                 300                 305

AAT GCA GAG TGAAGGCAGT GAGAGCCTGA GGAAAGAGTT AAAAATTGCT              1077
Asn Ala Glu

TTGCCTGAAA TAAGAAGTGC AGAGTTTCTC AGAATTCAAA AATGTTCTCA GCTGATTGGA    1137

ATTCTACAGT TGAATAATTA AGAAC                                          1163

(2) INFORMATION FOR SEQ ID NO:23:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO:23:

Met Asp Pro Arg Cys Thr Met Gly Leu Ala Ile Leu Ile Phe Val Thr
  1               5                  10                  15

Val Leu Leu Ile Ser Asp Ala Val Ser Val Glu Thr Gln Ala Tyr Phe
```

```
                   20                  25                  30
Asn Gly Thr Ala Tyr Leu Pro Cys Pro Phe Thr Lys Ala Gln Asn Ile
            35                  40                  45
Ser Leu Ser Glu Leu Val Val Phe Trp Gln Asp Gln Lys Leu Val
 50                  55                  60
Leu Tyr Glu His Tyr Leu Gly Thr Glu Lys Leu Asp Ser Val Asn Ala
 65                  70                  75                  80
Lys Tyr Leu Gly Arg Thr Ser Phe Asp Arg Asn Asn Trp Thr Leu Arg
                 85                  90                  95
Leu His Asn Val Gln Ile Lys Asp Met Gly Ser Tyr Asp Cys Phe Ile
                100                 105                 110
Gln Lys Lys Pro Pro Thr Gly Ser Ile Ile Leu Gln Gln Thr Leu Thr
            115                 120                 125
Glu Leu Ser Val Ile Ala Asn Phe Ser Glu Pro Glu Ile Lys Leu Ala
130                 135                 140
Gln Asn Val Thr Gly Asn Ser Gly Ile Asn Leu Thr Cys Thr Ser Lys
145                 150                 155                 160
Gln Gly His Pro Lys Pro Lys Lys Met Tyr Phe Leu Ile Thr Asn Ser
                165                 170                 175
Thr Asn Glu Tyr Gly Asp Asn Met Gln Ile Ser Gln Asp Asn Val Thr
            180                 185                 190
Glu Leu Phe Ser Ile Ser Asn Ser Leu Ser Leu Ser Phe Pro Asp Gly
            195                 200                 205
Val Trp His Met Thr Val Val Cys Val Leu Glu Thr Glu Ser Met Lys
            210                 215                 220
Ile Ser Ser Lys Pro Leu Asn Phe Thr Gln Glu Phe Pro Ser Pro Gln
225                 230                 235                 240
Thr Tyr Trp Lys Glu Ile Thr Ala Ser Val Thr Val Ala Leu Leu Leu
                245                 250                 255
Val Met Leu Leu Ile Ile Val Cys His Lys Lys Pro Asn Gln Pro Ser
            260                 265                 270
Arg Pro Ser Asn Thr Ala Ser Lys Leu Glu Arg Asp Ser Asn Ala Asp
            275                 280                 285
Arg Glu Thr Ile Asn Leu Lys Glu Leu Glu Pro Gln Ile Ala Ser Ala
            290                 295                 300
Lys Pro Asn Ala Glu
305

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:24:

ACATAAGCCT GAGTGAGCTG G                                              21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

(ii) MOLECULE TYPE: oligonucleotide (xi) SEQUENCE DESCRIPTION: SEQ ID NO:25:

ATGATGAGCA GCATCACAAG G                                                   21

(2) INFORMATION FOR SEQ ID NO:26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:26:

TGGTCGAGTG AGTCCGAATA C                                                   21

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:27:

GACGAGTAGT AACATACAGT G                                                   21

(2) INFORMATION FOR SEQ ID NO:28:

(i) SEQUENCE CHARACTERISTICS:
            (A) LENGTH: 1491 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: no (iv) ANTI-SENSE: no (vi) ORIGINAL SOURCE:
            (A) ORGANISM: Homo sapien
            (F) TISSUE TYPE: lymphoid
            (G) CELL TYPE: B cell
            (H) CELL LINE: Raji (vii) IMMEDIATE SOURCE:
            (A) LIBRARY: cDNA in pCDM8 vector
            (B) CLONE: B7, Raji clone #13

(viii) POSITION IN GENOME:
            (A) CHROMOSOME/SEGMENT: 3

(ix) FEATURE:
            (A) NAME/KEY:  Open reading frame (translated region)
            (B) LOCATION:  318 to 1181 bp
            (C) IDENTIFICATION METHOD: similarity to other pattern (ix) FEATURE:
            (A) NAME/KEY:  Alternate polyadenylation signal
            (B) LOCATION:  1474 to 1479 bp
            (C) IDENTIFICATION METHOD: similarity to other pattern (x) PUBLICATION INFORMATION:
            (A) AUTHORS: FREEMAN, GORDON J.
                FREEDMAN, ARNOLD S.
                SEGIL, JEFFREY M.

LEE, GRACE
WHITMAN, JAMES F.
NADLER, LEE M.
(B) TITLE: B7, A New Member Of The Ig Superfamily With
Unique Expression On Activated And Neoplastic B Cells
(C) JOURNAL: The Journal of Immunology
(D) VOLUME: 143
(E) ISSUE: 8
(F) PAGES: 2714-2722
(G) DATE: 15-OCT-1989
(H) RELEVANT RESIDUES IN SEQ ID NO:28: FROM 1 TO 1491

(xi) SEQUENCE DESCRIPTION: SEQ ID NO:28:

```
CCAAAGAAAA AGTGATTTGT CATTGCTTTA TAGACTGTAA GAAGAGAACA TCTCAGAAGT        60

GGAGTCTTAC CCTGAAATCA AAGGATTTAA AGAAAAAGTG GAATTTTTCT TCAGCAAGCT       120

GTGAAACTAA ATCCACAACC TTTGGAGACC CAGGAACACC CTCCAATCTC TGTGTGTTTT       180

GTAAACATCA CTGGAGGGTC TTCTACGTGA GCAATTGGAT TGTCATCAGC CCTGCCTGTT       240

TTGCACCTGG GAAGTGCCCT GGTCTTACTT GGGTCCAAAT TGTTGGCTTT CACTTTTGAC       300

CCTAAGCATC TGAAGCC ATG GGC CAC ACA CGG AGG CAG GGA ACA TCA CCA TCC       353
                   Met Gly His Thr Arg Arg Gln Gly Thr Ser Pro Ser
                                    -30                 -25

AAG TGT CCA TAC CTG AAT TTC TTT CAG CTC TTG GTG CTG GCT GGT CTT         401
Lys Cys Pro Tyr Leu Asn Phe Phe Gln Leu Leu Val Leu Ala Gly Leu
        -20                 -15                 -10

TCT CAC TTC TGT TCA GGT GTT ATC CAC GTG ACC AAG GAA GTG AAA GAA         449
Ser His Phe Cys Ser Gly Val Ile His Val Thr Lys Glu Val Lys Glu
    -5                   1                   5                  10

GTG GCA ACG CTG TCC TGT GGT CAC AAT GTT TCT GTT GAA GAG CTG GCA         497
Val Ala Thr Leu Ser Cys Gly His Asn Val Ser Val Glu Glu Leu Ala
                15                  20                  25

CAA ACT CGC ATC TAC TGG CAA AAG GAG AAG AAA ATG GTG CTG ACT ATG         545
Gln Thr Arg Ile Tyr Trp Gln Lys Glu Lys Lys Met Val Leu Thr Met
            30                  35                  40

ATG TCT GGG GAC ATG AAT ATA TGG CCC GAG TAC AAG AAC CGG ACC ATC         593
Met Ser Gly Asp Met Asn Ile Trp Pro Glu Tyr Lys Asn Arg Thr Ile
        45                  50                  55

TTT GAT ATC ACT AAT AAC CTC TCC ATT GTG ATC CTG GCT CTG CGC CCA         641
Phe Asp Ile Thr Asn Asn Leu Ser Ile Val Ile Leu Ala Leu Arg Pro
    60                  65                  70

TCT GAC GAG GGC ACA TAC GAG TGT GTT GTT CTG AAG TAT GAA AAA GAC         689
Ser Asp Glu Gly Thr Tyr Glu Cys Val Val Leu Lys Tyr Glu Lys Asp
75                  80                  85                  90

GCT TTC AAG CGG GAA CAC CTG GCT GAA GTG ACG TTA TCA GTC AAA GCT         737
Ala Phe Lys Arg Glu His Leu Ala Glu Val Thr Leu Ser Val Lys Ala
                95                 100                 105

GAC TTC CCT ACA CCT AGT ATA TCT GAC TTT GAA ATT CCA ACT TCT AAT         785
Asp Phe Pro Thr Pro Ser Ile Ser Asp Phe Glu Ile Pro Thr Ser Asn
            110                 115                 120

ATT AGA AGG ATA ATT TGC TCA ACC TCT GGA GGT TTT CCA GAG CCT CAC         833
Ile Arg Arg Ile Ile Cys Ser Thr Ser Gly Gly Phe Pro Glu Pro His
        125                 130                 135

CTC TCC TGG TTG GAA AAT GGA GAA GAA TTA AAT GCC ATC AAC ACA ACA         881
Leu Ser Trp Leu Glu Asn Gly Glu Glu Leu Asn Ala Ile Asn Thr Thr
    140                 145                 150

GTT TCC CAA GAT CCT GAA ACT GAG CTC TAT GCT GTT AGC AGC AAA CTG         929
Val Ser Gln Asp Pro Glu Thr Glu Leu Tyr Ala Val Ser Ser Lys Leu
155                 160                 165                 170

GAT TTC AAT ATG ACA ACC AAC CAC AGC TTC ATG TGT CTC ATC AAG TAT         977
Asp Phe Asn Met Thr Thr Asn His Ser Phe Met Cys Leu Ile Lys Tyr
                175                 180                 185
```

```
GGA CAT TTA AGA GTG AAT CAG ACC TTC AAC TGG AAT ACA ACC AAG CAA        1025
Gly His Leu Arg Val Asn Gln Thr Phe Asn Trp Asn Thr Thr Lys Gln
        190                 195                 200

GAG CAT TTT CCT GAT AAC CTG CTC CCA TCC TGG GCC ATT ACC TTA ATC        1073
Glu His Phe Pro Asp Asn Leu Leu Pro Ser Trp Ala Ile Thr Leu Ile
        205                 210                 215

TCA GTA AAT GGA ATT TTT GTG ATA TGC TGC CTG ACC TAC TGC TTT GCC        1121
Ser Val Asn Gly Ile Phe Val Ile Cys Cys Leu Thr Tyr Cys Phe Ala
        220                 225                 230

CCA AGA TGC AGA GAG AGA AGG AGG AAT GAG AGA TTG AGA AGG GAA AGT        1169
Pro Arg Cys Arg Glu Arg Arg Arg Asn Glu Arg Leu Arg Arg Glu Ser
235                 240                 245                 250

GTA CGC CCT GTA  TAACAGTGTC CGCAGAAGCA AGGGGCTGAA AAGATCTGAA            1221
Val Arg Pro Val

GGTAGCCTCC GTCATCTCTT CTGGGATACA TGGATCGTGG GGATCATGAG GCATTCTTCC       1281

CTTAACAAAT TTAAGCTGTT TTACCCACTA CCTCACCTTC TTAAAAACCT CTTTCAGATT       1341

AAGCTGAACA GTTACAAGAT GGCTGGCATC CCTCTCCTTT CTCCCCATAT GCAATTTGCT       1401

TAATGTAACC TCTTCTTTTG CCATGTTTCC ATTCTGCCAT CTTGAATTGT CTTGTCAGCC       1461

AATTCATTAT CTATTAAACA CTAATTTGAG                                        1491

(2) INFORMATION FOR SEQ ID NO:29:

(i) SEQUENCE CHARACTERISTICS:
        (A) LENGTH: 288 amino acids
        (B) TYPE: amino acid
        (C) TOPOLOGY: linear (ii) MOLECULE TYPE: protein
         (A) DESCRIPTION: B cell activation antigen; natural ligand
             for CD28 T cell surface antigen; transmembrane protein (ix) FEATURE:
         (A) NAME/KEY: signal sequence
         (B) LOCATION: -34 to -1
         (C) IDENTIFICATION METHOD: amino terminal sequencing of
             soluble protein
         (D) OTHER INFORMATION: hydrophobic (ix) FEATURE:
         (A) NAME/KEY: extracellular domain
         (B) LOCATION: 1 to 208
         (C) IDENTIFICATION METHOD: similarity with known
             sequence (ix) FEATURE:
         (A) NAME/KEY: transmembrane domain
         (B) LOCATION: 209 to 235
         (C) IDENTIFICATION METHOD: similarity with known
             sequence (ix) FEATURE:
         (A) NAME/KEY: intracellular domain
         (B) LOCATION: 236 to 254
         (C) IDENTIFICATION METHOD: similarity with known
             sequence (ix) FEATURE:
         (A) NAME/KEY: N-linked glycosylation
         (B) LOCATION: 19 to 21
         (C) IDENTIFICATION METHOD: similarity with known
             sequence (ix) FEATURE:
         (A) NAME/KEY: N-linked glycosylation
         (B) LOCATION: 55 to 57
         (C) IDENTIFICATION METHOD: similarity with known
             sequence
```

```
    (ix) FEATURE:
         (A) NAME/KEY: N-linked glycosylation
         (B) LOCATION: 64 to 66
         (C) IDENTIFICATION METHOD: similarity with known
             sequence (ix) FEATURE:
         (A) NAME/KEY: N-linked glycosylation
         (B) LOCATION: 152 to 154
         (C) IDENTIFICATION METHOD: similarity with known
             sequence (ix) FEATURE:
         (A) NAME/KEY: N-linked glycosylation
         (B) LOCATION: 173 to 175
         (C) IDENTIFICATION METHOD: similarity with known
             sequence (ix) FEATURE:
         (A) NAME/KEY: N-linked glycosylation
         (B) LOCATION: 177 to 179
         (C) IDENTIFICATION METHOD: similarity with known
             sequence (ix) FEATURE:
         (A) NAME/KEY: N-linked glycosylation
         (B) LOCATION: 192 to 194
         (C) IDENTIFICATION METHOD: similarity with known
             sequence (ix) FEATURE:
         (A) NAME/KEY: N-linked glycosylation
         (B) LOCATION: 198 to 200
         (C) IDENTIFICATION METHOD: similarity with known
             sequence (ix) FEATURE:
         (A) NAME/KEY: Ig V-set domain
         (B) LOCATION: 1 to 104
         (C) IDENTIFICATION METHOD: similarity with known
             sequence (ix) FEATURE:
         (A) NAME/KEY: Ig C-set domain
         (B) LOCATION:  105 to 202
         (C) IDENTIFICATION METHOD: similarity with known
             sequence (x) PUBLICATION INFORMATION:
         (A) AUTHORS: FREEMAN, GORDON J.
                     FREEDMAN, ARNOLD S.
                     SEGIL, JEFFREY M.
                     LEE, GRACE
                     WHITMAN, JAMES F.
                     NADLER, LEE M.
         (B) TITLE: B7, A New Member Of The Ig Superfamily With
                    Unique Expression On Activated And Neoplastic B Cells
         (C) JOURNAL: The Journal of Immunology
         (D) VOLUME: 143
         (E) ISSUE: 8
         (F) PAGES: 2714-2722
         (G) DATE:  15-OCT-1989
         (H) RELEVANT RESIDUES IN SEQ ID NO:29: From -26 to 262

(xi) SEQUENCE DESCRIPTION: SEQ ID NO:29:

Met Gly His Thr Arg Arg Gln Gly Thr Ser Pro Ser Lys Cys Pro Tyr
                -30                 -25                 -20

Leu Asn Phe Phe Gln Leu Leu Val Leu Ala Gly Leu Ser His Phe Cys
            -15                 -10                  -5

Ser Gly Val Ile His Val Thr Lys Glu Val Lys Glu Val Ala Thr Leu
 -1   1              5                  10

Ser Cys Gly His Asn Val Ser Val Glu Glu Leu Ala Gln Thr Arg Ile
 15              20                  25                  30

Tyr Trp Gln Lys Glu Lys Lys Met Val Leu Thr Met Met Ser Gly Asp
```

-continued

```
                      35                  40                  45
Met Asn Ile Trp Pro Glu Tyr Lys Asn Arg Thr Ile Phe Asp Ile Thr
             50                  55                  60
Asn Asn Leu Ser Ile Val Ile Leu Ala Leu Arg Pro Ser Asp Glu Gly
         65                  70                  75
Thr Tyr Glu Cys Val Val Leu Lys Tyr Glu Lys Asp Ala Phe Lys Arg
     80                  85                  90
Glu His Leu Ala Glu Val Thr Leu Ser Val Lys Ala Asp Phe Pro Thr
 95                 100                 105                 110
Pro Ser Ile Ser Asp Phe Glu Ile Pro Thr Ser Asn Ile Arg Arg Ile
                115                 120                 125
Ile Cys Ser Thr Ser Gly Gly Phe Pro Glu Pro His Leu Ser Trp Leu
            130                 135                 140
Glu Asn Gly Glu Glu Leu Asn Ala Ile Asn Thr Thr Val Ser Gln Asp
        145                 150                 155
Pro Glu Thr Glu Leu Tyr Ala Val Ser Ser Lys Leu Asp Phe Asn Met
    160                 165                 170
Thr Thr Asn His Ser Phe Met Cys Leu Ile Lys Tyr Gly His Leu Arg
175                 180                 185                 190
Val Asn Gln Thr Phe Asn Trp Asn Thr Thr Lys Gln Glu His Phe Pro
                195                 200                 205
Asp Asn Leu Leu Pro Ser Trp Ala Ile Thr Leu Ile Ser Val Asn Gly
            210                 215                 220
Ile Phe Val Ile Cys Cys Leu Thr Tyr Cys Phe Ala Pro Arg Cys Arg
                225                 230                 235
Glu Arg Arg Arg Asn Glu Arg Leu Arg Arg Glu Ser Val Arg Pro Val
240                 245                 250
```

(2) INFORMATION FOR SEQ ID NO:30:

(i) SEQUENCE CHARACTERISTICS:
        (A) LENGTH: 1716 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: no (vi) ORIGINAL SOURCE:
        (A) ORGANISM: Mus musculus
        (D) DEVELOPMENTAL STAGE: germ line
        (F) TISSUE TYPE: lymphoid
        (G) CELL TYPE: B lymphocyte
        (H) CELL LINE: 70Z and A20

(vii) IMMEDIATE SOURCE:
        (A) LIBRARY: cDNA in pCDM8 vector
        (B) CLONE: B7 #'s 1 and 29

(ix) FEATURE:
        (A) NAME/KEY: translated region
        (B) LOCATION: 249 to 1166 bp
        (C) IDENTIFICATION METHOD: similarity to other pattern (ix) FEATURE:
        (A) NAME/KEY: Alternate ATG initiation codons
        (B) LOCATION: 225 to 227 and 270 to 272
        (C) IDENTIFICATION METHOD: similarity to other pattern (xi) SEQUENCE DESCRIPTION: SEQ ID NO:30:

GAGTTTTATA CCTCAATAGA CTCTTACTAG TTTCTCTTTT TCAGGTTGTG AAACTCAACC    60

-continued

```
TTCAAAGACA CTCTGTTCCA TTTCTGTGGA CTAATAGGAT CATCTTTAGC ATCTGCCGGG        120

TGGATGCCAT CCAGGCTTCT TTTTCTACAT CTCTGTTTCT CGATTTTGT GAGCCTAGGA         180

GGTGCCTAAG CTCCATTGGC TCTAGATTCC TGGCTTTCCC CATCATGTTC TCCAAAGCAT         240

CTGAAGCT ATG GCT TGC AAT TGT CAG TTG ATG CAG GAT ACA CCA CTC CTC          290
         Met Ala Cys Asn Cys Gln Leu Met Gln Asp Thr Pro Leu Leu
                     -35             -30             -25

AAG TTT CCA TGT CCA AGG CTC AAT CTT CTC TTT GTG CTG CTG ATT CGT           338
Lys Phe Pro Cys Pro Arg Leu Ile Leu Leu Phe Val Leu Leu Ile Arg
                -20             -15             -10

CTT TCA CAA GTG TCT TCA GAT GTT GAT GAA CAA CTG TCC AAG TCA GTG           386
Leu Ser Gln Val Ser Ser Asp Val Asp Glu Gln Leu Ser Lys Ser Val
             -5              -1   1               5

AAA GAT AAG GTA TTG CTG CCT TGC CGT TAC AAC TCT CCT CAT GAA GAT           434
Lys Asp Lys Val Leu Leu Pro Cys Arg Tyr Asn Ser Pro His Glu Asp
 10              15              20               25

GAG TCT GAA GAC CGA ATC TAC TGG CAA AAA CAT GAC AAA GTG GTG CTG           482
Glu Ser Glu Asp Arg Ile Tyr Trp Gln Lys His Asp Lys Val Val Leu
                 30              35               40

TCT GTC ATT GCT GGG AAA CTA AAA GTG TGG CCC GAG TAT AAG AAC CGG           530
Ser Val Ile Ala Gly Lys Leu Lys Val Trp Pro Glu Tyr Lys Asn Arg
             45              50               55

ACT TTA TAT GAC AAC ACT ACC TAC TCT CTT ATC ATC CTG GGC CTG GTC           578
Thr Leu Tyr Asp Asn Thr Thr Tyr Ser Leu Ile Ile Leu Gly Leu Val
         60              65               70

CTT TCA GAC CGG GGC ACA TAC AGC TGT GTC GTT CAA AAG AAG GAA AGA           626
Leu Ser Asp Arg Gly Thr Tyr Ser Cys Val Val Gln Lys Lys Glu Arg
 75              80               85

GGA ACG TAT GAA GTT AAA CAC TTG GCT TTA GTA AAG TTG TCC ATC AAA           674
Gly Thr Tyr Glu Val Lys His Leu Ala Leu Val Lys Leu Ser Ile Lys
 90              95              100              105

GCT GAC TTC TCT ACC CCC AAC ATA ACT GAG TCT GGA AAC CCA TCT GCA           722
Ala Asp Phe Ser Thr Pro Asn Ile Thr Glu Ser Gly Asn Pro Ser Ala
                110             115              120

GAC ACT AAA AGG ATT ACC TGC TTT GCT TCC GGG GGT TTC CCA AAG CCT           770
Asp Thr Lys Arg Ile Thr Cys Phe Ala Ser Gly Gly Phe Pro Lys Pro
             125             130              135

CGC TTC TCT TGG TTG GAA AAT GGA AGA GAA TTA CCT GGC ATC AAT ACG           818
Arg Phe Ser Trp Leu Glu Asn Gly Arg Glu Leu Pro Gly Ile Asn Thr
         140             145              150

ACA ATT TCC CAG GAT CCT GAA TCT GAA TTG TAC ACC ATT AGT AGC CAA           866
Thr Ile Ser Gln Asp Pro Glu Ser Glu Leu Tyr Thr Ile Ser Ser Gln
     155             160              165

CTA GAT TTC AAT ACG ACT CGC AAC CAC ACC ATT AAG TGT CTC ATT AAA           914
Leu Asp Phe Asn Thr Thr Arg Asn His Thr Ile Lys Cys Leu Ile Lys
170              175              180              185

TAT GGA GAT GCT CAC GTG TCA GAG GAC TTC ACC TGG GAA AAA CCC CCA           962
Tyr Gly Asp Ala His Val Ser Glu Asp Phe Thr Trp Glu Lys Pro Pro
                 190             195              200

GAA GAC CCT CCT GAT AGC AAG AAC ACA CTT GTG CTC TTT GGG GCA GGA          1010
Glu Asp Pro Pro Asp Ser Lys Asn Thr Leu Val Leu Phe Gly Ala Gly
             205             210              215

TTC GGC GCA GTA ATA ACA GTC GTC GTC ATC GTT GTC ATC ATC AAA TGC          1058
Phe Gly Ala Val Ile Thr Val Val Val Ile Val Val Ile Ile Lys Cys
         220             225              230

TTC TGT AAG CAC AGA AGC TGT TTC AGA AGA AAT GAG GCA AGC AGA GAA          1106
Phe Cys Lys His Arg Ser Cys Phe Arg Arg Asn Glu Ala Ser Arg Glu
     235             240              245

ACA AAC AAC AGC CTT ACC TTC GGG CCT GAA GAA GCA TTA GCT GAA CAG          1154
```

```
Thr Asn Asn Ser Leu Thr Phe Gly Pro Glu Glu Ala Leu Ala Glu Gln
250                 255                 260                 265

ACC GTC TTC CTT TAGTTCTTCT CTGTCCATGT GGGATACATG GTATTATGTG        1206
Thr Val Phe Leu

GCTCATGAGG TACAATCTTT CTTTCAGCAC CGTGCTAGCT GATCTTTCGG ACAACTTGAC  1266

ACAAGATAGA GTTAACTGGG AAGAGAAAGC CTTGAATGAG GATTTCTTTC CATCAGGAAG  1326

CTACGGGCAA GTTTGCTGGG CCTTTGATTG CTTGATGACT GAAGTGGAAA GGCTGAGCCC  1386

ACTGTGGGTG GTGCTAGCCC TGGGCAGGGG CAGGTGACCC TGGGTGGTAT AAGAAAAAGA  1446

GCTGTCACTA AAAGGAGAGG TGCCTAGTCT TACTGCAACT TGATATGTCA TGTTTGGTTG  1506

GTGTCTGTGG GAGGCCTGCC CTTTTCTGAA GAGAAGTGGT GGGAGAGTGG ATGGGGTGGG  1566

GGCAGAGGAA AAGTGGGGGA GAGGGCCTGG GAGGAGAGGA GGGAGGGGGA CGGGGTGGGG  1626

GTGGGGAAAA CTATGGTTGG GATGTAAAAA CGGATAATAA TATAAATATT AAATAAAAAG  1686

AGAGTATTGA GCAAAAAAAA AAAAAAAAA                                    1716
```

(2) INFORMATION FOR SEQ ID NO:31:

(i) SEQUENCE CHARACTERISTICS:
        (A) LENGTH: 306 amino acids
        (B) TYPE: amino acid
        (C) TOPOLOGY: linear (ii) MOLECULE TYPE: protein
       (A) DESCRIPTION: B lymphocyte activation antigen; Ig
           superfamily member; T cell costimulatory signal
           via activation of CD28 pathways, binds to CD28+
           T cells, transmembrane protein (ix) FEATURE:
       (A) NAME/KEY: signal sequence
       (B) LOCATION: -37 to -1
       (C) IDENTIFICATION METHOD: similarity with known
          sequence
       (D) OTHER INFORMATION: hydrophobic (ix) FEATURE:
       (A) NAME/KEY: extracellular domain
       (B) LOCATION: 1 to 210
       (C) IDENTIFICATION METHOD: similarity with known
          sequence (ix) FEATURE:
       (A) NAME/KEY: transmembrane domain
       (B) LOCATION: 211 to 235
       (C) IDENTIFICATION METHOD: similarity with known
          sequence (ix) FEATURE:
       (A) NAME/KEY: intracellular (cytoplasmic) domain
       (B) LOCATION: 236 to 269
       (C) IDENTIFICATION METHOD: similarity with known
          sequence (ix) FEATURE:
       (A) NAME/KEY: Ig V-set domain
       (B) LOCATION: 1 to 105
       (C) IDENTIFICATION METHOD: similarity with known
          sequence (ix) FEATURE:
       (A) NAME/KEY: Ig C-set domain
       (B) LOCATION:  106 to 199
       (C) IDENTIFICATION METHOD: similarity with known
          sequence (x) PUBLICATION INFORMATION:
        (A) AUTHORS: FREEMAN, GORDON J.
           GRAY, GARY S.
           GIMMI, CLAUDE D.

LOMBARD, DAVID B.
            ZHOU, LIANG-JI
            WHITE, MICHAEL
            FINGEROTH, JOYCE D.
            GRIBBEN, JOHN G.
            NADLER, LEE M.
    (B) TITLE: Structure, Expression, and T Cell Costimulatory
        Activity Of The Murine Homologue Of The Human B
        Lymphocyte Activation Antigen B7
    (C) JOURNAL: Journal of Experimental Medicine
    (D) VOLUME:
    (E) ISSUE:
    (F) PAGES:
    (G) DATE: IN PRESS
    (H) RELEVANT RESIDUES IN SEQ ID NO:31: From -37 to 269

(xi) SEQUENCE DESCRIPTION: SEQ ID NO:31:

Met Ala Cys Asn Cys Gln Leu Met Gln Asp Thr Pro Leu Leu Lys Phe
    -35                 -30                 -25

Pro Cys Pro Arg Leu Ile Leu Leu Phe Val Leu Leu Ile Arg Leu Ser
    -20                 -15                 -10

Gln Val Ser Ser Asp Val Asp Glu Gln Leu Ser Lys Ser Val Lys Asp
 -5              -1   1               5                   10

Lys Val Leu Leu Pro Cys Arg Tyr Asn Ser Pro His Glu Asp Glu Ser
                15                  20                  25

Glu Asp Arg Ile Tyr Trp Gln Lys His Asp Lys Val Val Leu Ser Val
        30                  35                  40

Ile Ala Gly Lys Leu Lys Val Trp Pro Glu Tyr Lys Asn Arg Thr Leu
        45                  50                  55

Tyr Asp Asn Thr Thr Tyr Ser Leu Ile Ile Leu Gly Leu Val Leu Ser
 60              65                  70                  75

Asp Arg Gly Thr Tyr Ser Cys Val Val Gln Lys Lys Glu Arg Gly Thr
 80                  85                  90

Tyr Gly Val Lys His Leu Ala Leu Val Lys Leu Ser Ile Lys Ala Asp
                95                  100                 105

Phe Ser Thr Pro Asn Ile Thr Glu Ser Gly Asn Pro Ser Ala Asp Thr
        110                 115                 120

Lys Arg Ile Thr Cys Phe Ala Ser Gly Gly Phe Pro Lys Pro Arg Phe
        125                 130                 135

Ser Trp Leu Glu Asn Gly Arg Glu Leu Pro Gly Ile Asn Thr Thr Ile
140                 145                 150                 155

Ser Gln Asp Pro Glu Ser Glu Leu Tyr Thr Ile Ser Ser Gln Leu Asp
                160                 165                 170

Phe Asn Thr Thr Arg Asn His Thr Ile Lys Cys Leu Ile Lys Tyr Gly
                175                 180                 185

Asp Ala His Val Ser Glu Asp Phe Thr Trp Glu Lys Pro Pro Glu Asp
                190                 195                 200

Pro Pro Asp Ser Lys Asn Thr Leu Val Leu Phe Gly Ala Gly Phe Gly
    205                 210                 215

Ala Val Ile Thr Val Val Val Ile Val Val Ile Ile Lys Cys Phe Cys
220                 225                 230                 235

Lys His Arg Ser Cys Phe Arg Arg Asn Glu Ala Ser Arg Glu Thr Asn
                240                 245                 250

Asn Ser Leu Thr Phe Gly Pro Glu Glu Ala Leu Ala Glu Gln Thr Val
                255                 260                 265

Phe Leu (2) INFORMATION FOR SEQ ID NO:32:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: oligonucleotide (xi) SEQUENCE DESCRIPTION: SEQ ID NO:32:

GGCACTAGGT CTCCAGCTTG AGATCACAGT TCTCTCTAC                    39

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:33:

GCTTGAATCT TCAGAGGAGC GGAGTGGACA CCTGTGG                      37

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:34:

GCTCCTCTGA AGATTCAAGC                                         20

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GGCACTATGA TCAGGGGGAG GCTGAGGTCC                               30

(2) INFORMATION FOR SEQ ID NO:36:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:36:

GCATTTTAAG CTTTTTCCTG ATCAGGAGCC CAAATCTTCT GACAAAACTC ACACATCTCC    60

ACCGTCTCCA GGTAAGCC                                                 78

(2) INFORMATION FOR SEQ ID NO:37:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:37:

TAATACGACT CACTATAGGG                                              20

(2) INFORMATION FOR SEQ ID NO:38:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:38:

GAGCATTTTC CTGATCAGGA GTCCAAATAT GGTCCCCCAT CCCATCATCC CCAGGTAAGC    60

CAACCC                                                              66

(2) INFORMATION FOR SEQ ID NO:39:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:39:

GCAGAGGAAT CGAGCTCGGT ACCCGGGGAT CCCCAGTGTG GGGACAGTGG GACCGCTCTG    60

CCTCCC                                                              66

(2) INFORMATION FOR SEQ ID NO:40:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:40:

GGGTTTTGGG GGGAAGAGGA AGACTGACGG TGCCCCCTCG GCTTCAGGTG CTGAGGAAG     59

(2) INFORMATION FOR SEQ ID NO:41:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:41:

CATCTCTTCC TCAGCACCTG AAGCCGAGGG GGCACCGTCA GTCTTCCTCT TCCCCC        56

(2) INFORMATION FOR SEQ ID NO:42:

(i) SEQUENCE CHARACTERISTICS:

(A) LENGTH: 99 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:42:

CGCACGTGAC CTCAGGGGTC CGGGAGATCA TGAGAGTGTC CTTGGGTTTT GGGGGGAACA    60

GGAAGACTGA TGGTGCCCCC TCGAACTCAG GTGCTGAGG    99

(2) INFORMATION FOR SEQ ID NO:43:

(i) SEQUENCE CHARACTERISTICS:
(A) LENGTH: 98 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:43:

CCTCAGCACC TGAGTTCGAG GGGGCACCAT CAGTCTCCTG TTCCCCCCAA AACCCAAGGA    60

CACTCTCATG ATCTCCCGGA CCCCTGAGGT CACGTGCG    98

(2) INFORMATION FOR SEQ ID NO:44:

(i) SEQUENCE CHARACTERISTICS:
(A) LENGTH: 330 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..330

(xi) SEQUENCE DESCRIPTION: SEQ ID NO:44:

```
GCT CCT CTG AAG ATT CAA GCT TAT TTC AAT GAG ACT GCA GAC CTG CCA    48
Ala Pro Leu Lys Ile Gln Ala Tyr Phe Asn Glu Thr Ala Asp Leu Pro
 1               5                  10                  15

TGC CAA TTT GCA AAC TCT CAA AAC CAA AGC CTG AGT GAG CTA GTA GTA    96
Cys Gln Phe Ala Asn Ser Gln Asn Gln Ser Leu Ser Glu Leu Val Val
            20                  25                  30

TTT TGG CAG GAC CAG GAA AAC TTG GTT CTG AAT GAG GTA TAC TTA GGC   144
Phe Trp Gln Asp Gln Glu Asn Leu Val Leu Asn Glu Val Tyr Leu Gly
        35                  40                  45

AAA GAG AAA TTT GAC AGT GTT CAT TCC AAG TAT ATG GGC CGC ACA AGT   192
Lys Glu Lys Phe Asp Ser Val His Ser Lys Tyr Met Gly Arg Thr Ser
 50                  55                  60

TTT GAT TCG GAC AGT TGG ACC CTG AGA CTT CAC AAT CTT CAG ATC AAG   240
Phe Asp Ser Asp Ser Trp Thr Leu Arg Leu His Asn Leu Gln Ile Lys
 65                  70                  75                  80

GAC AAG GGC TTG TAT CAA TGT ATC ATC CAT CAC AAA AAG CCC ACA GGA   288
Asp Lys Gly Leu Tyr Gln Cys Ile Ile His His Lys Lys Pro Thr Gly
                85                  90                  95

ATG ATT CGC ATC CAC CAG ATG AAT TCT AGG CTG TCA GTG CTT            330
Met Ile Arg Ile His Gln Met Asn Ser Arg Leu Ser Val Leu
                100                 105                 110
```

(2) INFORMATION FOR SEQ ID NO:45:

(i) SEQUENCE CHARACTERISTICS:

(A) LENGTH: 110 amino acids
(B) TYPE: amino acid
(D) TOPOLOGY: linear (ii) MOLECULE TYPE: protein (xi) SEQUENCE DESCRIPTION: SEQ ID NO:45:

```
Ala Pro Leu Lys Ile Gln Ala Tyr Phe Asn Glu Thr Ala Asp Leu Pro
 1               5                  10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val His Ser Lys Tyr Met Gly Arg Thr Ser
 50                  55                  60

Phe Asp Ser Asp Ser Trp Thr Leu Arg Leu His Asn Leu Gln Ile Lys
 65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Arg Leu Ser Val Leu
                100                 105                 110
```

(2) INFORMATION FOR SEQ ID NO:46:

(i) SEQUENCE CHARACTERISTICS:
(A) LENGTH: 306 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..310

(xi) SEQUENCE DESCRIPTION: SEQ ID NO:46:

```
GCT AAC TTC AGT CAA CCT GAA ATA GTA CCA ATT TCT AAT ATA ACA GAA        48
Ala Asn Phe Ser Gln Pro Glu Ile Val Pro Ile Ser Asn Ile Thr Glu
 1               5                  10                  15

AAT GTG TAC ATA AAT TTG ACC TGC TCA TCT ATA CAC GGT TAC CCA GAA        96
Asn Val Tyr Ile Asn Leu Thr Cys Ser Ser Ile His Gly Tyr Pro Glu
                20                  25                  30

CCT AAG AAG ATG AGT GTT TTG CTA AGA ACC AAG AAT TCA ACT ATC GAG       144
Pro Lys Lys Met Ser Val Leu Leu Arg Thr Lys Asn Ser Thr Ile Glu
            35                  40                  45

TAT GAT GGT ATT ATG CAG AAA TCT CAA GAT AAT GTC ACA GAA CTG TAC       192
Tyr Asp Gly Ile Met Gln Lys Ser Gln Asp Asn Val Thr Glu Leu Tyr
 50                  55                  60

GAC GTT TCC ATC AGC TTG TCT GTT TCA TTC CCT GAT GTT ACG AGC AAT       240
Asp Val Ser Ile Ser Leu Ser Val Ser Phe Pro Asp Val Thr Ser Asn
 65                  70                  75                  80

ATG ACC ATC TTC TGT ATT CTG GAA ACT GAC AAG ACG CGG CTT TTA TCT       288
Met Thr Ile Phe Cys Ile Leu Glu Thr Asp Lys Thr Arg Leu Leu Ser
                85                  90                  95

TCA CCT TTC TCT ATA GAG                                                306
Ser Pro Phe Ser Ile Glu
                100
```

(2) INFORMATION FOR SEQ ID NO:47:

(i) SEQUENCE CHARACTERISTICS:
(A) LENGTH: 102 amino acids

```
            (B) TYPE: amino acid
            (D) TOPOLOGY: linear (ii) MOLECULE TYPE: protein (xi) SEQUENCE DESCRIPTION: SEQ ID NO:47:

Ala Asn Phe Ser Gln Pro Glu Ile Val Pro Ile Ser Asn Ile Thr Glu
 1               5                  10                  15

Asn Val Tyr Ile Asn Leu Thr Cys Ser Ser Ile His Gly Tyr Pro Glu
                20                  25                  30

Pro Lys Lys Met Ser Val Leu Leu Arg Thr Lys Asn Ser Thr Ile Glu
            35                  40                  45

Tyr Asp Gly Ile Met Gln Lys Ser Gln Asp Asn Val Thr Glu Leu Tyr
        50                  55                  60

Asp Val Ser Ile Ser Leu Ser Val Ser Phe Pro Asp Val Thr Ser Asn
 65                  70                  75                  80

Met Thr Ile Phe Cys Ile Leu Glu Thr Asp Lys Thr Arg Leu Leu Ser
                85                  90                  95

Ser Pro Phe Ser Ile Glu
            100

(2) INFORMATION FOR SEQ ID NO:48:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:48:

GCAACCGGAA GCTTGCCACC ATGGGGGTAC TGCTCACACA GAGGACG                47

(2) INFORMATION FOR SEQ ID NO:49:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:49:

AGTCTCATTG AAATAAGCTT GAATCTTCAG AGGAGCCATG CTGGCCATGC TTGGAAACAG    60

GAG                                                                 63

(2) INFORMATION FOR SEQ ID NO:50:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:50:

CTCCTGTTTC CAAGCATGGC CAGCATGGCT CCTCTGAAGA TTCAGGCTTA TTTCAATGAG    60

AC                                                                  62

(2) INFORMATION FOR SEQ ID NO:51:
```

```
        (i) SEQUENCE CHARACTERISTICS:
              (A) LENGTH: 51 base pairs
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO:51:

TGTGTGTGGA ATTCTCATTA CTGATCAAGC ACTGACAGTT CAGAATTCAT C              51

(2) INFORMATION FOR SEQ ID NO:52:

(i) SEQUENCE CHARACTERISTICS:
              (A) LENGTH: 63 base pairs
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO:52:

AGAAATTGGT ACTATTTCAG GTTGACTGAA GTTAGCCATG CTGGCCATGC TTGGAAACAG     60

GAG                                                                  63

(2) INFORMATION FOR SEQ ID NO:53:

(i) SEQUENCE CHARACTERISTICS:
              (A) LENGTH: 62 base pairs
              (B) TYPE: nucleic acid
              (C) STRANDEDNESS: single
              (D) TOPOLOGY: linear (ii) MOLECULE TYPE: oligonucleotide (xi) SEQUENCE DESCRIPTION: SEQ ID NO:53:

CTCCTGTTTC CAAGCATGGC CAGCATGGCT AACTTCAGTC AACCTGAAAT AGTACCAATT     60

TC                                                                   62
```